US006767721B2

(12) United States Patent
Wisnewski et al.

(10) Patent No.: US 6,767,721 B2
(45) Date of Patent: Jul. 27, 2004

(54) FLEA ECDYSONE NUCLEIC ACID MOLECULES AND USES THEREOF

(76) Inventors: Nancy Wisnewski, 4219 Beaver Creek Dr., Fort Collins, CO (US) 80526; Anna M. Becher, 4500 Seneca St., Unit 33, Fort Collins, CO (US) 80526; Eric Jarvis, 3720 Smuggler Pl., Boulder, CO (US) 80303

( * ) Notice: Subject to any disclaimer, the term of this patent is extended or adjusted under 35 U.S.C. 154(b) by 0 days.

(21) Appl. No.: 10/065,200

(22) Filed: Sep. 25, 2002

(65) Prior Publication Data

US 2003/0064478 A1 Apr. 3, 2003

Related U.S. Application Data

(62) Division of application No. 09/435,019, filed on Nov. 5, 1999, now Pat. No. 6,489,140.
(60) Provisional application No. 60/107,559, filed on Nov. 6, 1998.

(51) Int. Cl.$^7$ .......................... C12P 21/06; C12N 15/74; C12N 5/02; C07H 21/04; C07K 14/00
(52) U.S. Cl. ................... 435/69.1; 435/320.1; 435/325; 435/336; 536/23.5; 530/350; 530/389.2
(58) Field of Search .......................... 435/69.1, 320.1, 435/325, 336; 536/23.5; 530/350, 389.2

(56) References Cited

U.S. PATENT DOCUMENTS 6,300,488 B1 * 10/2001 Gage et al. ................. 536/23.4
6,379,945 B1 * 4/2002 Jepson et al. ................ 435/243

FOREIGN PATENT DOCUMENTS

WO   WO 96/37609   * 11/1996
WO   WO 98/35550   * 8/1998

OTHER PUBLICATIONS

GenBank Accession No. U19812, 1996.*
GenBank Accession No. U29531, 1999.*
GenBank Accession No. D43943, 1999.*
Cooke et al., 1996, GenBank Accession 1350913.
Antoniewski et al., 1993, *Insect Biochem. Molec. Biol.*, vol. 23, No. 1, pp. 105–114.
Antoniewski et al., 1994, *Molecular and Cellular Biology*, vol. 14, No. 7, pp. 4465–4474.
Antoniewski et al., 1996, *Molecular and Cellular Biology*, vol. 16, No. 6, pp. 2977–2986.
Blumberg et al., 1992, *Proc. Natl. Acad. Sci.*, vol. 89, pp. 2321–2325.
Christianson et al., 1992, *Proc. Natl. Acad. Sci. USA*, vol. 89, pp. 11503–11507.
D'Avino et al., 1995, *Molecular and Cellular Endocrinology*, vol. 113, pp. 1–9.
Dhadialla et al., 1997, *Archives of Insect Biochemistry and Physiology*, vol. 35, pp. 45–57.
Elke et al., 1997, *Archives of Insect Biochemistry and Physiology*, vol. 35, pp. 59–69.
Fujiwara et al., 1995, *Insect Biochem. Molecular Biol.*, vol. 25, No. 7, pp. 845–856.
Giguere et al., 1987, *Nature*, vol. 330, pp. 624–629.
Guo et al., 1998, *Molecular and Cellular Endocrinology*, vol. 139, pp. 45–60.
Hannan et al., 1997, *Insect Biochem. Molec. Biol.*, vol. 27, No. 6, pp. 479–488.
Henrich et al., 1990, *Nucleic Acids Research*, vol. 18, No. 14, pp. 4143–4148.
Henrich et al., 1994, *Developmental Biology*, vol. 165, pp. 38–52.
Jindra et al., 1996, *Developmental Biology*, vol. 180, pp. 258–272.
Jindra et al., 1997, *Insect Molecular Biology*, vol. 6, No. 1, pp. 41–53.
Jones et al., 1997, *Proc. Natl. Acad. Sci. USA*, vol. 94, pp. 13499–13503.
Kamimura et al., 1996, *Comp. Biochem. Physiol.*, vol. 113B, No. 2, pp. 341–347.
Kapitskaya et al., 1996, *Molecular and Cellular Endocrinology*, vol. 121, pp. 119–132.
Koelle et al., 1991, *Cell*, vol. 67, pp. 59–77.
Kothapalli et al., 1995, *Developmental Genetics*, vol. 17, pp. 319–330.
Leid et al., 1992, *Cell*, vol. 68, pp. 377–395.
Li et al., 1997, *Proc. Natl. Acad. Sci USA*, vol. 94, pp. 2278–2283.
Nakagawa et al., 1998, *Pestic. Sci.*, vol. 53, pp. 267–277.
Perera et al., 1998, *Developmental Genetics*, vol. 22, pp. 169–179.
Rauch et al., 1998, *Insect Biochemistry and Molecular Biology*, vol. 28, pp. 265–275.
Rusin et al., 1996, *Acta Biochimica Polonica*, vol. 43, No. 4, pp. 611–621.
Song et al., 1997, *Insect Biochem. Molec. Biol.*, vol. 27, No. 11, pp. 973–982.
Swevers et al., 1996, *Insect Biochem. Molec. Biol.*, vol. 26, No. 3, pp. 217–221.

(List continued on next page.)

*Primary Examiner*—Janet Andes
(74) *Attorney, Agent, or Firm*—Heska Corporation

(57) ABSTRACT

The present invention relates to flea ecdysone receptor and ultraspiracle proteins; to flea ecdysone receptor and ultraspiracle nucleic acid molecules, including those that encode such flea ecdysone receptor and ultraspiracle proteins; to antibodies raised against such flea ecdysone receptor and ultraspiracle proteins; and to compounds that inhibit flea ecdysone receptor and/or ultraspiracle activity. The present invention also includes methods to obtain such proteins, nucleic acid molecules, antibodies, and inhibitory compounds. Also included in the present invention are therapeutic compositions comprising a protective compound derived from a protein of the present invention that inhibits the binding between ecdysone receptor and ecdysone as well as the use of such therapeutic compositions to protect animals from flea infestation.

10 Claims, No Drawings

U.S. PATENT DOCUMENTS

Swevers et al., *Insect Biochem. Molec. Biol.*, vol. 25, No. 7, pp. 857–866.
Talbot et al., 1993, *Cell*, vol. 73, pp. 1323–1337.
Thummel, Carl S., 1996, *Cell*, vol. 83, pp. 871–877.
Turberg et al., 1988, *J. Insect Physiol.*, vol. 34, No. 8, pp. 797–803.
Turberg et al., 1992, *J. Insect Physiol.*, vol. 38, No. 2, pp. 81–91.
Yao et al., 1992, *Cell*, vol. 71, pp. 63–72.
Yao et al., 1993, *Nature*, vol. 366, pp. 476–479.
Yates et al., 1995, *Molecular and Biochemical Parasitology*, vol. 70, pp. 19–31.

* cited by examiner

FLEA ECDYSONE NUCLEIC ACID MOLECULES AND USES THEREOF

CROSS REFERENCE TO RELATED APPLICATIONS

The present application is a Divisional of U.S. Ser. No. 09/435,019, filed Nov. 5, 1999, which issued as U.S. Pat. No. 6,489,140 B1, which claims priority to U.S. Provisional Patent, Application Ser. No. 60/107,559, filed Nov. 6, 1998, each entitled "NOVEL FLEA ECDYSONE AND ULTRASPIRACLE NUCLEIC ACID MOLECULES, PROTEINS AND USES THEREOF".

FIELD OF THE INVENTION

The present invention relates to flea ecdysone and ultraspiracle nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from flea infestation.

BACKGROUND OF THE INVENTION

Flea infestation of animals is a health and economic concern because fleas are known to cause and/or transmit a variety of diseases. Fleas directly cause a variety of diseases, including allergies, and also carry a variety of infectious agents including, but not limited to, endoparasites (e.g., nematodes, cestodes, trematodes and protozoa), bacteria and viruses. In particular, the bites of fleas are a problem for animals maintained as pets because the infestation becomes a source of annoyance not only for the pet but also for the pet owner who may find his or her home generally contaminated with insects. As such, fleas are a problem not only when they are on an animal but also when they are in the general environment of the animal.

Bites from fleas are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of flea infestation has prompted the development of reagents capable of controlling flea infestation. Commonly encountered methods to control flea infestation are generally focused on use of insecticides. While some of these products are efficacious, most, at best, offer protection of a very limited duration. Furthermore, many of the methods are often not successful in reducing flea populations. In particular, insecticides have been used to prevent flea infestation of animals by adding such insecticides to shampoos, powders, collars, sprays, foggers and liquid bath treatments (i.e., dips). Reduction of flea infestation on the pet has been unsuccessful for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Flea populations, however, have been found to become resistant to insecticides.

20-Hydroxyecdysone (ecdysone) is the insect steroid hormone which regulates molting and metamorphosis. The ability of ecdysone to have a pleiotropic effect upon various tissues is dependent upon the formation of a complex of ecdysone with its receptor (EcR) and its heterodimeric partner, ultraspiracle (USP). This complex then binds to ecdysone response elements (EcRE) found within the promoters of insect genes, and thereby affecting DNA transcription. EcR by itself has been reported to be incapable of high affinity binding or transcriptional activation, rather, these activities appear to be dependent upon heterodimer formation with USP, Yao et al., 1993, Nature 366, 476–479.

Prior investigators have described certain insect EcR protein or nucleic acid sequences, including for example, *Bombyx mori*, Swevers et al., 1995, Insect Biochem. Mol Biol. 25(7), 857–866; *Drosophila melanogaster*, Koelle et al., 1991, Cell 67(1), 59 and *Manduca sexta*, Fujiwara et al.,1995, Insect Biochem. Mol. Biol. 25 (7), 845 and certain insect USP protein and nucleic acid sequences, including for example, *Bombyx mori*, Tzertzinis et al., 1994, J. Mol. Biol. 238, 479–486; *Drosophila melanogaster*, Oro et al., 1990, Nature, 347(6290) 298–301; and *Manduca sexta*, Jindra et al., GenBank Accession 1718061. Prior investigators have also described mammalian homologs of EcR and USP, Giguere et al., 1987, Nature 330 (6149), 624–629; Cooke et al., 1996, GenBank Accession 1350913; Leid et al., 1992, Cell 68(2), 377–395; and amphibian homologs, Blumberg et al., 1992, Proc. Natl. Acad. Sci., U.S.A. 89(6), 2321–2325.

Identification of flea EcR and USP of the present invention is surprising, however, due to the source from which these molecules were identified. Most lepidopterans and dipterans are better characterized, relative to *C. felis*, with respect to visible signs of molting, the only stages which should possess high levels of ecdysone. Ecdysone is necessary for the up regulation of mRNA encoding EcR and USP. Therefore, the lack of clear, easily visible signs of molting in *C. felis* make the likelihood of finding cDNA containing EcR or USP message in the larval and prepupal cDNA unexpected.

Thus, there remains a need to develop a reagent and a method to protect animals from flea infestation.

SUMMARY OF INVENTION

The present invention relates to a novel product and process for protection of animals from flea infestation. Identification of flea EcR and USP of the present invention is surprising, however, due to the source from which these molecules were identified. Most lepidopterans and dipterans are better characterized, relative to *C. felis*, with respect to visible signs of molting, the only stages which should possess high levels of ecdysone. Ecdysone is necessary for the up regulation of mRNA encoding EcR and USP. Therefore, the lack of clear, easily visible signs of molting in *C. felis* make the likelihood of finding cDNA containing EcR or USP message in the larval and prepupal cDNA unexpected.

According to the present invention there are provided flea ecdysone receptor (EcR) or ultraspiracle (USP) proteins, and mimetopes thereof; flea EcR and USP nucleic acid molecules, including those that encode such proteins; antibodies raised against such EcR and USP proteins (i.e., anti-flea EcR and USP antibodies); and compounds that inhibit flea EcR and USP activity (i.e., inhibitory compounds or inhibitors).

The present invention also includes methods to obtain such proteins, mimetopes, nucleic acid molecules, antibodies and inhibitory compounds. Also included in the present invention are therapeutic compositions comprising a protective compound derived from a protein of the present invention that inhibits the binding between ecdysone receptor and ecdysone.

One embodiment of the present invention is an isolated nucleic acid molecule having at least about 34 nucleotides which hybridizes with a nucleic acid sequence having SEQ ID NO:5, SEQ ID NO:7, SEQ ID NO:8, SEQ ID NO:10, SEQ ID NO:13, SEQ ID NO:15, SEQ ID NO:16 and/or SEQ ID NO:18 under conditions that allow about 30% base pair mismatch. Another embodiment of the present invention is an isolated nucleic acid molecule having at least about 30 nucleotides which hybridizes with a nucleic acid sequence having SEQ ID NO:26, SEQ ID NO:28, SEQ ID NO:29; SEQ ID NO:31, SEQ ID NO:32, SEQ ID NO:34, SEQ ID NO:35 and/or SEQ ID NO:37 under conditions that allow about 30% base pair mismatch.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

The present invention also relates to mimetopes of flea EcR and/or USP proteins as well as to isolated antibodies that selectively bind to flea EcR and/or USP proteins or mimetopes thereof. Also included are methods, including recombinant methods, to produce proteins, mimetopes and antibodies of the present invention.

Another embodiment of the present invention includes an isolated flea ecdysone receptor protein selected from the group consisting of a protein comprising (a) an amino acid sequence that is at least about 70% identical to an amino acid sequence selected from the group consisting of SEQ ID NO:6 and/or SEQ ID NO:14, wherein said protein is at least about 71 amino acids residues in length; (b) a protein consisting of an amino acid sequence having SEQ ID NO:64 and/or SEQ ID NO:65, and fragments thereof, wherein said protein has at least a portion of an ecdysone receptor DNA binding domain; (c) a protein consisting of an amino acid sequence having SEQ ID NO:66 and/or SEQ ID NO:67, and fragments thereof, wherein said protein has at least a portion of an ecdysone receptor ligand binding domain; or (d) a protein encoded by an allelic variant of nucleic acid molecules encoding any protein of (a), (b), and/or (c).

Another embodiment of the present invention includes an isolated flea ultraspiracle protein selected from the group consisting of: (a) a protein comprising an amino acid sequence that is at least about 70% identical to an amino acid sequence selected from the group consisting of SEQ ID NO:27 and SEQ ID NO:33, wherein said protein is at least about 72 amino acid residues in length; (b) a protein consisting of an amino acid sequence selected from the group consisting of SEQ ID NO:68, SEQ ID NO:69, SEQ ID NO:70, SEQ ID NO:71, and fragments thereof, wherein said protein has at least a portion of an ultraspiracle protein that is capable of affecting binding of ecdysone receptor to ecdysone; and (c) a protein encoded by an allelic variant of a nucleic acid molecule which encodes any protein of (a) or (b).

Another embodiment of the present invention includes an isolated protein encoded by a nucleic acid molecule having a nucleic acid sequence selected from the group consisting of SEQ ID NO:5, SEQ ID NO:8, SEQ ID NO:13, SEQ ID NO:16, SEQ ID NO:26, SEQ ID NO:29, SEQ ID NO:32, and/or SEQ ID NO:35.

Another embodiment of the present invention includes a method to identify a compound capable of inhibiting EcR activity, the method comprising: (a) contacting an isolated flea EcR protein comprising an amino acid sequence selected from the group consisting of SEQ ID NO:6 and SEQ ID NO:14, with a putative inhibitory compound under conditions in which, in the absence of the putative inhibitory compound, the protein has EcR activity, and (b) determining if the putative inhibitory compound inhibits EcR activity.

Another embodiment of the present invention includes a method to identify a compound capable of inhibiting flea activity, the method comprising: (a) contacting an isolated flea USP protein comprising an amino acid sequence consisting of SEQ ID NO:27 and SEQ ID NO:33, with a putative inhibitory compound under conditions in which, in the absence of the putative inhibitory compound, the protein has USP activity, and (b) determining if the putative inhibitory compound inhibits USP activity.

DETAILED DESCRIPTION

The present invention provides for isolated flea ecdysone (EcR) and ultraspiracle (USP) proteins, isolated flea EcR and USP nucleic acid molecules, isolated antibodies directed against flea EcR and USP proteins, and compounds able to inhibit flea EcR and/or USP function (i.e., inhibitory compounds). As used herein, the terms isolated flea EcR and USP proteins and isolated flea EcR and USP nucleic acid molecules refer to EcR and USP proteins and EcR and USP nucleic acid molecules derived from fleas; as such the proteins and nucleic acid molecules can be isolated from an organism or prepared recombinantly or synthetically. Flea EcR nucleic acid molecules of known length are denoted "nECR$_{\#}$", for example nECR$_{4148}$, wherein "#" refers to the number of nucleotides in that molecule, and EcR proteins of known length are denoted "Pecr$_{\#}$"(for example Pecr$_{562}$) wherein "#" refers to the number of amino acid residues in that molecule. Similarly, USP nucleic acid molecules and proteins of known length are denoted "nUSP$_{\#}$" and "Pusp$_{\#}$", respectively. The proteins and nucleic acid molecules of the present invention can be obtained from their natural source, or can be produced using, for example, recombinant nucleic acid technology or chemical synthesis. Also included in the present invention is the use of these proteins, nucleic acid molecules, antibodies, and inhibitory compounds as therapeutic compositions to protect animals from flea infestation as well as in other applications, such as those disclosed below.

Flea EcR and USP proteins and nucleic acid molecules of the present invention have utility because they represent novel targets for anti-arthropod vaccines and chemotherapeutic drugs. The products and processes of the present invention are advantageous because they enable the inhibition of arthropod development, metamorphosis, feeding, digestion and reproduction processes that involve EcR and/or USP proteins. While not being bound by theory, it is believed that expression of arthropod EcR and USP proteins are developmentally regulated, thereby suggesting that EcR and USP proteins are involved in arthropod development and/or reproduction. The present invention is particularly advantageous because the proteins of the present invention were identified in larval fleas, thereby suggesting the importance of the proteins as developmental proteins.

Tissue can be obtained from unfed fleas or from fleas that recently consumed a blood meal (i.e., blood-fed fleas). Such flea tissues are referred to herein as, respectively, unfed flea and fed flea tissue. Preferred flea tissue from which to obtain an EcR and/or USP formulation of the present invention include, but are not limited to, unfed or fed 1$^{st}$ instar larvae;

fed 3$^{rd}$ instar larvae, fed wandering larvae, fed prepupal larvae, fed pupae and whole unfed or fed adult fleas. Preferred flea tissue from which to obtain an EcR and/or USP formulation of the present invention includes third instar larvae, wandering larvae, prepupal larvae, pupae, and adult fleas.

In a preferred embodiment, a formulation of the present invention comprises a flea EcR protein comprising amino acid sequence SEQ ID NO:6 or SEQ ID NO:14, and/or a flea USP protein comprising amino acid sequence SEQ ID NO:27 or SEQ ID NO:33.

One embodiment of the present invention is an isolated protein that includes a flea EcR and/or USP protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea EcR and/or USP proteins of the present invention can be full-length proteins or any homolog of such proteins. An isolated protein of the present invention, including a homolog, can be identified in a straight-forward manner by the protein's ability to elicit an immune response against a flea EcR or USP protein or by the protein's EcR or USP activity. Examples of flea EcR and USP homolog proteins include flea EcR and USP proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against a flea EcR or USP protein, and/or of binding to an antibody directed against a flea EcR or USP protein. That is, when the homolog is administered to an animal as an immunogen, using techniques known to those skilled in the art, the animal will produce an immune response against at least one epitope of a natural flea EcR or USP protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids or at least about 50 amino acids in length. In one embodiment of the present invention a flea homolog protein has EcR or USP activity. Examples of methods to detect EcR and/or USP activity are disclosed herein. Flea EcR and USP homolog proteins can be the result of natural allelic variation or natural mutation. Flea EcR and USP protein homologs of the present invention can also be produced using techniques known in the art including, but not limited to, direct modifications to the protein or modifications to the gene encoding the protein using, for example, classic or recombinant DNA techniques to effect random or targeted mutagenesis.

Flea EcR and USP proteins of the present invention are encoded by flea EcR and USP nucleic acid molecules, respectively. As used herein, flea EcR and USP nucleic acid molecules include nucleic acid sequences related to natural flea EcR and USP genes, and, preferably, to *Ctenocephalides felis* EcR and USP genes. As used herein, flea EcR and USP genes include all regions such as regulatory regions that control production of flea EcR and USP proteins encoded by such genes (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a *C. felis* EcR gene that includes the nucleic acid sequence SEQ ID NO:5, SEQ ID NO:8, SEQ ID NO:13, and/or SEQ ID NO:16, as well as the complements of any of these nucleic acid sequences; and a *C. felis* USP gene that includes the nucleic acid sequence SEQ ID NO:26, SEQ ID NO:29, SEQ ID NO:32, and/or SEQ ID NO:35 as well as the complements of any of these nucleic acid sequences. These nucleic acid sequences are further described herein. For example, nucleic acid sequence SEQ ID NO:8 represents the deduced sequence of the coding strand of a *C. felis* cDNA (complementary DNA) denoted herein as *C. felis* EcR nucleic acid molecule nECR$_{1680}$, the production of which is disclosed in the Examples. Nucleic acid molecule nECR$_{1680}$ comprises an apparently full-length coding region. The complement of SEQ ID NO:8 (represented herein by SEQ ID NO:10) refers to the nucleic acid sequence of the strand complementary to the strand having SEQ ID NO:8, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:8 (as well as other nucleic acid and protein sequences presented herein) represents an apparent nucleic acid sequence of the nucleic acid molecule encoding an EcR protein of the present invention.

In another embodiment, an EcR gene or nucleic acid molecule can be an allelic variant that includes a similar but not identical sequence to SEQ ID NO:5, SEQ ID NO:7, SEQ ID NO:8, SEQ ID NO:10, SEQ ID NO:13, SEQ ID NO:15, SEQ ID NO:16, and/or SEQ ID NO:18, or any other *C. felis* EcR nucleic acid sequence cited herein and a USP gene or nucleic acid molecule can be an allelic variant that includes a similar but not identical sequence to SEQ ID NO:26, SEQ ID NO:28, SEQ ID NO:29, SEQ ID NO:31, SEQ ID NO:32, SEQ ID NO:34, SEQ ID NO:35, and/or SEQ ID NO:37, or any other *C. felis* USP nucleic acid sequence cited herein. For example, an allelic variant of a *C. felis* EcR gene including SEQ ID NO:8 is a gene that occurs at essentially the same locus (or loci) in the genome as the gene including SEQ ID NO:8, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea such as *C. felis*, since the genome is diploid, and sexual reproduction will result in the reassortment of alleles.

In one embodiment of the present invention, isolated EcR and USP proteins are encoded by nucleic acid molecules that hybridize under stringent hybridization conditions to genes encoding flea EcR and USP proteins respectively. The minimal size of EcR and USP proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea EcR or USP nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea EcR or USP protein is typically at least about 12 to about 15 nucleotides in length if the nucleic acid molecule is GC-rich and at least about 15 to about 17 bases in length if it is AT-rich. The minimal size of a nucleic acid molecule used to encode an EcR or USP protein homolog of the present invention is from about 12 to about 18 nucleotides in length. Thus, the minimal size of EcR or USP protein homologs of the present invention is from about 4 to about 6 amino acids in length.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al.

For nucleic acid molecules smaller than about 50 nucleotides, hybrid stability is defined by the dissociation temperature ($T_d$) which is defined as the temperature at which 50% of the duplexes dissociate. For these smaller molecules, the stability at a standard ionic strength is defined by the following equation: $T_d=4(G+C)+2(A+T)$.

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with greater than a specified % base pair mismatch will hybridize. Stringent hybridization conditions are commonly understood by those skilled in the art to be those experimental conditions that will allow about 30% base pair mismatch (i.e., about 70% identity). Because one skilled in the art can easily determine whether a given nucleic acid molecule to be tested is less than or greater than about 50 nucleotides, and can therefore choose the appropriate formula for determining hybridization conditions, he or she can whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *C. felis* nucleic acid molecule of about 150 bp in length, the following conditions could preferably be used. The average G+C content of *C. felis* DNA is about 43%. The unknown nucleic acid molecules would be attached to a support membrane, and the 150 bp probe would be labeled, e.g. with a radioactive tag. The hybridization reaction could be carried out in a solution comprising 2× SSC and 0% formamide, at a temperature of about 37° C. (low stringency conditions). Solutions of differing concentrations of SSC can be made by one of skill in the art by diluting a stock solution of 20× SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base pair mismatch. For example, in a wash solution comprising 1× SSC and 0% formamide, the $T_m$ of perfect hybrids would be about 82° C.:81.5° C.+16.6 log (0.15M)+(0.41×43)−(500/150)−(0.61×0)=82° C.

Thus, to achieve hybridization with nucleic acid molecules having about 30% base pair mismatch, hybridization washes would be carried out at a temperature of about 52° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 52° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the GAP program with pair-wise comparisons within the program GCG™ Version 9.0-UNIX, hereinafter referred to as default parameters.

Another embodiment of the present invention includes flea EcR and USP proteins. A preferred flea EcR protein includes a protein encoded by a nucleic acid molecule which is at least about 34 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:7, SEQ ID NO:10, SEQ ID NO:15, and SEQ ID NO:18.

A preferred flea USP protein includes a protein encoded by a nucleic acid molecule which is at least about 30 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:28, SEQ ID NO:31, SEQ ID NO:34, and SEQ ID NO:37.

Another embodiment of the present invention includes a flea EcR protein encoded by a nucleic acid molecule comprising at least about 34 base pairs, wherein said nucleic acid molecule hybridizes, in a solution comprising 1×SSC and 0% formamide, at a temperature of about 52° C., to an isolated nucleic acid molecule selected from the group consisting of SEQ ID NO:7, SEQ ID NO:10, SEQ ID NO:15, and SEQ ID NO:18.

Another embodiment of the present invention includes a flea USP protein encoded by a nucleic acid molecule comprising at least about 30 base pairs, wherein said nucleic acid molecule hybridizes, in a solution comprising 1× SSC and 0% formamide, at a temperature of about 52° C., to an isolated nucleic acid molecule selected from the group consisting of SEQ ID NO:28, SEQ ID NO:31, SEQ ID NO:34, and SEQ ID NO:37.

Another preferred flea EcR protein of the present invention includes a protein which is encoded by a nucleic acid molecule that is preferably about 70% identical, more preferably about 75% identical, more preferably about 80% identical, more preferably about 85% identical, more preferably about 90% identical, and even more preferably about 95% identical to a nucleic acid molecule having the nucleic acid sequence SEQ ID NO:5, SEQ ID NO:8, SEQ ID NO:13, and/or SEQ ID NO:16; also preferred are fragments (i.e. portions) of such proteins encoded by nucleic acid molecules which are at least about 30 nucleotides. Percent identity as used herein is determined using the Compare function by maximum matching within the program DNAsis Version 2.1 using default parameters.

Another preferred flea USP protein of the present invention includes a protein which is encoded by a nucleic acid molecule that is preferably about 70% identical, more preferably about 75% identical, more preferably about 80% identical, more preferably about 85% identical, more preferably about 90% identical, and even more preferably about 95% identical to a nucleic acid molecule having the nucleic acid sequence SEQ ID NO:26, SEQ ID NO:29, SEQ ID NO:32, and/or SEQ ID NO:35; also preferred are fragments (i.e. portions) of such proteins encoded by nucleic acid molecules which are at least about 34 nucleotides. Percent identity as used herein is determined using the Compare function by maximum matching within the program DNAsis Version 2.1 using default parameters.

Additional preferred flea EcR proteins of the present invention include proteins having the amino acid sequence SEQ ID NO:6 or SEQ ID NO:14, and proteins comprising homologs of a protein having the amino acid sequence SEQ ID NO:6 or SEQ ID NO:14, wherein such a homolog comprises at least one epitope that elicits an immune response against a protein having an amino acid sequence SEQ ID NO:6 or SEQ ID NO:14. Likewise, also preferred are proteins encoded by nucleic acid molecules comprising nucleic acid sequence SEQ ID NO:5, SEQ ID NO:8, SEQ ID NO:13, and/or SEQ ID NO:16, or by homologs thereof.

Additional preferred flea USP proteins of the present invention include proteins having the amino acid sequence SEQ ID NO:27 or SEQ ID NO:33, and proteins comprising homologs of a protein having the amino acid sequence SEQ ID NO:27 or SEQ ID NO:33, wherein such a homolog comprises at least one epitope that elicits an immune response against a protein having an amino acid sequence SEQ ID NO:27 or SEQ ID NO:33. Likewise, also preferred are proteins encoded by nucleic acid molecules comprising nucleic acid sequence SEQ ID NO:26, SEQ ID NO:29, SEQ ID NO:32, and/or SEQ ID NO:35, or by homologs thereof.

A preferred isolated protein of the present invention is a protein encoded by at least one of the following nucleic acid molecules: $nECR_{2822}$, $nECR_{1680}$, $nECR_{666}$, $nECR_{4148}$, $nECR_{1683}$, $nECR_{612}$, $nUSP_{1749}$, $nUSP_{1344}$, $nUSP_{1975}$, $nUSP_{1422}$, $nUSP_{776}$, or $nUSP_{943}$ or allelic variants of any of these nucleic acid molecules. Another preferred isolated protein is encoded by a nucleic acid molecule having nucleic acid sequence SEQ ID NO:5, SEQ ID NO:8, SEQ ID NO:13, SEQ ID NO:16, SEQ ID NO:26, SEQ ID NO:29, SEQ ID NO:32, and/or SEQ ID NO:35; or a protein encoded by an allelic variant of any of these listed nucleic acid molecule.

Translation of SEQ ID NO:8, the coding strand of $nECR_{1680}$, yields a protein of about 560 amino acids, denoted herein as $PECR_{560}$, the amino acid sequence of which is presented in SEQ ID NO:6, assuming a first in-frame codon extending from nucleotide 1 to nucleotide 3 of SEQ ID NO:8. Sequence analysis of SEQ ID NO:6 revealed a putative DNA binding domain spanning from amino acid residue 142 to residue 207 of SEQ ID NO:6, designated SEQ ID NO:64. Sequence analysis also revealed a putative ecdysone (i.e., ligand) binding domain spanning from amino acid residue 309 to residue 527 of SEQ ID NO:6, designated SEQ ID NO:65.

Translation of SEQ ID NO:16, the coding strand of $nECR_{1683}$, yields a protein of about 561 amino acids, denoted herein as $PECR_{561}$, the amino acid sequence of which is presented in SEQ ID NO:14, assuming a first in-frame codon extending from nucleotide 1 to nucleotide 3 of SEQ ID NO:16. Sequence analysis of SEQ ID NO:14 revealed a putative EcR DNA binding domain spanning from amino acid residue 143 to residue 208 of SEQ ID NO:14, designated SEQ ID NO:66. Sequence analysis also revealed a putative ligand binding domain spanning from amino acid residue 310 to residue 528 of SEQ ID NO:14, designated SEQ ID NO:67.

It is within the scope of the invention that the DNA binding domains represented by SEQ ID NO:64 and SEQ ID NO:66 represent protein domains capable of binding to an ecdysone response element and the ligand binding domains represented by SEQ ID NO:65 and SEQ ID NO:67 represent protein domains capable of binding to ecdysone.

Translation of SEQ ID NO:29, the coding strand of $nUSP_{1344}$, yields a protein of about 448 amino acids, denoted herein as $PUSP_{448}$, the amino acid sequence of which is presented in SEQ ID NO:27, assuming a first in-frame codon extending from nucleotide 1 to nucleotide 3 of SEQ ID NO:29. Sequence analysis of SEQ ID NO:27 revealed a putative USP DNA binding domain spanning from amino acid residue 89 to residue 154 of SEQ ID NO:27, designated SEQ ID NO:68. Sequence analysis also revealed a putative ligand binding domain spanning from amino acid residue 178 to residue 448 of SEQ ID NO:27, designated SEQ ID NO:69.

Translation of SEQ ID NO:35, the coding strand of $nUSP_{1422}$, yields a protein of about 474 amino acids, denoted herein as $PUSP_{474}$, the amino acid sequence of which is presented in SEQ ID NO:33, assuming a first in-frame codon extending from nucleotide 1 to nucleotide 3 of SEQ ID NO:35. Sequence analysis of SEQ ID NO:33 revealed a putative DNA binding domain spanning from amino acid residue 115 to residue 180 of SEQ ID NO:33, designated SEQ ID NO:70. Sequence analysis also revealed a putative EcR (i.e., ligand) binding domain spanning from amino acid residue 204 to residue 474 of SEQ ID NO:33, designated SEQ ID NO:71.

While not being bound by theory, it is believed that the putative DNA binding domains represented by SEQ ID NO:68 and SEQ ID NO:70 and the putative ligand binding domains represented by SEQ ID NO:69 and SEQ ID NO:71 represent domains capable of affecting the binding of ecdysone receptor to ecdysone and thereby affecting DNA transcription.

Preferred proteins of the present invention include proteins that are at least about 70%, preferably at least about 80%, more preferably at least about 85%, even more preferably at least about 90%, even more preferably at least about 95%, and even more preferably about 100% identical to $PECR_{560}$, $PECR_{561}$, $PUSP_{448}$, or $PUSP_{474}$. Additionally preferred are proteins encoded by allelic variants of a nucleic acid molecules encoding proteins $PECR_{560}$, $PECR_{561}$, $PUSP_{448}$, or $PUSP_{474}$. Also preferred are fragments thereof having at least about 35 amino acid residues.

Other preferred EcR proteins of the present invention include proteins having amino acid sequences that are at least about 70%, preferably at least about 80%, more preferably at least about 85%, even more preferably at least about 90%, even more preferably at least about 95%, and even more preferably about 100% identical to amino acid sequence SEQ ID NO:6 or SEQ ID NO:14. More preferred are EcR proteins comprising amino acid sequences SEQ ID NO:6 or SEQ ID NO:14; and EcR proteins encoded by allelic variants of nucleic acid molecules encoding EcR proteins having amino acid sequences SEQ ID NO:6 or SEQ ID NO:14. Also preferred are fragments thereof having at least about 35 amino acid residues.

In one embodiment of the present invention, *C. felis* EcR proteins comprise amino acid sequence SEQ ID NO:6 or SEQ ID NO:14 (including, but not limited to, the proteins consisting of amino acid sequence SEQ ID NO:6 or SEQ ID NO:14, fusion proteins and multivalent proteins), and proteins encoded by allelic variants of nucleic acid molecules encoding proteins having amino acid sequence SEQ ID NO:6 or SEQ ID NO:14. In another embodiment, *C. felis* USP proteins of the present invention comprise amino acid sequence SEQ ID NO:27 or SEQ ID NO:33 (including, but not limited to, the proteins consisting of amino acid sequence SEQ ID NO:27 or SEQ ID NO:33, fusion proteins and multivalent proteins), and proteins encoded by allelic variants of nucleic acid molecules encoding proteins having amino acid sequence SEQ ID NO:27 or SEQ ID NO:33.

In one embodiment, a preferred flea EcR protein comprises an amino acid sequence of at least about 35 amino acids, preferably at least about 50 amino acids, more preferably at least about 100 amino acids, more preferably at least about 200 amino acids, more preferably at least about 250 amino acids, more preferably at least about 300 amino acids, more preferably at least about 350 amino acids, more preferably at least about 400 amino acids, more preferably at least about 450 amino acids, more preferably at least about 500 amino acids, even more preferably at least about 550 amino acids and a preferred flea USP protein comprises an amino acid sequence of at least about 35 amino acids, preferably at least about 50 amino acids, more preferably at least about 100 amino acids, more preferably at least about 150 amino acids, more preferably at least about 200 amino acids, more preferably at least about 250 amino acids, more preferably at least about 300 amino acids, more preferably at least about 350 amino acids, more preferably at least about 400 amino acids, more preferably at least about 450 amino acids, even more preferably at least about 475 amino acids. In another embodiment, preferred fleaEcR and USP proteins comprise full-length proteins, i.e., proteins encoded by full-length coding regions.

In another embodiment, a preferred flea EcR protein comprises an isolated flea EcR protein selected from the group consisting of: (a) a protein comprising an amino acid sequence that is at least about 70% identical to an amino acid sequence selected from the group consisting of SEQ ID NO:6 and SEQ ID NO:14, wherein said protein is at least about 71 amino acids residues in length; (b) a protein consisting of an amino acid sequence selected from the group consisting of SEQ ID NO:64, SEQ ID NO:65, and fragments thereof, wherein said protein has at least a portion of an EcRE binding domain; (c) a protein consisting of an amino acid sequence selected from the group consisting of SEQ ID NO:66, SEQ ID NO:67, and fragments thereof, wherein said protein has at least a portion of an EcR ligand binding domain or (d) a protein encoded by an allelic variant of a nucleic acid molecule which encodes any protein of (a), (b) or (c).

In another embodiment, a preferred flea USP protein comprises an isolated flea ultraspiracle protein selected from the group consisting of: (a) a protein comprising an amino acid sequence that is at least about 70% identical to an amino acid sequence selected from the group consisting of SEQ ID NO:27 and SEQ ID NO:33, wherein said protein is at least about 72 amino acids residues in length; (b) a protein consisting of an amino acid sequence selected from the group consisting of SEQ ID NO:68, SEQ ID NO:69, SEQ ID NO:70, SEQ ID NO:71, and fragments thereof, wherein said protein has at least a portion of a USP protein that is capable of affecting binding of EcR to ecdysone; or (c) a protein encoded by an allelic variant of a nucleic acid molecule which encodes any protein of (a) or (b). As used herein, the term "capable of affecting" the binding of ecdysone receptor to ecdysone means the ability of USP to act as a heterodimeric binding partner with EcR, i.e. to assist EcR in the binding of ecdysone, preferably to promote, improve and/or enhance high affinity binding between EcR and ecdysone.

One of skill in the art will understand that a DNA or protein fragment of the present invention includes a portion of a larger nucleic acid molecule or protein, respectively. Preferably, DNA fragments including the DNA binding, or ligand binding domains, of EcR can be isolated from SEQ ID NO:5 and/or SEQ ID NO:13 and DNA fragments including the DNA binding, or ligand binding domains, of USP can be isolated from SEQ ID NO:26 and/or SEQ ID NO:32. Preferably, protein fragments including the DNA binding, or ligand binding domains, of EcR can be isolated from SEQ ID NO:6 and/or SEQ ID NO:14 and protein fragments including the DNA binding, or ligand binding domains, of USP can be isolated from SEQ ID NO:27 and/or SEQ ID NO:33.

One of skill in the art will also understand that fragments including the active domains of EcR, or USP, can vary and extend beyond those particular nucleic acid or amino acid regions defined herein. Such active domains can vary in length by 1 amino acid to about 50 amino acids. Nucleic acids or amino acids essential to an active domain can be identified using standard protein or DNA binding assays known to those of skill in the art to determine the ability of an active domain to bind to its ligand, e.g. EcRE, ecdysone or EcR.

A fragment of an EcR and/or USP protein of the present invention preferably comprises at least about 5 amino acids, more preferably at least about 10 amino acids, more preferably at least about 15 amino acids, more preferably at least about 20 amino acids, more preferably at least about 25 amino acids, more preferably at least about 30 amino acids, more preferably at least about 35 amino acids, more preferably at least about 40 amino acids, more preferably at least about 45 amino acids, more preferably at least about 50 amino acids, more preferably at least about 55 amino acids, more preferably at least about 60 amino acids, more preferably at least about 65 amino acids, more preferably at least about 70 amino acids, more preferably at least about 75 amino acids, more preferably at least about 80 amino acids, more preferably at least about 85 amino acids, more preferably at least about 90 amino acids, more preferably at least about 95 amino acids, and even more preferably at least about 100 amino acids in length.

Additional preferred fragments of the present invention can include SEQ ID NO:64, SEQ ID NO:65, SEQ ID NO:66, SEQ ID NO:67, SEQ ID NO:68, SEQ ID NO:69, SEQ ID NO:70, and SEQ ID NO:71, as well as fragments of SEQ ID NO:6, SEQ ID NO:14, SEQ ID NO:27, and SEQ ID NO:33 that are not SEQ ID NO:64, SEQ ID NO:65, SEQ ID NO:66, SEQ ID NO:67, SEQ ID NO:68, SEQ ID NO:69, SEQ ID NO:70, and SEQ ID NO:71.

Additional preferred EcR and USP proteins of the present invention include proteins encoded by nucleic acid molecules comprising at least a portion of $nECR_{2822}$, $nECR_{1680}$, $nECR_{4148}$, $nECR_{1683}$, $nECR_{612}$ $nUSP_{1749}$, $nUSP_{1344}$, $nUSP_{1975}$, $nUSP_{1422}$, $nUSP_{776}$, and $nUSP_{943}$, as well as EcR and USP proteins encoded by allelic variants of such nucleic acid molecules.

Also preferred are EcR proteins encoded by nucleic acid molecules having nucleic acid sequences comprising at least a portion of SEQ ID NO:5, SEQ ID NO:8, SEQ ID NO:13, and/or SEQ ID NO:16, as well as allelic variants of these nucleic acid molecules.

Also preferred are USP proteins encoded by nucleic acid molecules having nucleic acid sequences comprising at least a portion of SEQ ID NO:26, SEQ ID NO:29, SEQ ID NO:32, and/or SEQ ID NO:35, as well as allelic variants of these nucleic acid molecules.

In another embodiment, a preferred flea EcR protein of the present invention is encoded by a nucleic acid molecule comprising at least about 25 nucleotides, more preferably at least about 50 nucleotides, more preferably at least about 150 nucleotides, more preferably at least about 350 nucleotides, more preferably at least about 450 nucleotides, more preferably at least about 550 nucleotides, more preferably at least about 650 nucleotides, more preferably at least about 750 nucleotides, more preferably at least about 1000 nucleotides, more preferably at least about 1500 nucleotides, more preferably at least about 2000 nucleotides, more preferably at least about 2500 nucleotides, more preferably at least about 2800 nucleotides, more preferably at least about 3000 nucleotides, more preferably at least about 4000 nucleotides, and even more preferably at least about 4150 nucleotides in length, and a preferred flea USP protein of the present invention is encoded by a nucleic acid molecule comprising a coding region of at least about 25 nucleotides, more preferably at least about 50 nucleotides, more preferably at least about 100 nucleotides, more preferably at least about 150 nucleotides, more preferably at least about 250 nucleotides, more preferably at least about 500 nucleotides, more preferably at least about 800 nucleotides, more preferably at least about 1000 nucleotides, more preferably at least about 1250 nucleotides, more preferably at least about 1400 nucleotides, more preferably at least about 1750 nucleotides, more preferably at least about 1900 nucleotides, even more preferably at least about 1975 nucleotides in length. Within this embodiment is an EcR protein encoded by at least a portion of $nECR_{2822}$ or $nECR_{4148}$ or by an allelic variant of either of these nucleic acid molecules and a USP protein encoded by at least a portion of nUSP$_{1749}$ or nUSP$_{1975}$ or by an allelic variant of either of these nucleic acid molecules. In yet another embodiment, preferred flea EcR and USP proteins of the present invention are encoded by nucleic acid molecules comprising apparently full-length EcR or USP coding regions respectively, i.e., nucleic acid molecules encoding an apparently full-length EcR or USP proteins.

Preferred arthropod EcR and USP proteins of the present invention are compounds that can be used to develop inhibitors that, Suitable fleas to target include any flea that is essentially incapable of causing disease in an animal administered an inhibitor of the present invention. As such, fleas to target includes any flea that produces a protein that can be targeted by an inhibitory compound that otherwise inhibits flea EcR or USP function (e.g., a compound that binds to flea EcR or USP thereby blocking flea development and/or migration regulatory pathways), thereby resulting in the decreased ability of the parasite to cause disease in an animal.

One embodiment of a flea EcR and/or USP protein of the present invention is a fusion protein that includes a flea EcR and/or USP protein-containing domain attached to one or more fusion segments. Suitable fusion segments for use with the present invention include, but are not limited to, segments that can: enhance a protein's stability; act as an immunopotentiator to enhance an immune response against a flea EcR and/or USP protein; and/or assist in purification of a flea EcR and/or USP protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea EcR-containing and/or USP-containing domain of the protein and can be susceptible to cleavage in order to enable straight-forward recovery of a flea EcR and/or USP protein. Fusion proteins are preferably produced by culturing a recombinant cell transformed with a fusion nucleic acid molecule that encodes a protein including the fusion segment attached to either the carboxyl and/or amino terminal end of an EcR-containing and/or USP-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of flea EcR and/or USP proteins of the present invention. As used herein, a mimetope of a flea EcR and/or USP protein of the present invention refers to any compound that is able to mimic the activity of such an EcR and/or USP protein, often because the mimetope has a structure that mimics the particular EcR and/or USP protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea EcR and/or USP nucleic acid molecule. The identifying characteristics of such nucleic acid molecules are heretofore described. A nucleic acid molecule of the present invention can include an isolated natural flea EcR and/or USP gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of an EcR and/or USP nucleic acid molecule of the present invention is from about 12 to about 18 nucleotides in length. Suitable and preferred fleas from which to isolate nucleic acid molecules of the present invention are disclosed herein. Particularly preferred EcR and/or USP nucleic acid molecules include *C. felis*

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea EcR and/or USP nucleic acid molecules of the present invention, or homologs thereof, can be isolated from a natural source or produced using recombinant DNA technology (e.g., polymerase chain reaction (PCR) amplification or cloning) or chemical synthesis. Isolated flea EcR and/or USP nucleic acid molecules, and homologs thereof, can include, for example, natural allelic variants and nucleic acid molecules modified by nucleotide insertions, deletions, substitutions, and/or inversions in a manner such that the modifications do not substantially interfere with the nucleic acid molecule's ability to encode an EcR and/or USP protein of the present invention.

A flea EcR and/or USP nucleic acid molecule homolog can be produced using a number of methods known to those skilled in the art, see, for example, Sambrook et al., 1989, *Molecular Cloning. A Laboratory Manual*, Cold Spring Harbor Labs Press; Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologs can be selected by hybridization with flea EcR or USP nucleic acid molecules or by screening the function of a protein encoded by the nucleic acid molecule (e.g., ability to elicit an immune response against at least one epitope of a flea EcR or USP protein or to effect EcR or USP activity).

An isolated nucleic acid molecule of the present invention can include a nucleic acid sequence that encodes at least one flea EcR or USP protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea EcR or USP protein.

A preferred nucleic acid molecule of the present invention, when administered to an animal, is capable of protecting that animal from flea infestation. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an EcR or USP protein of the present invention), the nucleic acid molecule being delivered to the animal, for example, by direct injection (i.e, as a genetic vaccine) or in a vehicle such as a recombinant virus vaccine or a recombinant cell vaccine.

In one embodiment of the present invention, a preferred flea EcR nucleic acid molecule includes an isolated nucleic acid molecule which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:7, SEQ ID NO:10, SEQ ID NO:15, and SEQ ID NO:18.

In one embodiment of the present invention, a preferred flea USP nucleic acid molecule includes an isolated nucleic acid molecule which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:28, SEQ ID NO:31, SEQ ID NO:34, and SEQ ID NO:37.

Another embodiment of the present invention includes a nucleic acid molecule, wherein said nucleic acid molecule hybridizes, in a solution comprising 1×SSC and 0% formamide, at a temperature of about 52° C., to an isolated nucleic acid molecule selected from the group consisting of SEQ ID NO:5, SEQ ID NO:7, SEQ ID NO:8, SEQ ID NO:10, SEQ ID NO:13, SEQ ID NO:15, SEQ ID NO:16, SEQ ID NO:18, SEQ ID NO:26, SEQ ID NO:28, SEQ ID NO:29, SEQ ID NO:31, SEQ ID NO:32, SEQ ID NO:34, SEQ ID NO:35 and SEQ ID NO:37. Additional preferred nucleic acid molecules of the present invention include oligonucleotides of an isolated nucleic acid molecule, wherein said nucleic acid molecule hybridizes, in a solution comprising 1×SSC and 0% formamide, at a temperature of about 52° C., to an isolated nucleic acid molecule selected from the group consisting of SEQ ID NO:5, SEQ ID NO:7, SEQ ID NO:8, SEQ ID NO:10, SEQ ID NO:13, SEQ ID NO:15, SEQ ID NO:16, SEQ ID NO:18, SEQ ID NO:26, SEQ ID NO:28, SEQ ID NO:29, SEQ ID NO:31, SEQ ID NO:32, SEQ ID NO:34, SEQ ID NO:35 and SEQ ID NO:37, wherein said oligonucleotide comprises at least about 30 nucleotides.

Additional preferred flea EcR nucleic acid molecules of the present invention include nucleic acid molecules comprising a nucleic acid sequence that is preferably at least about 70%, more preferably at least about 75%, more preferably at least about 80% more preferably at least about 85%, more preferably at least about 90%, and even more preferably at least about 95% identical to a nucleic acid sequence selected from the group consisting of SEQ ID NO:5, SEQ ID NO:7, SEQ ID NO:8, SEQ ID NO:10, SEQ ID NO:13, SEQ ID NO:15, SEQ ID NO:16, and/or SEQ ID NO:18. Also preferred are oligonucleotides of any of such nucleic acid molecules, particularly those that are at least about 34 nucleotides. Percent identity may be determined using the program GCG Version 9.0-UNIX using default parameters.

Additional preferred flea USP nucleic acid molecules of the present invention include nucleic acid molecules comprising a nucleic acid sequence that is preferably at least about 70%, more preferably at least about 75%, more preferably at least about 80% more preferably at least about 85%, more preferably at least about 90%, and even more preferably at least about 95% identical to a nucleic acid sequence selected from the group consisting of SEQ ID NO:26, SEQ ID NO:28, SEQ ID NO:29, SEQ ID NO:31, SEQ ID NO:32, SEQ ID NO:34, SEQ ID NO:35, and/or SEQ ID NO:37. Also preferred are oligonucleotides of any of such nucleic acid molecules, particularly those that are at least about 30 nucleotides. Percent identity may be determined using the program GCG Version 9.0-UNIX using default parameters.

One embodiment of the present invention is a nucleic acid molecule comprising all or part of nucleic acid molecules $nECR_{2822}$, $nECR_{1680}$, $nECR_{666}$, $nECR_{4148}$, $nECR_{1683}$, $nECR_{612}$ $nUSP_{1749}$, $nUSP_{1344}$, $nUSP_{1975}$, $nUSP_{1422}$, $nUSP_{776}$, and $nUSP_{943}$, or allelic variants of these nucleic acid molecules. Another preferred nucleic acid molecule of the present invention includes at least a portion of nucleic acid sequence SEQ ID NO:5, SEQ ID NO:8, SEQ ID NO:13, SEQ ID NO:16, SEQ ID NO:26, SEQ ID NO:29, SEQ ID NO:32, and/or SEQ ID NO:35, as well as allelic variants of nucleic acid molecules having these nucleic acid sequences and homologs of nucleic acid molecules having these nucleic acid sequences; preferably such a homolog encodes or is complementary to a nucleic acid molecule that encodes at least one epitope that elicits an immune response against a protein having an amino acid sequence SEQ ID NO:6, SEQ ID NO:14, SEQ ID NO:27 or SEQ ID NO:33. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, an EcR nucleic acid molecule of the present invention encodes a protein that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to $PECR_{560}$ and/or $PECR_{561}$. In another embodiment, a USP nucleic acid molecule of the present invention encodes a protein that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to $PUSP_{448}$ and/or $PUSP_{474}$.

In another embodiment, an EcR nucleic acid molecule of the present invention encodes a protein having an amino acid sequence that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to SEQ ID NO:6 or SEQ ID NO:14. The present invention also includes an EcR nucleic acid molecule encoding a protein having at least a portion of SEQ ID NO:6, and/or SEQ ID NO:14, as well as allelic variants of an EcR nucleic acid molecule encoding a protein having these sequences, including nucleic acid molecules that have been modified to accommodate codon usage properties of the cells in which such nucleic acid molecules are to be expressed.

In another embodiment, a USP nucleic acid molecule of the present invention encodes a protein having an amino acid sequence that is at least about 70%, preferably at least about 75%, more preferably at least about 80%, even more preferably at least about 85%, even more preferably at least about 90%, even more preferably at least about 95%, even more preferably at least about 98%, and even more preferably at least about 100% identical to SEQ ID NO:27 or SEQ ID NO:33. The present invention also includes a USP nucleic acid molecule encoding a protein having at least a portion of SEQ ID NO:27, and/or SEQ ID NO:33, as well as allelic variants of a USP nucleic acid molecule encoding a protein having these sequences, including nucleic acid molecules that have been modified to accommodate codon usage properties of the cells in which such nucleic acid molecules are to be expressed.

In another embodiment, a preferred flea EcR nucleic acid molecule encodes an EcR protein comprising at least about 35 amino acids, preferably at least about 50 amino acids, more preferably at least about 100 amino acids, more preferably at least about 200 amino acids, more preferably at least about 300 amino acids, more preferably at least about 400 amino acids, more preferably at least about 500 amino acids, even more preferably at least about 560 amino acids in length.

In another embodiment, a preferred flea USP nucleic acid molecule encodes a USP protein comprising at least about at least about 35 amino acids, preferably at least about 50 amino acids, more preferably at least about 100 amino acids, more preferably at least about 200 amino acids, more preferably at least about 300 amino acids, more preferably at least about 400 amino acids, more preferably at least about 450 amino acids, even more preferably at least about 475 amino acids in length.

In another embodiment, a preferred flea EcR nucleic acid molecule comprises a nucleic acid sequence that encodes at least a portion of a flea EcR protein that is capable of binding to an ecdysone response element. Preferably, such nucleic acid molecule encodes a protein having SEQ ID NO:64 and/or SEQ ID NO:65. A preferred flea EcR protein also comprises at least a portion of a flea EcR protein that is capable of binding to ecdysone. Preferably, such nucleic acid molecule encodes a protein having SEQ ID NO:66 and/or SEQ ID NO:67.

In another embodiment, a preferred flea USP nucleic acid molecule comprises a nucleic acid sequence that encodes at least a portion of a flea USP DNA binding domain. Preferably, such nucleic acid molecule encodes a protein having SEQ ID NO:68 and/or SEQ ID NO:69. A preferred flea USP protein also comprises at least a portion of a flea USP ligand binding domain. Preferably, such nucleic acid molecule encodes a protein having SEQ ID NO:70 and/or SEQ ID NO:71.

In another embodiment, a preferred flea EcR nucleic acid molecule of the present invention comprises an apparently full-length EcR coding region, i.e., the preferred nucleic acid molecule encodes an apparently full-length EcR protein.

In yet another embodiment, a preferred flea USP nucleic acid molecule of the present invention comprises an apparently full-length USP coding region, i.e., the preferred nucleic acid molecule encodes an apparently full-length USP protein.

Knowing the nucleic acid sequences of certain flea EcR and/or USP nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea EcR and/or USP nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include flea $1^{st}$ instar larvae; $3^{rd}$ instar larvae, wandering larvae, prepupal larvae, pupae and whole adult flea cDNA libraries as well as genomic DNA libraries. Similarly, preferred DNA sources to screen or from which to amplify nucleic acid molecules include flea prepupal cDNA, adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising C. felis EcR and/or USP nucleic acid molecules or other flea EcR and/or USP nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 200 nucleotides, more preferably about 150 nucleotides, more preferably about 100 nucleotides and even more preferably about 50 nucleotides. The present invention includes oligonucleotides that can be used as, for example, probes to identify nucleic acid molecules, primers to produce nucleic acid molecules, or therapeutic reagents to inhibit flea EcR and/or USP protein production or activity (e.g., as antisensetriplex formationribozymeand/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea EcR and/or USP nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7 lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nECR_{2822}$, $nECR_{1680}$, $nECR_{4148}$, $nECR_{1683}$, $nECR_{612}$, $nUSP_{1749}$, $nUSP_{1344}$, $nUSP_{1975}$, $nUSP_{1422}$, $nUSP_{776}$, and $nUSP_{943}$.

Recombinant molecules of the present invention may also (a) contain secretory signals (i.e., signal segment nucleic acid sequences) to enable an expressed flea protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include *C. felis* EcR and USP nucleic acid molecules disclosed herein. Particularly preferred nucleic acid molecules with which to transform a cell include $nECR_{2822}$, $nECR_{1680}$, $nECR_{4148}$, $nECR_{1683}$, $nECR_{612}$, $nUSP_{1749}$, $nUSP_{1344}$, $nUSP_{1975}$, $nUSP_{1422}$, $nUSP_{776}$, and $nUSP_{943}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing EcR and/or USP proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_{\pi}3987$ and SR-11 $_{\pi}4072$; *Spodoptera frugiperda*; *Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea EcR and/or USP nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea EcR and/or USP proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea EcR and/or USP protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea EcR and/or USP protein of the present invention or a mimetope thereof (e.g., anti- *C. felis* EcR or USP antibodies). As used herein, the term "selectively binds to" an EcR and/or USP protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-EcR or anti-USP antibody of the present invention preferably selectively binds to a flea EcR or USP protein respectively in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce EcR and/or USP proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from flea infestation. Therapeutic compositions of the present invention include at least one of the following protective compounds: an isolated antibody that selectively binds to a flea EcR or USP protein, or inhibitors of EcR and/or USP function identified by their ability to bind to a flea EcR and/or USP protein. Other protective compounds include for example, antisense-, triplex formation- ribozyme- and/or RNA drug-based technologies. As used herein, a protective compound refers to a compound that, when administered to an animal in an effective manner, is able to treat, ameliorate, and/or prevent flea infestation. Preferred fleas to target are heretofore disclosed. Examples of antibodies and inhibitors of the present invention are disclosed herein.

Additional therapeutic compositions of the present invention include a protective compound derived from a protein selected from the group consisting of: (a) an isolated flea ecdysone receptor protein selected from the group consisting of: (i) a protein comprising an amino acid sequence that is at least about 70% identical to an amino acid sequence selected from the group consisting of SEQ ID NO:6 and SEQ ID NO:14, wherein said protein is at least about 71 amino acid residues in length; (ii) a protein consisting of an amino acid sequence selected from the group consisting of SEQ ID NO:64, SEQ ID NO:66, and fragments thereof, wherein said protein has at least a portion of an ecdysone receptor DNA binding site; (iii) a protein consisting of an amino acid sequence selected from the group consisting of SEQ ID NO:65, SEQ ID NO:67, and fragments thereof, wherein said protein has at least a portion of an ecdysone receptor ligand binding site; and (iv) a protein encoded by an allelic variant of a nucleic acid molecule which encodes any protein of (i), (ii), or (iii); and (b) an isolated flea ultraspiracle protein selected from the group consisting of: (i) a protein comprising an amino acid sequence that is at least about 70% identical to an amino acid sequence selected from the group consisting of SEQ ID NO:27 and SEQ ID NO:33, wherein said protein is at least about 72 amino acid residues in length; (ii) a protein consisting of an amino acid sequence selected from the group consisting of SEQ ID NO:68, SEQ ID NO:69, SEQ ID NO:70, SEQ ID NO:71, and fragments thereof, wherein said protein has at least a portion of an ultraspiracle protein that is capable of affecting binding of ecdysone receptor to ecdysone; and (iii) a protein encoded by an allelic variant of a nucleic acid molecule which encodes any protein of (i) or (ii); wherein said protective compound inhibits the binding between ecdysone receptor and ecdysone. As used herein, the term "derived from" refers to a natural EcR or USP DNA or protein of the present invention, a portion of a natural EcR or USP DNA or protein of the present invention, as well as, a compound designed using an EcR or USP DNA or protein of the present invention, such as, for example, proteins encoded by recombinant DNA, peptides, antibodies or small molecule inhibitors.

Suitable inhibitors of EcR and/or USP activity are compounds that inhibit EcR and/or USP protein activity, usually by binding to or otherwise interacting with or otherwise modifying the EcR and/or USP active site. EcR and/or USP inhibitors can also interact with other regions of the EcR and/or USP protein to inhibit EcR and/or USP activity, for example, by allosteric interaction. Inhibitors of EcR and/or USP are usually relatively small compounds and as such differ from anti-EcR and anti-USP antibodies. Preferably, an EcR and/or USP inhibitor of the present invention is identified by its ability to bind to, or otherwise interact with, a flea EcR and/or USP protein, thereby inhibiting the activity of the flea EcR and/or USP.

EcR and/or USP inhibitors can be used directly as compounds in compositions of the present invention to treat animals as long as such compounds are not harmful to host animals being treated. EcR and/or USP inhibitors can also be used to identify preferred types of flea EcR and/or USP to target using compositions of the present invention, for example by affinity chromatography. Preferred EcR and/or USP inhibitors of the present invention include, but are not limited to, flea EcR and/or USP substrate analogs, and other molecules that bind to a flea EcR and/or USP (e.g., to an allosteric site) in such a manner that EcR and/or USP activity of the flea EcR and/or USP is inhibited. An EcR and/or USP substrate analog refers to a compound that interacts with (e.g., binds to, associates with, modifies) the active site of an EcR and/or USP protein. A preferred EcR and/or USP substrate analog inhibits EcR and/or USP activity. EcR and/or USP substrate analogs can be of any inorganic or organic composition. EcR and/or USP substrate analogs can be, but need not be, structurally similar to an EcR and/or USP natural substrate as long as they can interact with the active site of that EcR and/or USP protein. EcR and/or USP substrate analogs can be designed using computer-generated structures of EcR and/or USP proteins of the present invention or computer structures of EcR's and/or USP's natural substrates. Preferred sites to model include one or more of the active sites of USP and/or EcR proteins. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea EcR and/or USP). A preferred EcR and/or USP substrate analog is a EcR and/or USP mimetic compound (i.e., a compound that is structurally and/or functionally similar to a natural substrate of an EcR and/or USP of the present invention, particularly to the region of the substrate that interacts with the EcR and/or USP active site, but that inhibits EcR and/or USP activity upon interacting with the EcR and/or USP active site).

Preferred EcR active sites include those portions of an EcR protein that binds to ecdysone, USP, and/or EcRE. Preferred USP active sites include those portions of a USP protein that binds to ecdysone, EcR, and/or EcRE.

The present invention also includes a therapeutic composition comprising at least one flea EcR and/or USP-based compound of the present invention in combination with at least one additional compound protective against one or more infectious agents. Examples of such compounds and infectious agents are disclosed herein.

In one embodiment, a therapeutic composition of the present invention can be used to protect an animal from flea infestation by administering such composition to a flea in order to prevent infestation. Such administration could be oral, or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present in the blood of a host animal that has been administered a therapeutic composition of the present invention.

Therapeutic compositions of the present invention can be administered to any animal susceptible to such therapy, preferably to mammals, and more preferably to dogs, cats, humans, ferrets, horses, cattle, sheep and other pets, economic food animals, work animals and/or zoo animals. Preferred animals to protect against flea infestation include dogs, cats, humans and ferrets, with dogs and cats being particularly preferred.

In accordance with the present invention, a host animal (i.e., an animal that is or is capable of being infested with fleas) is treated by administering to the animal a therapeutic composition of the present invention in such a manner that the composition itself (e.g., an EcR and/or USP inhibitor, an EcR and/or USP synthesis suppressor (i.e., a compound that decreases the production of EcR and/or USP in fleas), an EcR and/or USP mimetope, or an anti-EcR or anti-USP antibody) or a product generated by the animal in response to administration of the composition (e.g., antibodies produced in response to administration of a flea EcR and/or USP protein or nucleic acid molecule, or conversion of an inactive inhibitor "prodrug" to an active EcR and/or USP inhibitor) ultimately enters the flea. A host animal is preferably treated in such a way that the compound or product thereof enters the blood stream of the animal. Fleas are then exposed to the composition or product when they feed from the animal. For example, flea EcR and/or USP inhibitors administered to an animal are administered in such a way that the inhibitors enter the blood stream of the animal, where they can be taken up by feeding fleas. The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces. In accordance with the present invention, reducing EcR and/or USP activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults).

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, - or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ A preferred controlled release formulation of the present invention is capable of releasing a composition of the present invention into the blood of the treated animal at a constant rate sufficient to attain therapeutic dose levels of the composition to protect an animal from flea infestation. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infestation in order to prevent infestation and/or can be administered to animals after infestation. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxviruses, adenoviruses, herpesviruses, picornaviruses, and retroviruses, with those based on alphaviruses (such as sindbis or Semliki forest virus), species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 µg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from flea infestation as disclosed herein. For example, a recombinant virus vaccine comprising an EcR and/or USP nucleic acid molecule of the present invention is administered according to a protocol that results in the animal producing a sufficient immune response to protect itself from flea infestation. A preferred single dose of a recombinant virus vaccine of the present invention is from about $1 \times 10^4$ to about $1 \times 10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

One therapeutic composition of the present invention includes an inhibitor of flea EcR and/or USP activity, i.e., a compound capable of substantially interfering with the function of a flea EcR and/or USP susceptible to inhibition by an inhibitor of flea EcR and/or USP activity. An inhibitor of EcR and/or USP activity can be identified using flea EcR and/or USP proteins of the present invention. One embodiment of the present invention is a method to identify a compound capable of inhibiting EcR and/or USP activity of a flea. Such a method includes the steps of (a) contacting (e.g., combining, mixing) an isolated flea EcR and/or USP protein, preferably a *C. felis* EcR and/or USP protein of the present invention, with a putative inhibitory compound under conditions in which, in the absence of the compound, the protein has EcR and/or USP activity, and (b) determining if the putative inhibitory compound inhibits the EcR and/or USP activity. As used herein, the term "EcR activity" means the ability of EcR to bind to or otherwise interact with ecdysone, USP and/or EcRE and thereby affect DNA transcription. As used herein, the term "USP activity" means the ability of USP to bind to or otherwise interact with ecdysone, EcR and/or EcRE, preferably the ability to affect the association of EcR with ecdysone, more preferably the ability to promote, improve and/or enhance the association between EcR and ecdysone, thereby affecting DNA transcription.

Another embodiment of a method to identify a compound capable of inhibiting EcR and/or USP activity of a flea includes the steps of (a) contacting an isolated flea EcR and/or USP protein, preferably a *C. felis* EcR and/or USP protein of the present invention, with a putative inhibitory compound under conditions in which the EcR and/or USP protein can bind to the putative inhibitory compound, and (b) determining if the putative inhibitory compound binds to the EcR and/or USP protein.

Putative inhibitory compounds to screen include small organic molecules, antibodies (including mimetopes thereof) and substrate analogs. Methods to determine EcR and/or USP activity are known to those skilled in the art; see, for example, the Examples section of the present application. Methods to determine binding of a putative inhibitory compounds to an EcR and/or USP protein are known to those of skill in the art and include, for example, determining changes in molecular mass using surface plasmon resonance (e.g., determining light scatter by an inhibitor or an EcR and/or USP protein, before and after contacting the inhibitor or protein with an EcR and/or USP protein or inhibitor, respectively).

One embodiment of the present invention is a method to identify proteins that specifically interact with an EcR or USP protein of the present invention. The method can comprise the steps of a) identifying and isolating a protein-binding domain of an isolated flea EcR or USP protein; b) contacting that protein-binding domain with isolated flea proteins under conditions such that a flea protein and the protein-binding domain can selectively interact and/or bind to each other, using, for example, the yeast two-hybrid system see, for example, Luban, et al., 1995, Curr. Opin. Biotechnol., 6, 59–64; and c) identifying those proteins that specifically bind to the isolated EcR or USP protein-binding domain. Additional methods to identify protein—protein interactions with the protein-binding domains of an isolated EcR or USP protein of the present invention are known to those skilled in the art. Examples include Biacore® screening, confocal immunofluorescent microscopy, and immunoprecipitations.

An inhibitor of EcR and/or USP function can be identified using flea EcR and/or USP proteins of the present invention.

A preferred inhibitor of EcR and/or USP function is a compound capable of substantially interfering with the function of a flea EcR and/or USP protein and which does not substantially interfere with host animal EcR and/or USP activity. As used herein, a compound that does not substantially inhibit host animal EcR and/or USP activity is one that, when administered to a host animal, the host animal shows no significant adverse effects attributable to the compound and which, when administered to an animal in an effective manner, is capable of protecting that animal from flea infestation.

A preferred method to identify a compound capable of inhibiting EcR and/or USP activity includes contacting an isolated flea EcR and/or USP protein having an amino acid sequence selected from the group consisting of SEQ ID NO:6, SEQ ID NO:14, SEQ ID NO:27, and SEQ ID NO:33 with a putative inhibitory compound under conditions in which, in the absence of said compound, said protein has EcR and/or USP activity; and determining if said putative inhibitory compound inhibits said activity. An additional preferred method of identifying a compound capable of inhibiting flea EcR and/or USP activity includes contacting an isolated host animal EcR and/or USP protein with the putative EcR and/or USP inhibitory compound under conditions in which, in the absence of said compound, said host animal EcR and/or USP protein has EcR and/or USP activity; and determining if said putative inhibitory compound inhibits the host animal EcR and/or USP activity.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This Example describes the preparation of a head and nerve cord cDNA pool from the flea *Ctenocephalides felis*.

A flea head and nerve cord cDNA pool was prepared using Clonetech's MARATHON™ cDNA Amplification kit and protocol, available from Clonetech Laboratories, Palo Alto, Calif. Briefly, head and nerve cords from 100 fed and 100 unfed adult fleas were isolated and about 8 $\mu$g of total RNA was extracted and used for a first strand cDNA synthesis reaction with AMV reverse transcriptase. Five microliters ($\mu$l) of the first reaction product was used as the template in a second strand cDNA reaction, using Clonetech's second strand enzyme cocktail and protocols, to yield double stranded cDNA. Marathon cDNA adaptors were ligated to double stranded cDNA using T4 DNA ligase according to the manufacturer's instructions.

EXAMPLE 2

This example describes the cloning and sequencing of flea ecdysone receptor (EcR) nucleic acid molecules.

Degenerate primers were designed based on several conserved regions of published EcR amino acid sequences of *Bombyx mori*, Swevers et al., 1995, ibid., *Drosophila melanogaster*, Koelle et al., 1991, ibid., and *Manduca sexta*, Fujiwara et al., 1995, ibid., and human retinoic acid receptor alpha-1 sequence, Giguere et al., 1987, ibid. Sense primer JER-2, having the nucleotide sequence 5'TGY GAA ATG GAY ATG TAY ATG 3' (wherein Y represents C or T), designated herein as SEQ ID NO:44, was used in combination with antisense primer JER-4, having the nucleotide sequence 5'CCY TTW GCR AAT TCN ACD AT 3'(wherein Y represents C or T, W represents A or T, R represents A or G, N represents A, T, C or G, and D represents A or G or T), designated herein as SEQ ID NO:45, to produce a PCR product from a flea mixed instar cDNA library, prepared as described in Example 11 of PCT Publication WO 98/21324. PCR reaction were performed using the following amplification cycles: (1) one cycle at 95° C. for three minutes; (2) thirty-five cycles at 95° C. for thirty seconds, 50° C. for thirty seconds, and 72° C. for one minute; and (3) one cycle of 72° C. for nine minutes, in reactions containing 1.5 millimolar (mM) $MgCL_2$, 0.2 mM dNTPs, 1 $\mu$M of each primer, 1 $\mu$l of 5 units per microliter (U/$\mu$l) Taq polymerase, and 1 $\mu$l of template. The reaction product was re-amplified under the same reaction conditions except that part (2) ran for only twenty-five cycles. The resulting PCR amplification product was a fragment of about 446 nucleotides, denoted herein as $nECR_{446}$. The PCR product was purified using Qiagen's Qiaquick™ kit using the manufacturer's protocol, available from Qiagen, Chatsworth, Calif., and sequenced using primers JER-2 and JER-4 using standard sequencing methods. The resulting nucleic acid sequence of $nECR_{446}$ has a coding strand presented herein as SEQ ID NO:1 and a complementary strand presented herein as SEQ ID NO:2.

$nECR_{446}$ was used as the template for a second PCR reaction using sense primer BER-1, having nucleotide sequence 5'GGT TCC CGA AAA CCA ATG 3', designated herein as SEQ ID NO:46, and anti-sense primer BER-2, having nucleotide sequence 5'GCC GAA ATT CM GAG CTT C3', designated herein as SEQ ID NO:47. PCR reactions were performed using the following amplification cycles: (1) one cycle at 95° C. for two minutes and forty seconds; (2) thirty-five cycles at 95° C. for thirty seconds, 52.8° C. for thirty seconds, and 72° C. for one minute; and (3) one cycle at 72° C. for eight minutes, in reactions containing 1.5 mM $MgCL_2$, 0.2 mM dNTPs, 1 $\mu$M of each primer, 1 $\mu$l of 5U/$\mu$l Taq polymerase, and 1$\phi$1 of template. The resulting PCR amplification product was a fragment of about 350 nucleotides, denoted herein as $nECR_{350}$. The PCR product was purified using the Qiaquick™ kit and sequenced using primers BER-1 and BER-2 using standard sequencing methods. The resulting nucleic acid sequence of $nECR_{350}$ has a coding strand presented herein as SEQ ID NO:3 and a complementary strand presented herein as SEQ ID NO:4.

A DNA probe comprising nucleotides from $nECR_{350}$, SEQ ID NO:3, was labeled with $^{32}P$ and used to screen about 300,000 plaques from the flea mixed instar cDNA library and a flea pre-pupal cDNA library prepared as described in Example 11 of PCT Publication WO 98/21324. The following hybridization conditions were used. Filters were hybridized with about 1×10$^6$ counts per minute (cpm) per ml of the probe in 5× SSPE, 1% Sarcosyl, 0.1 mg/ml salmon sperm DNA and 0.1 mg/ml BLOTTO at 45° C. for about 14 hours. The filters were washed twice for 30 minutes per wash in 500 ml of 5× SSPE, 1% Sarcosyl at 45° C., hereinafter referred to as "standard EcR hybridization conditions". A positive plaque, denoted herein as EcR3 was further screened to obtain a pure plaque population. In vivo excision was performed using the Stratagene Ex-Assist™ helper phage system and protocols, to convert ten positive plaques to pBluescript plasmid DNA. Multiple clones were sequenced following preparation with a Qiagen Qiaprep™ spin mini prep kit using the manufacturer's instructions and restriction enzyme digestion with about 20 U/$\mu$l each of Eco RI and Xho I, available from New England Biolabs, Beverly, Mass. A clone was isolated from a tertiary plaque of EcR3, containing a nucleic acid molecule of about 2822 base pairs, referred to herein as nECR$_{2822}$, having a nucleotide sequence denoted herein as SEQ ID NO:5. The complement of SEQ ID NO:5 is represented herein as SEQ ID NO:7.

Translation of SEQ ID NO:5 suggests that nucleic acid molecule nECR$_{2822}$ encodes a full-length EcR protein of 560 amino acids, referred to herein as PECR$_{560}$, having an amino acid sequence represented by SEQ ID NO:6, assuming the initiation codon spans from nucleotide 605 through nucleotide 607 of SEQ ID NO:5 and the termination codon spans from nucleotide 2285 through nucleotide 2287 of SEQ ID NO:5. The coding region encoding PECR$_{560}$, is represented by nucleic acid molecule nECR$_{1680}$, having a coding strand with the nucleic acid sequence represented by SEQ ID NO:8 and a complementary strand with nucleic acid sequence represented by SEQ ID NO:10. The amino acid sequence of PECR$_{560}$ predicts that PECR$_{560}$ has an estimated molecular weight of about 61.8 kilodaltons (kDa) and an estimated pI of about 6.5. A DNA probe comprising nucleotide 318 through nucleotide 2287 of SEQ ID NO:5 was labeled with $^{32}$P and used to probe separate samples of *C. felis* genomic DNA which had been digested with Eco RI and Eco RV, respectively. One to three bands of digested DNA hybridized with labeled probes, under standard EcR hybridization conditions described herein indicating that each of these genes are single copy number in genes.

Comparison of amino acid sequence SEQ ID NO:6 with amino acid sequences reported in GenBank indicates that SEQ ID NO:6 showed the most homology, i.e., about 64% identity between SEQ ID NO:6 and a *Drosophila melanogaster* EcR protein isoform B1, GenBank Accession No. P34021. Comparison of SEQ ID NO:8 with nucleic acid sequences reported in GenBank indicates that SEQ ID NO:8 showed the most homology, i.e., about 63% identity between SEQ ID NO:8 and a *Lucilia cuprina* EcR nucleic acid molecule, GenBank Accession number U75377. Percent identity calculations were performed using GCG version 9.0-UNIX using default parameters.

An isoform of flea EcR was isolated as follows. Primer BER-10, having the nucleotide sequence 5'GTC AGG AAT GTA GGC TCA 3', designated herein as SEQ ID NO:48 and corresponding to nucleotides 1015 through 1032 of nucleic acid molecule nECR$_{2822}$ was used in combination with vector primer T3, having the nucleotide sequence 5'AAT TAA CCC TCA CTA AAG GG 3', designated herein as SEQ ID NO:49, to generate a PCR product from a primary phage plaque, denoted EcR8, which hybridized to nECR$_{350}$ using standard EcR hybridization conditions. PCR reaction were performed using the following amplification cycles: (1) one cycle at 95° C. for two minutes and forty seconds; (2) thirty-five cycles at 95° C. for thirty seconds, 50° C. for one minute, and 72° C. for two minutes; and (3) one cycle at 72° C. for eight minutes, in reactions containing 1.5 mM MgCL$_2$, 0.2 mM dNTPs, 1 μM of each primer, 1 μl of 5U/μl Taq polymerase, and 1 μl of template, hereinafter referred to as "standard PCR conditions". The resulting PCR amplification product was a fragment of about 666 base pairs, denoted herein as nECR$_{666}$. The PCR product was purified using the Qiaquick™ kit and sequenced using primers BER-10 and T3 using standard sequencing methods. The resulting nucleic acid sequence of nECR$_{666}$ has a coding strand presented herein as SEQ ID NO:11 and a complementary strand presented herein as SEQ ID NO:12.

A DNA probe comprising nucleotides from nECR$_{666}$, SEQ ID NO:11, was labeled with $^{32}$P, and used to re-screen EcR8 primary phage plaques until a pure plaque population was obtained. In vivo excision was performed using Stratagene Ex-Assist™ helper phage system and protocols, to convert positive plaques to pBluescript plasmid DNA. Multiple clones were sequenced following preparation with the Qiaprep™ spin mini prep kit and restriction enzyme digestion with 20 U/μl each of Eco RI and Xho I. A clone was isolated having an about 4148 base pair insert, referred to herein as nECR$_{4148}$, having a nucleotide sequence denoted herein as SEQ ID NO:13. The complement of SEQ ID NO:13 is represented herein by SEQ ID NO:15.

Translation of SEQ ID NO:13 suggests that nucleic acid molecule nECR$_{4148}$ encodes a full-length EcR protein of 561 amino acids, referred to herein as PECR$_{561}$, having an amino acid sequence represented by SEQ ID NO:14, assuming the initiation codon spans from nucleotide 184 through nucleotide 186 of SEQ ID NO:13 and the termination codon spans from nucleotide 1867 through nucleotide 1869 of SEQ ID NO:13. The coding region encoding PECR$_{561}$, is represented by nucleic acid molecule nECR$_{1683}$, having a coding strand with the nucleic acid sequence represented by SEQ ID NO:16 and a complementary strand with nucleic acid sequence represented by SEQ ID NO:18. The amino acid sequence of PECR$_{561}$ predicts that PECR$_{561}$ has an estimated molecular weight of about 62.6 kDa and an estimated pI of about 7.

Comparison of amino acid sequence SEQ ID NO:14 with amino acid sequences reported in GenBank indicates that SEQ ID NO:14 showed the most homology, i.e., about 66% identity between SEQ ID NO:14 and a *Drosophila melanogaster* EcR protein isoform A, GenBank Accession No. P34021. Comparison of SEQ ID NO:16 with nucleic acid sequences reported in GenBank indicates that SEQ ID NO:16 showed the most homology, i.e., about 59% identity between SEQ ID NO:16 and a Lucilia cuprina EcR nucleic acid molecule, GenBank Accession No. U75355. A comparison of nECR$_{2822}$ and nECR$_{4148}$ indicates that these molecules represent different variants of EcR in *C. felis*. Percent identity calculations were performed using GCG version 9.0-UNIX using default parameters.

EXAMPLE 3

This example describes the cloning and sequencing of flea ultraspiracle (USP) nucleic acid molecules.

Degenerate primers were designed based on several conserved regions of published USP amino acid sequences of *Bombyx mori*, Tzertzinis et al., 1994, ibid., *Drosophila melanogaster*, Oro et al., 1990, ibid, and *Manduca sexta*, Jindra et al., ibid., published amino acid sequences of human retinoic acid receptor RXR-gamma, Cooke et al., 1996, ibid., mouse retinoic acid receptor RXR-gamma, Leid et al., 1992, ibid., and *Xenopus laevis* retinoic acid receptor RXR-alpha, Blumberg et al., 1992, ibid. Sense primer B-USP-1 having the nucleotide sequence 5'GGW AAA CAY TAT GGW GTW TA 3'(wherein W represents A or T, and Y represents C or T), designated herein as SEQ ID NO:50, was used in combination with antisense primer B-USP-3, having the nucleotide sequence 5'TTC TTC YTG NAC WHC TTC 3'(wherein Y represents C or T, N represent A or T or C or G, and W represents A or T), designated herein as SEQ ID NO:51, to produce a PCR product from the flea pre-pupal cDNA library, using standard PCR conditions described in Example 2. The resulting PCR amplification product was a fragment of about 160 nucleotides, denoted herein as nUSP$_{160}$. The PCR product was purified using Qiagen's Qiaquick™ kit and protocol and cloned into the pCRII TA™ vector, available from Invitrogen, San Diego, Calif., according to the manufacturer's instructions. Clones were prepared using Qiagen's QlAprep™ spin mini prep kit and protocol and screened by restriction enzyme digest using 20 U/μl Eco RI. One screened clone was isolated and sequenced using TA+ and TA– primers, available from InVitrogen, The resulting nucleic acid sequence of nUSP$_{160}$ has a coding strand presented herein as SEQ ID NO:19 and a complementary strand presented herein as SEQ ID NO:20.

A DNA probe comprising nucleotides from nUSP$_{160}$, SEQ ID NO:19, was labeled with $^{32}$P and used to screen about 450,000 plaques from the flea pre-pupal cDNA library described in Example 2, using the following hybridization conditions. Filters were hybridized with about 1×10$^6$ counts per minute (cpm) per ml of the probe in 5×SSPE, 1% Sarcosyl, 0.1 mg/ml salmon sperm DNA and 0.1 mg/ml BLOTTO at 45° C. for about 14 hours. The filters were washed twice for 30 minutes per wash in 500 ml of 5× SSPE, 1% Sarcosyl at 45° C., hereinafter referred to as "standard USP hybridization conditions". Two positive plaques, denoted herein as USP11 and USP12, were further screened to obtain pure plaque populations of each plaque. In vivo excision was performed using Stratagene Ex-Assist™ helper phage system and protocols, to convert positive plaques to pBluescript plasmid DNA. Clones USP11 and USP12 were sequenced following preparation with the Qiaprep™ spin mini prep kit and restriction enzyme digestion with 20 U/μl each of Eco RI and Xho I. A clone from plaque USP11 was isolated having an about 1421 base pair insert, referred to herein as nUSP$_{1421}$, having a nucleotide sequence denoted herein as SEQ ID NO:23. The complement of SEQ ID NO:23 is represented herein by SEQ ID NO:24.

Sequence analysis revealed that nUSP$_{1421}$ was truncated at the 5' end. Additional 5' sequence was determined as follows. Antisense primer B-USP-5, having nucleotide sequence 5'TTC TCG TTT CAT TCC ACA GG 3', designated herein as SEQ ID NO:52, which corresponds to nucleotides 141 to 160 of nUSP$_{160}$, was used in combination with primer T3, SEQ ID NO:49, to create a PCR product using the primary USP11 phage plug as the template and standard PCR conditions. The resulting about 819 base pair PCR product, referred to herein as nUSP$_{819}$, designated herein as SEQ ID NO:25, was sequenced and nucleotides 646 through 819 of nUSP$_{819}$ were found to overlap with nucleotides 11 through 185 of nUSP$_{1421}$.

Primers based upon the combined sequences of nUSP$_{1421}$ and nUSP$_{819}$, were used to produce a PCR product from the flea pre-pupal cDNA library containing a non-truncated 5' end. Sense primer USP11–50, having nucleotide sequence 5' AAA GGG AAC AAA AGC TGG AGC TCC ACC GC 3', designated herein as SEQ ID NO:53, was used in combination with antisense primer USP11–30, having the nucleotide sequence 5'TTA AAA TAT CAC TGG TTC GTA TCC TCC C 3', designated herein as SEQ ID NO:54, to produce the PCR product. The product from this first PCR reaction was used as the template in a second PCR reaction using sense primer USP11–51, having the nucleotide sequence 5'GGC GGC CGC TCT AGA ACT AGT GGA TC 3', designated herein as SEQ ID NO:55, and antisense primer USP11–31, having the nucleotide sequence 5'AGA CAA TCA ATA TCC CAA GTG CG 3', designated herein as SEQ ID NO:56, under standard PCR conditions as described in Example 2. The resulting PCR product was a fragment of about 1749 base pairs, denoted herein as nUSP$_{1749}$. The PCR product was purified using the Qiaquick™ kit and cloned into the pCRII TA™ vector, using the manufacturer's instructions. Clones were prepared using the QIAprep T spin mini prep kit and preferred clones were identified by restriction enzyme digestion using 20 U/μl Eco RI. One clone was isolated and sequenced using TA+ and TA– primers. The resulting nucleic acid sequence of nUSP$_{1749}$ has a coding strand presented herein as SEQ ID NO:26 and a complementary strand presented herein as SEQ ID NO:28.

Translation of SEQ ID NO:26 suggests that nucleic acid molecule nUSP$_{1749}$ encodes a full-length USP protein of 448 amino acids, referred to herein as PUSP$_{448}$, having an amino acid sequence represented by SEQ ID NO:27, assuming the initiation codon spans from nucleotide 306 through nucleotide 308 of SEQ ID NO:26 and the termination codon spans from nucleotide 1650 through nucleotide 1652 of SEQ ID NO:26. The coding region encoding PUSP$_{448}$, is represented by nucleic acid molecule nUSP$_{1344}$, having a coding strand with the nucleic acid sequence represented by SEQ ID NO:29 and a complementary strand with nucleic acid sequence represented by SEQ ID NO:31. The amino acid sequence of PUSP$_{448}$ predicts that PUSP$_{448}$ has an estimated molecular weight of about 49.6 kDa and an estimated pI of about 8.

Comparison of amino acid sequence SEQ ID NO:27 with amino acid sequences reported in GenBank indicates that SEQ ID NO:27 showed the most homology, i.e., about 58% identity between SEQ ID NO:27 and a *Drosophila melanogaster* steroid hormone receptor like protein, GenBank Accession No. S13119. Comparison of SEQ ID NO:29 with nucleic acid sequences reported in GenBank indicates that SEQ ID NO:29 showed the most homology, i.e., about 57% identity between SEQ ID NO:29 and a *Manduca sexta* USP-1 nucleic acid molecule, GenBank Accession No. U44837. Percent identity calculations were performed using GCG version 9.0-UNIX using default parameters.

A clone from plaque USP12 was isolated having an about 2149 base pair insert, referred to herein as nUSP$_{2149}$, having a nucleotide sequence denoted herein as SEQ ID NO:21. The complement of SEQ ID NO:21 is represented herein by SEQ ID NO:22. Sequence analysis revealed that nUSP$_{2149}$ contains an unusual 31' end that is not homologous to published USP sequences, therefore additional 3' sequence was determined as follows. Sense primer USP12–51, having the nucleotide sequence 5'CTG CAT AAA ATG CCT AAA GTC GCG GAC 3', designated herein as SEQ ID NO:57, was used in combination with antisense primer USP11–31, SEQ ID NO:56, to produce a PCR product using 5 μl of a 1:50 dilution of the flea head and nerve cord RACE cDNA pool described in Example 1 under standard PCR conditions. The resulting PCR product was a fragment of about 1975 base pairs, denoted herein as nUSP$_{1975}$. The PCR product was purified using Qiagen's Qiaquick™ kit and cloned into the pCRII TA™ vector. Clones were prepared using a Biorad Quantum™ mini prep kit and the manufacturer's protocol, available from Biorad, Hercules, Calif., and preferred clones were identified by restriction enzyme digest using 20 U/μl Eco RI. One clone was isolated and sequenced using TA+ and TA– primers. The resulting nucleic acid sequence of nUSP$_{1975}$ has a coding strand presented herein as SEQ ID NO:32 and a complementary strand presented herein as SEQ ID NO:34.

Translation of SEQ ID NO:32 suggests that nucleic acid molecule nUSP$_{1975}$ encodes a full-length USP protein of 474 amino acids, referred to herein as PUSP$_{474}$, having an amino acid sequence represented by SEQ ID NO:33, assuming the initiation codon spans from nucleotide 454 through nucleotide 456 of SEQ ID NO:32 and the termination codon spans from nucleotide 1876 through nucleotide 1878 of SEQ ID NO:32. The coding region encoding PUSP$_{474}$, is represented by nucleic acid molecule nUSP$_{1422}$, having a coding strand with the nucleic acid sequence represented by SEQ ID NO:35 and a complementary strand with nucleic acid sequence represented by SEQ ID NO:37. The amino acid sequence of PUSP$_{474}$ predicts that PUSP$_{474}$ has an estimated molecular weight of about 52 kDa and an estimated pI of about 8.4. A DNA probe comprising nucleotide 99 through nucleotide 1878 of SEQ ID NO:32 was labeled with $^{32}$P and used to probe separate samples of C. felis genomic DNA which had been digested with Eco RI and Eco RV, respectively. One to three bands of digested DNA hybridized with labeled probes, using standard USP hybridization conditions described herein, indicating that each of these genes are single copy number in genes.

Comparison of amino acid sequence SEQ ID NO:33 with amino acid sequences reported in GenBank indicates that SEQ ID NO:33 showed the most homology, i.e., about 56% identity between SEQ ID NO:33 and a Drosophila melanogaster steroid hormone receptor-like protein, GenBank Accession No. S13119. Comparison of SEQ ID NO:35 with nucleic acid sequences reported in GenBank indicates that SEQ ID NO:35 showed the most homology, i.e., about 51% identity between SEQ ID NO:35 and a nucleic acid molecule encoding a Drosophila melanogaster steroid hormone receptor-like protein, GenBank Accession No. X52591. A comparison of nUSP$_{1749}$ and nUSP$_{1975}$ indicates that these molecules represent different variants of USP in C. felis. Percent identity calculations were performed using GCG version 9.0-UNIX using default parameters.

EXAMPLE 4

This example describes the expression of C. felis EcR and USP proteins.

A. EcR Expression A putative ligand binding site of C. felis EcR spanning nucleotide 1549 to nucleotide 2161 of SEQ ID NO:5, referred to herein as nECR$_{612}$, having a coding strand with the nucleic acid sequence represented by SEQ ID NO:38 and a complementary strand with nucleic acid sequence represented by SEQ ID NO:39, was isolated and expressed as follows. Primer EcR-LBD-F, having nucleotide sequence 5'GCG GGA TCCCAA GAT GGA TAT GAA CAA CCT 3', designated herein as SEQ ID NO:58 and having a Bam HI site indicated in bold, was used in combination with antisense primer EcR-LBD-R, having nucleotide sequence 5'GCG CAA TTCTCA ATC CCA AAT TTC TTC TAA AAA TCT 3', designated herein as SEQ ID NO:59 and having an Eco RI site indicated in bold, to produce a PCR product under standard PCR conditions using nECR$_{2822}$ as the template. The resulting PCR product was cut with 20 (U/µl) each of Eco RI and Bam HI restriction endonucleases, and subcloned into pGEX-6P1 expression vector, available from Pharmacia, Piscataway, N.J., which had been cut with Eco RI and Bam HI. The resulting recombinant molecule, referred to herein as pGEX-nECR$_{612}$, was transformed into E. coli strain BL21, available from Novagen, Madison, Wis., to form recombinant cell E. coli:pGEX-nECR$_{612}$. Colonies were screened by restriction enzyme digestion with 20 U/µl each of Bam HI and Eco RI after DNA was isolated using the Qiaspin™ Mini Prep kit. Preferred colonies were then incubated in the presence of 1 mM isopropylthio-β-galactoside (IPTG) to induce expression of recombinant protein. Expression of protein was confirmed using antibodies that bind to the GST tag and Western Blot analysis which showed expression of an about 55 kD protein.

B. USP Expression A putative ligand binding site of C. felis USP spanning nucleotide 857 to nucleotide 1633 of SEQ ID NO:26, referred to herein as nUSP$_{776}$, having a coding strand with the nucleic acid sequence represented by SEQ ID NO:40 and a complementary strand with nucleic acid sequence represented by SEQ ID NO:41, was isolated and expressed as follows. Primer USP-LBD-F, having nucleotide sequence 5'GCG GCA TCCCTC TGT TCG AGA TTT AAC GGT A 3', designated herein as SEQ ID NO:60 and having a Bam HI site indicated in bold, was used in combination with antisense primer USP-LBD-R, having nucleotide sequence 5'GCG AAG CTTTCA ACC GAT GGG TCC GCC 3', designated herein as SEQ ID NO:61 and having a Hind III site indicated in bold, to produce a PCR product under standard PCR conditions using nUSP$_{1749}$ as the template. The resulting PCR product was cut with 20 U/µl each of Bam HI and Hind III restriction endonucleases, and subcloned into the pTrc-His-B expression vector, available from Invitrogen, which had been cut with Bam HI and Hind III. The resulting recombinant molecule, referred to herein as pTrc-His-nUSP$_{776}$ was transformed into E. coli strain BL21 to form recombinant cell E. coli:pTrc-nUSP$_{718}$. Colonies were screened by restriction enzyme digestion with 20 U/µl each of Bam HI and Hind III after DNA was isolated using the Qiaspin™ Mini Prep kit. Preferred colonies were then incubated in the presence of 1 mM IPTG to induce expression of recombinant protein. Expression of protein was confirmed using antibodies that bind to the T7 tag and Western Blot analysis which showed expression of an about 36 kD protein.

C. EcR and USP co-expression The ligand binding sites of C. felis EcR and USP described in Example 3A and 3B were co-expressed as follows. The recombinant molecule pTrc-His-nUSP$_{776}$ was used as the template in a PCR reaction using sense primer USP-GEX-LBD-F, having nucleotide sequence 5'GCG CCC GGG GGA TTA ACT TTA TTA TTA AAA ATT AAA 3', designated herein as SEQ ID NO:62 and having an Xma I site indicated in bold, and antisense primer USP-GEX-LBD-R, having nucleotide sequence 5'GCG C GC GGC CGC AAC CTTTCA ACC GAT GGG TCC 3', designated herein as SEQ ID NO:63 and having a NotI site indicated in bold. PCR reactions were performed using the following conditions: (1) one cycle at 95° C. for two minutes and forty seconds; (2) thirty-five cycles at 95° C. for thirty seconds, 52° C. for thirty seconds, and 72° C. for one minute and thirty seconds; and (3) one cycle at 72° C. for seven minutes, in reactions containing 1.5 mM MgCL$_2$, 0.2 mM dNTPs, 1 µM of each primer, 1 µl of 5 U/µl Taq polymerase, and 1 µl of template. The resulting PCR product was a fragment of about 943 base pairs containing the ribosome binding site of pTrc-His and the ligand binding site of USP, designated herein as nUSP$_{943}$, having a coding strand with the nucleic acid sequence represented by SEQ ID NO:42 and a complementary strand with nucleic acid sequence represented by SEQ ID NO:43.

A dicistronic vector containing the ligand binding sites of USP and EcR was produced as follows. The recombinant molecule pGEX-nECR$_{612}$ and the PCR product nUSP$_{943}$, each were digested with 10 U/µl of XmaI and NotI restriction endonucleases, available from New England Biolabs. The two restriction enzyme digested products were combined and allowed to ligate to form a recombinant molecule designated pGEX-EcR$_{612}$-USP$_{943}$, which was transformed into E. coli strain BL21 to form the recombinant cell referred to as E. coli:pGEX-EcR$_{612}$-USP$_{943}$.

Colonies were screened by restriction enzyme digestion with 20 U/µl each of Bam HI and NotI after DNA was isolated using the Qiaspin™ Mini Prep kit. Selected colonies were then incubated in the presence of 1 mM IPTG to induce expression of recombinant protein. Expression of the recombinant proteins was confirmed by Western Blot analysis using antibodies that bind specifically to the T7 tag and the GST tag of the recombinant proteins. The resulting Western identified an about 55 kD protein and an about 36 kD protein.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated nucleic acid molecule comprising a nucleic acid sequence selected from the group consisting of (a) a nucleic acid sequence that encodes a protein having an amino acid sequence selected from the group consisting of SEQ ID NO: 6, SEQ ID NO: 64, SEQ ID NO: 65, and variants thereof that are at least 95% identical to an amino acid sequence selected from the group consisting of SEQ ID NO: 6 and SEQ ID NO: 65, wherein said protein has ecdysone receptor activity; and (b) a nucleic acid sequence complementary to the full length of a nucleic acid sequence of (a).

2. The nucleic acid molecule of claim 1, comprising a nucleic acid sequence selected from the group consisting of SEQ ID NO:5, SEQ ID NO:7, SEQ ID NO:8, SEQ ID NO:10.

3. The nucleic acid molecule of claim 1, wherein said nucleic acid molecule encodes a protein comprising an amino acid sequence selected from the group consisting of SEQ ID NO:6, SEQ ID NO:64, and SEQ ID NO:65.

4. A recombinant molecule comprising a nucleic acid molecule as set forth in claim 1 operatively linked to a transcription control sequence.

5. An isolated recombinant cell comprising a nucleic acid molecule as set forth in claim 1.

6. A method to produce a protein, said method comprising (a) culturing a cell transformed with an isolated nucleic acid molecule comprising a nucleic acid sequence that encodes a protein having an amino acid sequence selected from the group consisting of SEQ ID NO:6, SEQ ID NO:64, and SEQ ID NO:65, and variants thereof that are at least 95% identical to an amino acid sequence selected from the group consisting of SEQ ID NO: 6, and SEQ ID NO: 65, wherein said protein has ecdysone receptor activity; and (b) recovering the expresses protein.

7. The method of claim 6, wherein said protein comprises an amino acid sequence selected from the group consisting of SEQ ID NO:6, SEQ ID NO:64, and SEQ ID NO:65.

8. A composition comprising an excipient and an isolated nucleic acid molecule comprising a nucleic acid sequences selected from the group consisting of (a) a nucleic acid molecule sequence that encodes a protein having an amino acid sequence selected from the group consisting of SEQ ID NO:6, SEQ ID NO:64, SEQ ID NO:65, and variants thereof that are at least 95% identical to an amino acid sequence selected from the group consisting of SEQ ID NO:6, and SEQ ID NO:65, wherein said protein has ecdysone receptor activity; and (b) a nucleic acid sequence complementary to the full length of to a nucleic acid sequence of (a).

9. The composition of claim 8, wherein said nucleic acid molecule comprises a nucleic acid sequence selected from the group consisting of SEQ ID NO:5, SEQ ID NO:7, SEQ ID NO:8, SEQ ID NO:10.

10. The composition of claim 8, wherein said nucleic acid molecule encodes a protein comprising an amino acid sequence selected from the group consisting of SEQ ID NO:6, SEQ ID NO:64, SEQ ID NO:65.

* * * * *

SEQUENCE LISTING

```
<160> NUMBER OF SEQ ID NOS: 71

<210> SEQ ID NO 1
<211> LENGTH: 446
<212> TYPE: DNA
<213> ORGANISM: Ctenocephalides felis

<400> SEQUENCE: 1
tgtttggctg tcggaatgcg ccccgagtgc gtggttcccg aaaaccaatg cgccatgaag      60
cgaaaggaaa agaaggcaca gaaggaaaag gacatcggac caatatcagg taccgttgga     120
aaatctgctg ctcccttagc gaattctgca ttacttcaga agcctgatat tttgcctgcg     180
gtcatgaaat gcgacccatt acctccagaa gcaactaaag tgaaattttt gtcagacaag     240
attcttgctg aaaacagaat tcgaaatgtt ccacctttga ctgcaaatca agaatatgtg     300
atcgcaagat tagtgtggta ccaagatgga tatgaacaac cttctgagga agacctacga     360
aggataatga taagtacacc aggtgaagat gaagctgttg aatttcggca tataactgaa     420
attaccatac ttactgtgca gcttat                                          446

<210> SEQ ID NO 2
<211> LENGTH: 446
<212> TYPE: DNA
<213> ORGANISM: Ctenocephalides felis

<400> SEQUENCE: 2
ataagctgca cagtaagtat ggtaatttca gttatatgcc gaaattcaac agcttcatct      60
tcacctggtg tacttatcat tatccttcgt aggtcttcct cagaaggttg ttcatatcca     120
tcttggtacc acactaatct tgcgatcaca tattcttgat ttgcagtcaa aggtggaaca     180
tttcgaattc tgttttcagc aagaatcttg tctgacaaaa atttcacttt agttgcttct     240
ggaggtaatg ggtcgcattt catgaccgca ggcaaaatat caggcttctg aagtaatgca     300
gaattcgcta agggagcagc agattttcca acggtacctg atattggtcc gatgtccttt     360
tccttctgtg ccttctttc ctttcgcttc atggcgcatt ggttttcggg aaccacgcac     420
tcggggcgca ttccgacagc caaaca                                          446

<210> SEQ ID NO 3
<211> LENGTH: 350
<212> TYPE: DNA
<213> ORGANISM: Ctenocephalides felis

<400> SEQUENCE: 3
gaagcgaaag gaaagaagg cacagaagga aaaggacatc ggcaatatca ggtaccgttg       60
gaaaatctgc tgctccctta gcgaattctg cattccttca gaagcctgat attttgcctg     120
cggtcatgaa atgcgaccca ttacctccag aagcaactaa agtgaaattt tgtcagaca      180 agattcttgc tgaaaacaga attcgaaatg ttccaccttt gactgcaaat caagaatatg     240
tgatcgcaag attagtgtgg taccaagatg gatatgaaca accttctgag gaagacctac     300
gaaggataat gataagtaca ccaggtgaag atgaagctgt tgaatttcgg                350
```

<210> SEQ ID NO 4
<211> LENGTH: 350
<212> TYPE: DNA
<213> ORGANISM: Ctenocephalides felis

<400> SEQUENCE: 4

```
ccgaaattca acagcttcat cttcacctgg tgtacttatc attatccttc gtaggtcttc      60
ctcagaaggt tgttcatatc catcttggta ccacactaat cttgcgatca catattcttg     120
atttgcagtc aaaggtggaa catttcgaat tctgttttca gcaagaatct tgtctgacaa     180
aaatttcact ttagttgctt ctggaggtaa tgggtcgcat tcatgaccg caggcaaaat     240
atcaggcttc tgaaggaatg cagaattcgc taagggagca gcagattttc caacggtacc     300
tgatattgcc gatgtccttt tccttctgtg ccttcttttc ctttcgcttc                350
```

<210> SEQ ID NO 5
<211> LENGTH: 2822
<212> TYPE: DNA
<213> ORGANISM: Ctenocephalides felis
<220> FEATURE:
<221> NAME/KEY: CDS
<222> LOCATION: (605)..(2287)
<223> OTHER INFORMATION:

<400> SEQUENCE: 5

```
gctatatata caagacgcac atgctcatat cactaattat atataaccat taacaattat      60
atgtataatt gtatttgtga atgaaacac atgctaccta aaaactgatt cgtatgccgc     120
tctatcaatc agaatgata attaaacaat tttttatat tgaaatagaa catattatgt     180
tcatatgtca ataacaaatt ttaaacattc atccaagtta cctatttat gcttttaaga     240
tattatttat ttatttattt tgttttgtaa aatttaaaat tttacataaa tactttctaa     300
ctatgaatat aaattaatat acaaaagatt ttgaaactaa gaggaaaagt aattataatc     360
attttaatca ttaaattata tactcaaaat gatacaatta gattttacag tcacacacat     420
taggtacaga gattcaatta tgaattagga gttgagaaat gctttcgagt aaaatctgca     480
ataagatgac tatattccta aggatgttat gtcagtcata aataaaaatc actatatttt     540
caatttgtgt atggtgatct tctaaaggat aaatgtgtga agtgaaatac cttgcattat     600
``` caac atg aaa cga cgt tgg tct aac aac ggt ggc ttc caa acc ttg cgg    649
     Met Lys Arg Arg Trp Ser Asn Asn Gly Gly Phe Gln Thr Leu Arg
       1               5                  10                  15 atg ctc gaa gat gtt gca tct ggt gag gta acg tcg tct tct ggt ggc    697
Met Leu Glu Asp Val Ala Ser Gly Glu Val Thr Ser Ser Ser Gly Gly
                 20                  25                  30 gcc ctg gct gcg ttg agt ccg gct tcg tta ggt tcg ccc gag aca tat    745
Ala Leu Ala Ala Leu Ser Pro Ala Ser Leu Gly Ser Pro Glu Thr Tyr
             35                  40                  45 gcc gag ctg gat ttg tgg gtg tac gag gaa gct ggc tta cat cca ggt    793
Ala Glu Leu Asp Leu Trp Val Tyr Glu Glu Ala Gly Leu His Pro Gly
         50                  55                  60 tca ggt gtg caa gga tgc ggt gcg gtc gcc gcc ttg cca tcg atc gcg    841
Ser Gly Val Gln Gly Cys Gly Ala Val Ala Ala Leu Pro Ser Ile Ala
     65                  70                  75 aca cag gtc ccc cta gga ttg ccc gct atg gac cta ccg cac acg cct    889
Thr Gln Val Pro Leu Gly Leu Pro Ala Met Asp Leu Pro His Thr Pro
 80                  85                  90                  95 cgg agt gac agt gcg ggt agc atc tca tca gga cga gaa gac ctg tca    937
Arg Ser Asp Ser Ala Gly Ser Ile Ser Ser Gly Arg Glu Asp Leu Ser
                100                 105                 110

```
                                                    -continued ccg cct agt tct ttg aac ggc tat tca gca gat ggc tgc gaa gcg aag      985
Pro Pro Ser Ser Leu Asn Gly Tyr Ser Ala Asp Gly Cys Glu Ala Lys
        115                 120                 125 aag gcc aag aaa ggg ccg gcg ccg cgg cag cag gag gaa cta tgt ctt     1033
Lys Ala Lys Lys Gly Pro Ala Pro Arg Gln Gln Glu Glu Leu Cys Leu
    130                 135                 140 gtg tgc ggc gac cgt gcc tcc gga tat cat tac aac gct ctt act tgt     1081
Val Cys Gly Asp Arg Ala Ser Gly Tyr His Tyr Asn Ala Leu Thr Cys
145                 150                 155 gaa gga tgc aaa ggt ttt ttc cga cga agt gtg act aag aat gcc gtg     1129
Glu Gly Cys Lys Gly Phe Phe Arg Arg Ser Val Thr Lys Asn Ala Val
160                 165                 170                 175 tac gtg tgc aag ttt ggg cac acg tgc gaa atg gac atg tat atg cga     1177
Tyr Val Cys Lys Phe Gly His Thr Cys Glu Met Asp Met Tyr Met Arg
            180                 185                 190 cgc aaa tgt cag gaa tgt agg ctc aag aaa tgt ttg gct gtc gga atg     1225
Arg Lys Cys Gln Glu Cys Arg Leu Lys Lys Cys Leu Ala Val Gly Met
            195                 200                 205 cgc ccc gag tgc gtg gtt ccc gaa aac caa tgc gcc atg aag cga aag     1273
Arg Pro Glu Cys Val Val Pro Glu Asn Gln Cys Ala Met Lys Arg Lys
        210                 215                 220 gaa aag aag gca cag aag gaa aag gac atc gga cca ata tca ggt acc     1321
Glu Lys Lys Ala Gln Lys Glu Lys Asp Ile Gly Pro Ile Ser Gly Thr
225                 230                 235 gtt gga aaa tct gct gct ccc tta gcg aat tct gca tta ctt cag aag     1369
Val Gly Lys Ser Ala Ala Pro Leu Ala Asn Ser Ala Leu Leu Gln Lys
240                 245                 250                 255 cct gat att ttg cct gcg gtc atg aaa tgc gac cca tta cct cca gaa     1417
Pro Asp Ile Leu Pro Ala Val Met Lys Cys Asp Pro Leu Pro Pro Glu
                260                 265                 270 gca act aaa gtg aaa ttt ttg tca gac aag att ctt gct gaa aac aga     1465
Ala Thr Lys Val Lys Phe Leu Ser Asp Lys Ile Leu Ala Glu Asn Arg
            275                 280                 285 att cga aat gtt cca cct ttg act gca aat caa gaa tat gtg atc gca     1513
Ile Arg Asn Val Pro Pro Leu Thr Ala Asn Gln Glu Tyr Val Ile Ala
            290                 295                 300 aga tta gtg tgg tac caa gat gga tat gaa caa cct tct gag gaa gac     1561
Arg Leu Val Trp Tyr Gln Asp Gly Tyr Glu Gln Pro Ser Glu Glu Asp
305                 310                 315 cta cga agg ata atg ata agt aca cca gct gaa gat gaa gct ctt gaa     1609
Leu Arg Arg Ile Met Ile Ser Thr Pro Ala Glu Asp Glu Ala Leu Glu
320                 325                 330                 335 ttt cgg cat ata act gaa att acc ata ctt act gtg cag ctt ata gtg     1657
Phe Arg His Ile Thr Glu Ile Thr Ile Leu Thr Val Gln Leu Ile Val
                340                 345                 350 gaa ttt gca aag ggt tta cca gct ttt acc aaa ata cca caa gaa gat     1705
Glu Phe Ala Lys Gly Leu Pro Ala Phe Thr Lys Ile Pro Gln Glu Asp
            355                 360                 365 caa ata aca tta tta aag gca tgt tca agt gaa gta atg atg ctg cga     1753
Gln Ile Thr Leu Leu Lys Ala Cys Ser Ser Glu Val Met Met Leu Arg
            370                 375                 380 atg gct cgg cgg tac gat gca gtg tcg gat tca atc tta ttc gcg aat     1801
Met Ala Arg Arg Tyr Asp Ala Val Ser Asp Ser Ile Leu Phe Ala Asn
385                 390                 395 aat cgt tca tat act cgt gac tcc tat aaa atg gct ggt atg gca gat     1849
Asn Arg Ser Tyr Thr Arg Asp Ser Tyr Lys Met Ala Gly Met Ala Asp
400                 405                 410                 415 aca ata gaa gat cta ttg cat ttt tgt cga cag atg tat act atg act     1897
Thr Ile Glu Asp Leu Leu His Phe Cys Arg Gln Met Tyr Thr Met Thr
                420                 425                 430
```

```
gta gac aat gtg gag tat gca cta ata aca gca att gtg att ttt tca    1945
Val Asp Asn Val Glu Tyr Ala Leu Ile Thr Ala Ile Val Ile Phe Ser
            435                 440                 445 gat cga cct gga ttg gaa caa gca gat ctt gtg gaa caa att caa agt    1993
Asp Arg Pro Gly Leu Glu Gln Ala Asp Leu Val Glu Gln Ile Gln Ser
        450                 455                 460 tat tac atc aaa aca tta aag tgc tac att ttg aat cga cat agt ggt    2041
Tyr Tyr Ile Lys Thr Leu Lys Cys Tyr Ile Leu Asn Arg His Ser Gly
    465                 470                 475 gac cct aag tgt gga ata ttg ttt gcc aaa ctt ctt tct att ctt act    2089
Asp Pro Lys Cys Gly Ile Leu Phe Ala Lys Leu Leu Ser Ile Leu Thr
480                 485                 490                 495 gaa tta cgc acg tta gga aat caa aac tca gaa atg tgt ttt gca ctg    2137
Glu Leu Arg Thr Leu Gly Asn Gln Asn Ser Glu Met Cys Phe Ala Leu
                500                 505                 510 aaa ttg aag aac aga aaa ctt cct aga ttt tta gaa gaa att tgg gat    2185
Lys Leu Lys Asn Arg Lys Leu Pro Arg Phe Leu Glu Glu Ile Trp Asp
            515                 520                 525 gtg aca gat aat gtg cct cct acg ata gac agc atg cat agt gta tcg    2233
Val Thr Asp Asn Val Pro Pro Thr Ile Asp Ser Met His Ser Val Ser
        530                 535                 540 gag aat ttc tat aat aat gaa agt aat ggt acc agt gat tct aca cca    2281
Glu Asn Phe Tyr Asn Asn Glu Ser Asn Gly Thr Ser Asp Ser Thr Pro
    545                 550                 555 atg taa agtgctcaga aaatcaacag ctcttttgca tatttgttta ctgtgtactg     2337
Met
560 gtatggaaaa ttaaggtaac attaaaatat tacataagca ccatgggaaa aggccgttaa   2397 ggcaatattt ttgaataaat aatctattga gacggtacca atggtaaact tggaaaaaat   2457 tcttctgttt acatattagg agccaagtta aagaataagt atgaatgatt gttgataaat   2517 tgcttgtgta acacttcaat ggccttcaat aaaataatgt ttaacaacgt cgataggaaa   2577 ttaaaaagaa atcatgtgta ataaaatcat ttgtaggccg gccatactga tttacctata   2637 ttaagcagaa acttcttaat gtataaatat attttttgctt tgcaaggtaa aaccttctca   2697 atgcaacaat gaattatata tataaacatt gattatttta tcgttagaat ttgaattttg   2757 tgttgtggga gaattgtatt tggattagat aaataggctg tgaaaaataa aaaaaaaaa   2817 aaaaa                                                              2822

<210> SEQ ID NO 6
<211> LENGTH: 560
<212> TYPE: PRT
<213> ORGANISM: Ctenocephalides felis

<400> SEQUENCE: 6

Met Lys Arg Arg Trp Ser Asn Asn Gly Gly Phe Gln Thr Leu Arg Met
1               5                   10                  15

Leu Glu Asp Val Ala Ser Gly Glu Val Thr Ser Ser Ser Gly Gly Ala
            20                  25                  30

Leu Ala Ala Leu Ser Pro Ala Ser Leu Gly Ser Pro Glu Thr Tyr Ala
        35                  40                  45

Glu Leu Asp Leu Trp Val Tyr Glu Glu Ala Gly Leu His Pro Gly Ser
    50                  55                  60

Gly Val Gln Gly Cys Gly Ala Val Ala Ala Leu Pro Ser Ile Ala Thr
65                  70                  75                  80

Gln Val Pro Leu Gly Leu Pro Ala Met Asp Leu Pro His Thr Pro Arg
```

```
                    85                  90                  95
Ser Asp Ser Ala Gly Ser Ile Ser Ser Gly Arg Glu Asp Leu Ser Pro
                100                 105                 110
Pro Ser Ser Leu Asn Gly Tyr Ser Ala Asp Gly Cys Glu Ala Lys Lys
                115                 120                 125
Ala Lys Lys Gly Pro Ala Pro Arg Gln Gln Glu Glu Leu Cys Leu Val
            130                 135             140
Cys Gly Asp Arg Ala Ser Gly Tyr His Tyr Asn Ala Leu Thr Cys Glu
145                 150                 155                 160
Gly Cys Lys Gly Phe Phe Arg Arg Ser Val Thr Lys Asn Ala Val Tyr
                165                 170                 175
Val Cys Lys Phe Gly His Thr Cys Glu Met Asp Met Tyr Met Arg Arg
                180             185                 190
Lys Cys Gln Glu Cys Arg Leu Lys Lys Cys Leu Ala Val Gly Met Arg
            195                 200             205
Pro Glu Cys Val Val Pro Glu Asn Gln Cys Ala Met Lys Arg Lys Glu
        210                 215             220
Lys Lys Ala Gln Lys Glu Lys Asp Ile Gly Pro Ile Ser Gly Thr Val
225                 230             235                 240
Gly Lys Ser Ala Ala Pro Leu Ala Asn Ser Ala Leu Leu Gln Lys Pro
                245                 250                 255
Asp Ile Leu Pro Ala Val Met Lys Cys Asp Pro Leu Pro Pro Glu Ala
                260             265             270
Thr Lys Val Lys Phe Leu Ser Asp Lys Ile Leu Ala Glu Asn Arg Ile
                275             280                 285
Arg Asn Val Pro Pro Leu Thr Ala Asn Gln Glu Tyr Val Ile Ala Arg
            290             295             300
Leu Val Trp Tyr Gln Asp Gly Tyr Glu Gln Pro Ser Glu Glu Asp Leu
305             310             315                 320
Arg Arg Ile Met Ile Ser Thr Pro Ala Glu Asp Glu Ala Leu Glu Phe
                325             330                 335
Arg His Ile Thr Glu Ile Thr Ile Leu Thr Val Gln Leu Ile Val Glu
            340             345                 350
Phe Ala Lys Gly Leu Pro Ala Phe Thr Lys Ile Pro Gln Glu Asp Gln
            355             360                 365
Ile Thr Leu Leu Lys Ala Cys Ser Ser Glu Val Met Met Leu Arg Met
            370             375             380
Ala Arg Arg Tyr Asp Ala Val Ser Asp Ser Ile Leu Phe Ala Asn Asn
385             390                 395                 400
Arg Ser Tyr Thr Arg Asp Ser Tyr Lys Met Ala Gly Met Ala Asp Thr
            405                 410                 415
Ile Glu Asp Leu Leu His Phe Cys Arg Gln Met Tyr Thr Met Thr Val
            420             425                 430
Asp Asn Val Glu Tyr Ala Leu Ile Thr Ala Ile Val Ile Phe Ser Asp
            435                 440                 445
Arg Pro Gly Leu Glu Gln Ala Asp Leu Val Glu Gln Ile Gln Ser Tyr
450                 455                 460
Tyr Ile Lys Thr Leu Lys Cys Tyr Ile Leu Asn Arg His Ser Gly Asp
465                 470                 475                 480
Pro Lys Cys Gly Ile Leu Phe Ala Lys Leu Leu Ser Ile Leu Thr Glu
                485                 490                 495
Leu Arg Thr Leu Gly Asn Gln Asn Ser Glu Met Cys Phe Ala Leu Lys
            500                 505                 510
```

```
Leu Lys Asn Arg Lys Leu Pro Arg Phe Leu Glu Glu Ile Trp Asp Val
        515                 520                 525

Thr Asp Asn Val Pro Pro Thr Ile Asp Ser Met His Ser Val Ser Glu
        530                 535                 540

Asn Phe Tyr Asn Asn Glu Ser Asn Gly Thr Ser Asp Ser Thr Pro Met
545                 550                 555                 560

<210> SEQ ID NO 7
<211> LENGTH: 2822
<212> TYPE: DNA
<213> ORGANISM: Ctenocephalides felis

<400> SEQUENCE: 7
```

| | | | | | |
|---|---|---|---|---|---|
| tttttttttt | tttttttttt | tttcacagcc | tatttatcta | atccaaatac | aattctccca | 60 |
| caacacaaaa | ttcaaattct | aacgataaaa | taatcaatgt | ttatatatat | aattcattgt | 120 |
| tgcattgaga | aggttttacc | ttgcaaagca | aaaatatatt | tatacattaa | gaagtttctg | 180 |
| cttaatatag | gtaaatcagt | atggccggcc | tacaaatgat | tttattacac | atgatttctt | 240 |
| tttaatttcc | tatcgacgtt | gttaaacatt | attttattga | aggccattga | agtgttacac | 300 |
| aagcaattta | tcaacaatca | ttcatactta | ttctttaact | tggctcctaa | tatgtaaaca | 360 |
| gaagaatttt | ttccaagttt | accattggta | ccgtctcaat | agattattta | ttcaaaaata | 420 |
| ttgccttaac | ggccttttcc | catggtgctt | atgtaatatt | ttaatgttac | cttaattttc | 480 |
| cataccagta | cacagtaaac | aaatatgcaa | aagagctgtt | gattttctga | gcactttaca | 540 |
| ttggtgtaga | atcactggta | ccattacttt | cattattata | gaaattctcc | gatacactat | 600 |
| gcatgctgtc | tatcgtagga | ggcacattat | ctgtcacatc | ccaaatttct | tctaaaaatc | 660 |
| taggaagttt | tctgttcttc | aatttcagtg | caaaacacat | ttctgagttt | tgatttccta | 720 |
| acgtgcgtaa | ttcagtaaga | atagaaagaa | gtttggcaaa | caatattcca | cacttagggt | 780 |
| caccactatg | tcgattcaaa | atgtagcact | ttaatgtttt | gatgtaataa | ctttgaattt | 840 |
| gttccacaag | atctgcttgt | tccaatccag | gtcgatctga | aaaaatcaca | attgctgtta | 900 |
| ttagtgcata | ctccacattg | tctacagtca | tagtatacat | ctgtcgacaa | aaatgcaata | 960 |
| gatcttctat | tgtatctgcc | ataccagcca | ttttatagga | gtcacgagta | tatgaacgat | 1020 |
| tattcgcgaa | taagattgaa | tccgacactg | catcgtaccg | ccgagccatt | cgcagcatca | 1080 |
| ttacttcact | tgaacatgcc | tttaataatg | ttatttgatc | ttcttgtggt | attttggtaa | 1140 |
| aagctggtaa | acccttttgca | aattccacta | taagctgcac | agtaagtatg | gtaatttcag | 1200 |
| ttatatgccg | aaattcaaga | gcttcatctt | cagctggtgt | acttatcatt | atccttcgta | 1260 |
| ggtcttcctc | agaaggttgt | tcatatccat | cttggtacca | cactaatctt | gcgatcacat | 1320 |
| attcttgatt | tgcagtcaaa | ggtggaacat | ttcgaattct | gttttcagca | agaatcttgt | 1380 |
| ctgacaaaaa | tttcactta | gttgcttctg | gaggtaatgg | gtcgcatttc | atgaccgcag | 1440 |
| gcaaaatatc | aggcttctga | agtaatgcag | aattcgctaa | gggagcagca | gattttccaa | 1500 |
| cggtacctga | tattggtccg | atgtcctttt | ccttctgtgc | cttcttttcc | tttcgcttca | 1560 |
| tgcgcattg | gttttcggga | accacgcact | cggggcgcat | tccgacagcc | aaacatttct | 1620 |
| tgagcctaca | ttcctgacat | ttgcgtcgca | tatacatgtc | catttcgcac | gtgtgcccaa | 1680 |
| acttgcacac | gtacacggca | ttcttagtca | cacttcgtcg | gaaaaaacct | ttgcatcctt | 1740 |
| cacaagtaag | agcgttgtaa | tgatatccgg | aggcacggtc | gccgcacaca | agacatagtt | 1800 |
| cctcctgctg | ccgcggcgcc | ggcccttttct | tggccttctt | cgcttcgcag | ccatctgctg | 1860 |

-continued

```
aatagccgtt caaagaacta ggcggtgaca ggtcttctcg tcctgatgag atgctacccg    1920
cactgtcact ccgaggcgtg tgcggtaggt ccatagcggg caatcctagg gggacctgtg    1980
tcgcgatcga tggcaaggcg gcgaccgcac cgcatccttg cacacctgaa cctggatgta    2040
agccagcttc ctcgtacacc cacaaatcca gctcggcata tgtctcgggc gaacctaacg    2100
aagccggact caacgcagcc agggcgccac cagaagacga cgttacctca ccagatgcaa    2160
catcttcgag catccgcaag gtttggaagc caccgttgtt agaccaacgt cgtttcatgt    2220
tgataatgca aggtatttca cttcacacat ttatccttta gaagatcacc atacacaaat    2280
tgaaaatata gtgattttta tttatgactg acataacatc cttaggaata tagtcatctt    2340
attgcagatt ttactcgaaa gcatttctca actcctaatt cataattgaa tctctgtacc    2400
taatgtgtgt gactgtaaaa tctaattgta tcattttgag tatataattt aatgattaaa    2460
atgattataa ttacttttcc tcttagtttc aaaatctttt gtatattaat ttatattcat    2520
agttagaaag tatttatgta aaattttaaa ttttacaaaa caaataaaat aaataaataa    2580
tatcttaaaa gcataaaata ggtaacttgg atgaatgttt aaaatttgtt attgacatat    2640
gaacataata tgttctattt caatataaaa aaattgttta attatcattt ctgattgata    2700
gagcggcata cgaatcagtt tttaggtagc atgtgtttca tttcacaaat acaattatac    2760
atataattgt taatggttat atataattag tgatatgagc atgtgcgtct tgtatatata    2820
gc                                                                    2822
```

<210> SEQ ID NO 8
<211> LENGTH: 1680
<212> TYPE: DNA
<213> ORGANISM: Ctenocephalides felis
<220> FEATURE:
<221> NAME/KEY: CDS
<222> LOCATION: (1)..(1680)
<223> OTHER INFORMATION:

<400> SEQUENCE: 8

```
atg aaa cga cgt tgg tct aac aac ggt ggc ttc caa acc ttg cgg atg         48
Met Lys Arg Arg Trp Ser Asn Asn Gly Gly Phe Gln Thr Leu Arg Met
1               5                  10                  15 ctc gaa gat gtt gca tct ggt gag gta acg tcg tct tct ggt ggc gcc         96
Leu Glu Asp Val Ala Ser Gly Glu Val Thr Ser Ser Ser Gly Gly Ala
            20                  25                  30 ctg gct gcg ttg agt ccg gct tcg tta ggt tcg ccc gag aca tat gcc        144
Leu Ala Ala Leu Ser Pro Ala Ser Leu Gly Ser Pro Glu Thr Tyr Ala
        35                  40                  45 gag ctg gat ttg tgg gtg tac gag gaa gct ggc tta cat cca ggt tca        192
Glu Leu Asp Leu Trp Val Tyr Glu Glu Ala Gly Leu His Pro Gly Ser
    50                  55                  60 ggt gtg caa gga tgc ggt gcg gtc gcc gcc ttg cca tcg atc gcg aca        240
Gly Val Gln Gly Cys Gly Ala Val Ala Ala Leu Pro Ser Ile Ala Thr
65                  70                  75                  80 cag gtc ccc cta gga ttg ccc gct atg gac cta ccg cac acg cct cgg        288
Gln Val Pro Leu Gly Leu Pro Ala Met Asp Leu Pro His Thr Pro Arg
                85                  90                  95 agt gac agt gcg ggt agc atc tca tca gga cga gaa gac ctg tca ccg        336
Ser Asp Ser Ala Gly Ser Ile Ser Ser Gly Arg Glu Asp Leu Ser Pro
            100                 105                 110 cct agt tct ttg aac ggc tat tca gca gat ggc tgc gaa gcg aag aag        384
Pro Ser Ser Leu Asn Gly Tyr Ser Ala Asp Gly Cys Glu Ala Lys Lys
        115                 120                 125
```

```
gcc aag aaa ggg ccg gcg ccg cgg cag cag gag gaa cta tgt ctt gtg    432
Ala Lys Lys Gly Pro Ala Pro Arg Gln Gln Glu Glu Leu Cys Leu Val
    130             135                 140 tgc ggc gac cgt gcc tcc gga tat cat tac aac gct ctt act tgt gaa    480
Cys Gly Asp Arg Ala Ser Gly Tyr His Tyr Asn Ala Leu Thr Cys Glu
145                 150                 155                 160 gga tgc aaa ggt ttt ttc cga cga agt gtg act aag aat gcc gtg tac    528
Gly Cys Lys Gly Phe Phe Arg Arg Ser Val Thr Lys Asn Ala Val Tyr
                165                 170                 175 gtg tgc aag ttt ggg cac acg tgc gaa atg gac atg tat atg cga cgc    576
Val Cys Lys Phe Gly His Thr Cys Glu Met Asp Met Tyr Met Arg Arg
                180                 185                 190 aaa tgt cag gaa tgt agg ctc aag aaa tgt ttg gct gtc gga atg cgc    624
Lys Cys Gln Glu Cys Arg Leu Lys Lys Cys Leu Ala Val Gly Met Arg
            195                 200                 205 ccc gag tgc gtg gtt ccc gaa aac caa tgc gcc atg aag cga aag gaa    672
Pro Glu Cys Val Val Pro Glu Asn Gln Cys Ala Met Lys Arg Lys Glu
        210                 215                 220 aag aag gca cag aag gaa aag gac atc gga cca ata tca ggt acc gtt    720
Lys Lys Ala Gln Lys Glu Lys Asp Ile Gly Pro Ile Ser Gly Thr Val
225                 230                 235                 240 gga aaa tct gct gct ccc tta gcg aat tct gca tta ctt cag aag cct    768
Gly Lys Ser Ala Ala Pro Leu Ala Asn Ser Ala Leu Leu Gln Lys Pro
                245                 250                 255 gat att ttg cct gcg gtc atg aaa tgc gac cca tta cct cca gaa gca    816
Asp Ile Leu Pro Ala Val Met Lys Cys Asp Pro Leu Pro Pro Glu Ala
                260                 265                 270 act aaa gtg aaa ttt ttg tca gac aag att ctt gct gaa aac aga att    864
Thr Lys Val Lys Phe Leu Ser Asp Lys Ile Leu Ala Glu Asn Arg Ile
                275                 280                 285 cga aat gtt cca cct ttg act gca aat caa gaa tat gtg atc gca aga    912
Arg Asn Val Pro Pro Leu Thr Ala Asn Gln Glu Tyr Val Ile Ala Arg
        290                 295                 300 tta gtg tgg tac caa gat gga tat gaa caa cct tct gag gaa gac cta    960
Leu Val Trp Tyr Gln Asp Gly Tyr Glu Gln Pro Ser Glu Glu Asp Leu
305                 310                 315                 320 cga agg ata atg ata agt aca cca gct gaa gat gaa gct ctt gaa ttt   1008
Arg Arg Ile Met Ile Ser Thr Pro Ala Glu Asp Glu Ala Leu Glu Phe
                325                 330                 335 cgg cat ata act gaa att acc ata ctt act gtg cag ctt ata gtg gaa   1056
Arg His Ile Thr Glu Ile Thr Ile Leu Thr Val Gln Leu Ile Val Glu
                340                 345                 350 ttt gca aag ggt tta cca gct ttt acc aaa ata cca caa gaa gat caa   1104
Phe Ala Lys Gly Leu Pro Ala Phe Thr Lys Ile Pro Gln Glu Asp Gln
            355                 360                 365 ata aca tta tta aag gca tgt tca agt gaa gta atg atg ctg cga atg   1152
Ile Thr Leu Leu Lys Ala Cys Ser Ser Glu Val Met Met Leu Arg Met
        370                 375                 380 gct cgg cgg tac gat gca gtg tcg gat tca atc tta ttc gcg aat aat   1200
Ala Arg Arg Tyr Asp Ala Val Ser Asp Ser Ile Leu Phe Ala Asn Asn
385                 390                 395                 400 cgt tca tat act cgt gac tcc tat aaa atg gct ggt atg gca gat aca   1248
Arg Ser Tyr Thr Arg Asp Ser Tyr Lys Met Ala Gly Met Ala Asp Thr
                405                 410                 415 ata gaa gat cta ttg cat ttt tgt cga cag atg tat act atg act gta   1296
Ile Glu Asp Leu Leu His Phe Cys Arg Gln Met Tyr Thr Met Thr Val
                420                 425                 430 gac aat gtg gag tat gca cta ata aca gca att gtg att ttt tca gat   1344
Asp Asn Val Glu Tyr Ala Leu Ile Thr Ala Ile Val Ile Phe Ser Asp
                435                 440                 445
```

```
cga cct gga ttg gaa caa gca gat ctt gtg gaa caa att caa agt tat      1392
Arg Pro Gly Leu Glu Gln Ala Asp Leu Val Glu Gln Ile Gln Ser Tyr
    450                 455                 460 tac atc aaa aca tta aag tgc tac att ttg aat cga cat agt ggt gac      1440
Tyr Ile Lys Thr Leu Lys Cys Tyr Ile Leu Asn Arg His Ser Gly Asp
465                 470                 475                 480 cct aag tgt gga ata ttg ttt gcc aaa ctt ctt tct att ctt act gaa      1488
Pro Lys Cys Gly Ile Leu Phe Ala Lys Leu Leu Ser Ile Leu Thr Glu
            485                 490                 495 tta cgc acg tta gga aat caa aac tca gaa atg tgt ttt gca ctg aaa      1536
Leu Arg Thr Leu Gly Asn Gln Asn Ser Glu Met Cys Phe Ala Leu Lys
        500                 505                 510 ttg aag aac aga aaa ctt cct aga ttt tta gaa gaa att tgg gat gtg      1584
Leu Lys Asn Arg Lys Leu Pro Arg Phe Leu Glu Glu Ile Trp Asp Val
    515                 520                 525 aca gat aat gtg cct cct acg ata gac agc atg cat agt gta tcg gag      1632
Thr Asp Asn Val Pro Pro Thr Ile Asp Ser Met His Ser Val Ser Glu
530                 535                 540 aat ttc tat aat aat gaa agt aat ggt acc agt gat tct aca cca atg      1680
Asn Phe Tyr Asn Asn Glu Ser Asn Gly Thr Ser Asp Ser Thr Pro Met
545                 550                 555                 560

<210> SEQ ID NO 9
<211> LENGTH: 560
<212> TYPE: PRT
<213> ORGANISM: Ctenocephalides felis

<400> SEQUENCE: 9

Met Lys Arg Arg Trp Ser Asn Asn Gly Gly Phe Gln Thr Leu Arg Met
1               5                   10                  15

Leu Glu Asp Val Ala Ser Gly Glu Val Thr Ser Ser Ser Gly Gly Ala
                20                  25                  30

Leu Ala Ala Leu Ser Pro Ala Ser Leu Gly Ser Pro Glu Thr Tyr Ala
            35                  40                  45

Glu Leu Asp Leu Trp Val Tyr Glu Glu Ala Gly Leu His Pro Gly Ser
        50                  55                  60

Gly Val Gln Gly Cys Gly Ala Val Ala Ala Leu Pro Ser Ile Ala Thr
65                  70                  75                  80

Gln Val Pro Leu Gly Leu Pro Ala Met Asp Leu Pro His Thr Pro Arg
                85                  90                  95

Ser Asp Ser Ala Gly Ser Ile Ser Ser Gly Arg Glu Asp Leu Ser Pro
            100                 105                 110

Pro Ser Ser Leu Asn Gly Tyr Ser Ala Asp Gly Cys Glu Ala Lys Lys
        115                 120                 125

Ala Lys Lys Gly Pro Ala Pro Arg Gln Gln Glu Glu Leu Cys Leu Val
    130                 135                 140

Cys Gly Asp Arg Ala Ser Gly Tyr His Tyr Asn Ala Leu Thr Cys Glu
145                 150                 155                 160

Gly Cys Lys Gly Phe Phe Arg Arg Ser Val Thr Lys Asn Ala Val Tyr
                165                 170                 175

Val Cys Lys Phe Gly His Thr Cys Glu Met Asp Met Tyr Met Arg Arg
            180                 185                 190

Lys Cys Gln Glu Cys Arg Leu Lys Lys Cys Leu Ala Val Gly Met Arg
        195                 200                 205

Pro Glu Cys Val Val Pro Glu Asn Gln Cys Ala Met Lys Arg Lys Glu
    210                 215                 220
```

| | | | | | | | | | | | | | | |
|---|---|---|---|---|---|---|---|---|---|---|---|---|---|---|
| Lys | Lys | Ala | Gln | Lys | Glu | Lys | Asp | Ile | Gly | Pro | Ile | Ser | Gly | Thr | Val |
| 225 | | | | 230 | | | | 235 | | | | 240 | | |

| Gly | Lys | Ser | Ala | Ala | Pro | Leu | Ala | Asn | Ser | Ala | Leu | Leu | Gln | Lys | Pro |
|---|---|---|---|---|---|---|---|---|---|---|---|---|---|---|---|
| | | | 245 | | | | | 250 | | | | | 255 | | |

| Asp | Ile | Leu | Pro | Ala | Val | Met | Lys | Cys | Asp | Pro | Leu | Pro | Pro | Glu | Ala |
|---|---|---|---|---|---|---|---|---|---|---|---|---|---|---|---|
| | | | 260 | | | | | 265 | | | | | 270 | | |

| Thr | Lys | Val | Lys | Phe | Leu | Ser | Asp | Lys | Ile | Leu | Ala | Glu | Asn | Arg | Ile |
|---|---|---|---|---|---|---|---|---|---|---|---|---|---|---|---|
| | | 275 | | | | | 280 | | | | | 285 | | | |

| Arg | Asn | Val | Pro | Pro | Leu | Thr | Ala | Asn | Gln | Glu | Tyr | Val | Ile | Ala | Arg |
|---|---|---|---|---|---|---|---|---|---|---|---|---|---|---|---|
| | 290 | | | | | 295 | | | | | 300 | | | | |

| Leu | Val | Trp | Tyr | Gln | Asp | Gly | Tyr | Glu | Gln | Pro | Ser | Glu | Glu | Asp | Leu |
|---|---|---|---|---|---|---|---|---|---|---|---|---|---|---|---|
| 305 | | | | | 310 | | | | | 315 | | | | | 320 |

| Arg | Arg | Ile | Met | Ile | Ser | Thr | Pro | Ala | Glu | Asp | Glu | Ala | Leu | Glu | Phe |
|---|---|---|---|---|---|---|---|---|---|---|---|---|---|---|---|
| | | | | 325 | | | | | 330 | | | | | 335 | |

| Arg | His | Ile | Thr | Glu | Ile | Thr | Ile | Leu | Thr | Val | Gln | Leu | Ile | Val | Glu |
|---|---|---|---|---|---|---|---|---|---|---|---|---|---|---|---|
| | | | 340 | | | | | 345 | | | | | 350 | | |

| Phe | Ala | Lys | Gly | Leu | Pro | Ala | Phe | Thr | Lys | Ile | Pro | Gln | Glu | Asp | Gln |
|---|---|---|---|---|---|---|---|---|---|---|---|---|---|---|---|
| | | 355 | | | | | 360 | | | | | 365 | | | |

| Ile | Thr | Leu | Leu | Lys | Ala | Cys | Ser | Ser | Glu | Val | Met | Met | Leu | Arg | Met |
|---|---|---|---|---|---|---|---|---|---|---|---|---|---|---|---|
| 370 | | | | | 375 | | | | | 380 | | | | | |

| Ala | Arg | Arg | Tyr | Asp | Ala | Val | Ser | Asp | Ser | Ile | Leu | Phe | Ala | Asn | Asn |
|---|---|---|---|---|---|---|---|---|---|---|---|---|---|---|---|
| 385 | | | | | 390 | | | | | 395 | | | | | 400 |

| Arg | Ser | Tyr | Thr | Arg | Asp | Ser | Tyr | Lys | Met | Ala | Gly | Met | Ala | Asp | Thr |
|---|---|---|---|---|---|---|---|---|---|---|---|---|---|---|---|
| | | | | 405 | | | | | 410 | | | | | 415 | |

| Ile | Glu | Asp | Leu | Leu | His | Phe | Cys | Arg | Gln | Met | Tyr | Thr | Met | Thr | Val |
|---|---|---|---|---|---|---|---|---|---|---|---|---|---|---|---|
| | | | | 420 | | | | | 425 | | | | | 430 | |

| Asp | Asn | Val | Glu | Tyr | Ala | Leu | Ile | Thr | Ala | Ile | Val | Ile | Phe | Ser | Asp |
|---|---|---|---|---|---|---|---|---|---|---|---|---|---|---|---|
| | | 435 | | | | | 440 | | | | | 445 | | | |

| Arg | Pro | Gly | Leu | Glu | Gln | Ala | Asp | Leu | Val | Glu | Gln | Ile | Gln | Ser | Tyr |
|---|---|---|---|---|---|---|---|---|---|---|---|---|---|---|---|
| | 450 | | | | | 455 | | | | | 460 | | | | |

| Tyr | Ile | Lys | Thr | Leu | Lys | Cys | Tyr | Ile | Leu | Asn | Arg | His | Ser | Gly | Asp |
|---|---|---|---|---|---|---|---|---|---|---|---|---|---|---|---|
| 465 | | | | | 470 | | | | | 475 | | | | | 480 |

| Pro | Lys | Cys | Gly | Ile | Leu | Phe | Ala | Lys | Leu | Leu | Ser | Ile | Leu | Thr | Glu |
|---|---|---|---|---|---|---|---|---|---|---|---|---|---|---|---|
| | | | | 485 | | | | | 490 | | | | | 495 | |

| Leu | Arg | Thr | Leu | Gly | Asn | Gln | Asn | Ser | Glu | Met | Cys | Phe | Ala | Leu | Lys |
|---|---|---|---|---|---|---|---|---|---|---|---|---|---|---|---|
| | | | 500 | | | | | 505 | | | | | 510 | | |

| Leu | Lys | Asn | Arg | Lys | Leu | Pro | Arg | Phe | Leu | Glu | Glu | Ile | Trp | Asp | Val |
|---|---|---|---|---|---|---|---|---|---|---|---|---|---|---|---|
| | | 515 | | | | | 520 | | | | | 525 | | | |

| Thr | Asp | Asn | Val | Pro | Pro | Thr | Ile | Asp | Ser | Met | His | Ser | Val | Ser | Glu |
|---|---|---|---|---|---|---|---|---|---|---|---|---|---|---|---|
| | 530 | | | | | 535 | | | | | 540 | | | | |

| Asn | Phe | Tyr | Asn | Asn | Glu | Ser | Asn | Gly | Thr | Ser | Asp | Ser | Thr | Pro | Met |
|---|---|---|---|---|---|---|---|---|---|---|---|---|---|---|---|
| 545 | | | | | 550 | | | | | 555 | | | | | 560 |

<210> SEQ ID NO 10
<211> LENGTH: 1680
<212> TYPE: DNA
<213> ORGANISM: Ctenocephalides felis

<400> SEQUENCE: 10

```
cattggtgta gaatcactgg taccattact ttcattatta tagaaattct ccgatacact    60
atgcatgctg tctatcgtag gaggcacatt atctgtcaca tcccaaattt cttctaaaaa   120
tctaggaagt tttctgttct tcaatttcag tgcaaaacac atttctgagt tttgatttcc   180
taacgtgcgt aattcagtaa gaatagaaag aagtttggca acaatattc cacacttagg    240
```

```
gtcaccacta tgtcgattca aaatgtagca ctttaatgtt ttgatgtaat aactttgaat      300
ttgttccaca agatctgctt gttccaatcc aggtcgatct gaaaaaatca caattgctgt      360
tattagtgca tactccacat tgtctacagt catagtatac atctgtcgac aaaaatgcaa      420
tagatcttct attgtatctg ccataccagc cattttatag gagtcacgag tatatgaacg      480
attattcgcg aataagattg aatccgacac tgcatcgtac cgccgagcca ttcgcagcat      540
cattacttca cttgaacatg cctttaataa tgttatttga tcttcttgtg gtattttggt      600
aaaagctggt aaacccttttg caaattccac tataagctgc acagtaagta tggtaatttc      660
agttatatgc cgaaattcaa gagcttcatc ttcagctggt gtacttatca ttatccttcg      720
taggtcttcc tcagaaggtt gttcatatcc atcttggtac cacactaatc ttgcgatcac      780
atattcttga tttgcagtca aaggtggaac atttcgaatt ctgttttcag caagaatctt      840
gtctgacaaa aatttcactt tagttgcttc tggaggtaat gggtcgcatt tcatgaccgc      900
aggcaaaata tcaggcttct gaagtaatgc agaattcgct aagggagcag cagatttttcc     960
aacggtacct gatattggtc cgatgtcctt ttccttctgt gccttctttt cctttcgctt     1020
catggcgcat tggttttcgg gaaccacgca ctcggggcgc attccgacag ccaaacattt     1080
cttgagccta cattcctgac atttgcgtcg catatacatg tccatttcgc acgtgtgccc     1140
aaacttgcac acgtacacgg cattcttagt cacacttcgt cggaaaaaac ctttgcatcc     1200
ttcacaagta agagcgttgt aatgatatcc ggaggcacgg tcgccgcaca aagacatag      1260
ttcctcctgc tgccgcggcg ccggcccttt cttggccttc ttcgcttcgc agccatctgc     1320
tgaatagccg ttcaaagaac taggcggtga caggtcttct cgtcctgatg agatgctacc     1380
cgcactgtca ctccgaggcg tgtgcggtag gtccatagcg ggcaatccta gggggacctg     1440
tgtcgcgatc gatggcaagg cggcgaccgc accgcatcct tgcacacctg aacctggatg     1500
taagccagct cctcgtaca cccacaaatc cagctcggca tatgtctcgg gcgaacctaa      1560
cgaagccgga ctcaacgcag ccagggcgcc accagaagac gacgttacct caccagatgc     1620
aacatcttcg agcatccgca aggtttggaa gccaccgttg ttagaccaac gtcgtttcat     1680
```

<210> SEQ ID NO 11
<211> LENGTH: 666
<212> TYPE: DNA
<213> ORGANISM: Ctenocephalides felis
<400> SEQUENCE: 11

```
atttgcatta cggtatattt aaatttaaaa ctccacatgt attgacaaaa aataagtaaa       60
aaaatagttc attgaatata atacggtttc attcgtaatg tttcgagcgg ttacaaatct      120
tgcaaattct tctgatggaa ctgttttgaa cgaagttata catgaagatc ttctgcttaa      180
atgtgaaccc tctactagcg tggacgcatt atctaatgga gctttcggta gcaagcagca      240
gcacaaagtc gaagaatgga agcgatcacc tagtcccagt ttgacgaaca gccatgtgcc      300
acctctcaca ccatcaccag gcccatccag cttaccatat tcgacattgt ctaatggcta      360
ttcttcgcca atgtcgtcag gcagctgcga tccctatagc cctaatggta aaatgggacg      420
agaagacctg tcaccgccta gttctttgaa cggctattca gcagatggct gcgaagcgaa      480
gaaggccaag aaagggccgg cgccgcggca acaggaggaa ctatgtcttg tgtgcggcga      540
ccgtgcctcc ggatatcatt acaacgctct tacttgtgaa ggatgcaaag ggttttttccg     600
acgaagtgtg actaagaatg ccgtgtacgt gttcaagttt gggcacacgt gcgaaaatgg      660
acatgt                                                                666
```

-continued

<210> SEQ ID NO 12
<211> LENGTH: 666
<212> TYPE: DNA
<213> ORGANISM: Ctenocephalides felis

<400> SEQUENCE: 12

| | | | | | |
|---|---|---|---|---|---|
| acatgtccat | tttcgcacgt | gtgcccaaac | ttgaacacgt | acacggcatt | cttagtcaca | 60 |
| cttcgtcgga | aaaacccttt | gcatccttca | caagtaagag | cgttgtaatg | atatccggag | 120 |
| gcacggtcgc | cgcacacaag | acatagttcc | tcctgttgcc | gcggcgccgg | ccctttcttg | 180 |
| gccttcttcg | cttcgcagcc | atctgctgaa | tagccgttca | agaactagg | cggtgacagg | 240 |
| tcttctcgtc | ccattttacc | attagggcta | tagggatcgc | agctgcctga | cgacattggc | 300 |
| gaagaatagc | cattagacaa | tgtcgaatat | ggtaagctgg | atgggcctgg | tgatggtgtg | 360 |
| agaggtggca | catggctgtt | cgtcaaactg | ggactaggtg | atcgcttcca | ttcttcgact | 420 |
| tgtgctgct | gcttgctacc | gaaagctcca | ttagataatg | cgtccacgct | agtagagggt | 480 |
| tcacatttaa | gcagaagatc | ttcatgtata | acttcgttca | aaacagttcc | atcagaagaa | 540 |
| tttgcaagat | ttgtaaccgc | tcgaaacatt | acgaatgaaa | ccgtattata | ttcaatgaac | 600 |
| tatttttta | cttattttt | gtcaatacat | gtggagtttt | aaatttaaat | ataccgtaat | 660 |
| gcaaat | | | | | | 666 |

<210> SEQ ID NO 13
<211> LENGTH: 4148
<212> TYPE: DNA
<213> ORGANISM: Ctenocephalides felis
<220> FEATURE:
<221> NAME/KEY: CDS
<222> LOCATION: (184)..(1869)
<223> OTHER INFORMATION:

<400> SEQUENCE: 13

```
taaagggaac aaaagctgga gctccaccgc ggtggcggcc gctctagaac tagtggatcc      60
cccgggctgc aggaattcgg cacgagattt gcattacggt atatttaaat ttaaaactcc     120
acatgtattg acaaaaaata agtaaaaaaa tagttcattg aatataatac ggtttcattc     180 gta atg ttt cga gcg gtt aca aat ctt gca aat tct tct gat gga act       228
    Met Phe Arg Ala Val Thr Asn Leu Ala Asn Ser Ser Asp Gly Thr
    1               5                   10                  15 gtt ttg aac gaa gtt ata cat gaa gat ctt ctg ctt aaa tgt gaa ccc       276
Val Leu Asn Glu Val Ile His Glu Asp Leu Leu Leu Lys Cys Glu Pro
            20                  25                  30 tct act agc gtg gac gca tta tct aat gga gct ttc ggt agc aag cag       324
Ser Thr Ser Val Asp Ala Leu Ser Asn Gly Ala Phe Gly Ser Lys Gln
        35                  40                  45 cag cac aaa gtc gaa gaa tgg aag cga tca cct agt ccc agt ttg acg       372
Gln His Lys Val Glu Glu Trp Lys Arg Ser Pro Ser Pro Ser Leu Thr
    50                  55                  60 aac agc cat gtg cca cct ctc aca cca tca cca ggc cca tcc agc tta       420
Asn Ser His Val Pro Pro Leu Thr Pro Ser Pro Gly Pro Ser Ser Leu
65                  70                  75 cca tat tcg aca ttg tct aat ggc tat tct tcg cca atg tcg tca ggc       468
Pro Tyr Ser Thr Leu Ser Asn Gly Tyr Ser Ser Pro Met Ser Ser Gly
80                  85                  90                  95 agc tgc gat ccc tat agc cct aat ggt aaa atg gga cga gaa gac ctg       516
Ser Cys Asp Pro Tyr Ser Pro Asn Gly Lys Met Gly Arg Glu Asp Leu
                100                 105                 110
```

-continued

```
tca ccg cct agt tct ttg aac ggc tat tca gca gat ggc tgc gaa gcg        564
Ser Pro Pro Ser Ser Leu Asn Gly Tyr Ser Ala Asp Gly Cys Glu Ala
            115                 120                 125 aag aag gcc aag aaa ggg ccg gcg ccg cgg cag cag gag gaa cta tgt        612
Lys Lys Ala Lys Lys Gly Pro Ala Pro Arg Gln Gln Glu Glu Leu Cys
        130                 135                 140 ctt gtg tgc ggc gac cgt gcc tcc gga tat cat tac aac gct ctt act        660
Leu Val Cys Gly Asp Arg Ala Ser Gly Tyr His Tyr Asn Ala Leu Thr
145                 150                 155 tgt gaa gga tgc aaa ggt ttt ttc cga cga agt gtg act aag aat gcc        708
Cys Glu Gly Cys Lys Gly Phe Phe Arg Arg Ser Val Thr Lys Asn Ala
160                 165                 170                 175 gtg tac gtg tgc aag ttt ggg cac acg tgc gaa atg gac atg tat atg        756
Val Tyr Val Cys Lys Phe Gly His Thr Cys Glu Met Asp Met Tyr Met
                180                 185                 190 cga cgc aaa tgt cag gaa tgt agg ctc aag aaa tgt ttg gct gtc gga        804
Arg Arg Lys Cys Gln Glu Cys Arg Leu Lys Lys Cys Leu Ala Val Gly
            195                 200                 205 atg cgc ccc gag tgc gtg gtt ccc gaa aac caa tgc gcc atg aag cga        852
Met Arg Pro Glu Cys Val Val Pro Glu Asn Gln Cys Ala Met Lys Arg
        210                 215                 220 aag gaa aag aag gca cag aag gaa aag gac atc gga cca ata tca ggt        900
Lys Glu Lys Lys Ala Gln Lys Glu Lys Asp Ile Gly Pro Ile Ser Gly
225                 230                 235 acc gtt gga aaa tct gct gct ccc cta gcg aat tct gca tta ctt cag        948
Thr Val Gly Lys Ser Ala Ala Pro Leu Ala Asn Ser Ala Leu Leu Gln
240                 245                 250                 255 aag cct gat att ttg cct gcg gtc atg aaa tgc gac cca tta cct cca        996
Lys Pro Asp Ile Leu Pro Ala Val Met Lys Cys Asp Pro Leu Pro Pro
                260                 265                 270 gaa gca act aaa gtg aaa ttt ttg tca gac aag att ctt gct gaa aac       1044
Glu Ala Thr Lys Val Lys Phe Leu Ser Asp Lys Ile Leu Ala Glu Asn
            275                 280                 285 aga att cga aat gtt cca cct ttg act gca aat caa gaa tat gtg atc       1092
Arg Ile Arg Asn Val Pro Pro Leu Thr Ala Asn Gln Glu Tyr Val Ile
        290                 295                 300 gca aga tta gtg tgg tac caa gat gga tat gaa caa cct tct gag gaa       1140
Ala Arg Leu Val Trp Tyr Gln Asp Gly Tyr Glu Gln Pro Ser Glu Glu
305                 310                 315 gac cta cga agg ata atg ata agt aca cca gct gaa gat gaa gct ctt       1188
Asp Leu Arg Arg Ile Met Ile Ser Thr Pro Ala Glu Asp Glu Ala Leu
320                 325                 330                 335 gaa ttt cgg cat ata act gaa att acc ata ctt act gtg cag ctt ata       1236
Glu Phe Arg His Ile Thr Glu Ile Thr Ile Leu Thr Val Gln Leu Ile
                340                 345                 350 gtg gaa ttt gca aag ggt tta cca gct ttt acc aaa ata cca caa gaa       1284
Val Glu Phe Ala Lys Gly Leu Pro Ala Phe Thr Lys Ile Pro Gln Glu
            355                 360                 365 gat caa ata aca tta tta aag gca tgt tca agt gaa gta atg atg ctg       1332
Asp Gln Ile Thr Leu Leu Lys Ala Cys Ser Ser Glu Val Met Met Leu
        370                 375                 380 cga atg gct cgg cgg tac gat gca gtg tcg gat tca atc tta ttc gcg       1380
Arg Met Ala Arg Arg Tyr Asp Ala Val Ser Asp Ser Ile Leu Phe Ala
385                 390                 395 aat aat cgt tca tat act cgt gac tcc tat aaa atg gct ggt atg gca       1428
Asn Asn Arg Ser Tyr Thr Arg Asp Ser Tyr Lys Met Ala Gly Met Ala
400                 405                 410                 415 gat aca ata gaa gat cta ttg cat ttt tgt cga cag atg tat act atg       1476
Asp Thr Ile Glu Asp Leu Leu His Phe Cys Arg Gln Met Tyr Thr Met
                420                 425                 430
```

| | | |
|---|---|---|
| act gta gac aat gtg gag tat gca cta ata aca gca att gtg att ttt<br>Thr Val Asp Asn Val Glu Tyr Ala Leu Ile Thr Ala Ile Val Ile Phe<br>435 440 445 | | 1524 |
| tca gat cga cct gga ttg gaa caa gca gat ctt gtg gaa caa att caa<br>Ser Asp Arg Pro Gly Leu Glu Gln Ala Asp Leu Val Glu Gln Ile Gln<br>450 455 460 | | 1572 |
| agt tat tac atc aaa aca tta aag tgc tac att ttg aat cga cat agt<br>Ser Tyr Tyr Ile Lys Thr Leu Lys Cys Tyr Ile Leu Asn Arg His Ser<br>465 470 475 | | 1620 |
| ggt gac cct aag tgt gga ata ttg ttt gcc aaa ctt ctt tct att ctt<br>Gly Asp Pro Lys Cys Gly Ile Leu Phe Ala Lys Leu Leu Ser Ile Leu<br>480 485 490 495 | | 1668 |
| act gaa tta cgc acg tta gga aat caa aac tca gaa atg tgt ttt gca<br>Thr Glu Leu Arg Thr Leu Gly Asn Gln Asn Ser Glu Met Cys Phe Ala<br>500 505 510 | | 1716 |
| ctg aaa ttg aag aac aga aaa ctt cct aga ttt tta gaa gaa att tgg<br>Leu Lys Leu Lys Asn Arg Lys Leu Pro Arg Phe Leu Glu Glu Ile Trp<br>515 520 525 | | 1764 |
| gat gtg aca gat aat gtg cct cct acg ata gac agc atg cat agt gta<br>Asp Val Thr Asp Asn Val Pro Pro Thr Ile Asp Ser Met His Ser Val<br>530 535 540 | | 1812 |
| tcg gag aat ttc tat aat aat gaa agt aat ggt acc agt gat tct aca<br>Ser Glu Asn Phe Tyr Asn Asn Glu Ser Asn Gly Thr Ser Asp Ser Thr<br>545 550 555 | | 1860 |
| ccg atg taa agtgctcaga aaatcaacag ctcttttgca tatttgttta<br>Pro Met<br>560 | | 1909 |
| ctgtgtactg gtatggaaaa ttaaggtatc attaaaatat tacataagca ccatgggaaa | | 1969 |
| aggccgttaa ggcaatattt ttgaatatat aatctattga gacgatacca atggtaaact | | 2029 |
| tggaaaaatc tctgttacat attaagagcc aagttaaaga taatgtgaag gatggtgata | | 2089 |
| tatgctgtgt acactcaatg gccttattaa aataaggtta caccctcgata ggaaattaaa | | 2149 |
| aagaaatcat gtgtaataaa atcatttgta ggccggccat actgatttac ctatattaag | | 2209 |
| cagaaacttc ttattgtata aatatatttt tgctttgcaa ggtaaaacct tctcaatgca | | 2269 |
| acaatgaatt atatataaac attgattatt ttatcgttag aatttgaatt ttgtgttgtg | | 2329 |
| ggagaattgt atttggatta gataaatagg ctgtgaaaaa taatttaatt ctatatcctc | | 2389 |
| aaaataccta tacattatat tgacctccat ttgaaatcat ctgacaaagg aagctataat | | 2449 |
| tgctgcaacc ctcacacgag aatacatata taaatactac acatagtgct caagtagcta | | 2509 |
| taatgatata aattaacata tttccaaaat agattcaagt atttttagcc tcattcattt | | 2569 |
| tttaccttag aaatttgcaa gttttattca aaattatata aattcattcc gaaaccatac | | 2629 |
| agtgctcttg tcaaatgctg ctgctgtaac ttgtatatgt ttgtttatgt aattaatgct | | 2689 |
| tcatataaat ttatgctgtt taagacatta tgtgtaatat attatcaccc tcttttattag | | 2749 |
| ttagaatata tgtatttta taagtttgac gatagaatgt tttaaagtta ttttcagact | | 2809 |
| ggccctctta tcaaatgatt ttaaataaag ggtttctcaa ttcacatgtg atgattcatc | | 2869 |
| taacgttaga tcatatttga atgctagttc attaaatatt tgtaaggaaa atgatacaaa | | 2929 |
| gtatgccatt gtttggtgtt ccaactactt taataatatt tgccaaattc tctctcaaaa | | 2989 |
| gttaatgatt tttattattt taatcaatta tctactttgt agttcatgta tggcatatca | | 3049 |
| atataagtat gcgtgtgcta taataatttt gaacgttgca ccataattaa gtgttcaaaa | | 3109 |
| tatccttgtc aatggtatat atatatatat atatatatat atatgtatat atatatatat | | 3169 |

```
atgtgatcca attctggggg ggcgcagcat caactaaaaa atgtaaggat ttttgaaaca      3229
tctttatttt cccatacgtt ttgacgtaga attctacgtc atcgtcagtg gttttgggat      3289
tctggattat cacttgcaca tcttaacagc aacttgtgaa taattgacgt ttggtgcttg      3349
tttccaattg ttaattattt gcaagttgtt gttgatatgt gtgagtgata atctaagaat      3409
ttcaaaacca ctgacgatga cgtggaattt tacattgaaa tgtatggaag gatgaagatg      3469
ttttggaaat cgttacttta tttgtatttt ttacttgatg ttgtgccctc taagaaatta      3529
atcatacatt tcaacatcaa atttaaaaca ctttcaacat atatctatat gtacatatat      3589
gtatatatat atatatatat atatatatat atatatatat ataatttta aaatttatta      3649 ataaatggca ctaaagtgta gtactgccta ggatgataaa attaaatttt ttgagacaat      3709
ataaatataa ctgaaaaatt acagttttag atttatttga tagttttata ataatgatgc      3769
aataagtgtt aatagcaagc atacatagaa gagcattgca gcacatatttt tcaaatgatt      3829 gattttttat agttatcaat atcatgtcca taaagttatt taatacctaa cactgtgtta      3889 aagtttttt ttcgtttatg ttaatgctca gaatatttga aaatgaaact ggttgtgaaa       3949
cacttctaat aattagtttt tcaatttaat ttttctgttt attagttgaa attgaggaac      4009
ccatgatatt gaaaatagta tcaatgacta acaaatttta atatctttaa catgatttga      4069
aataaatata tatgtataat gtacatagtt gtgtgagcaa agtaagttca cacacattta      4129
aaaaaaaaaa aaaaaaaa                                                   4148

<210> SEQ ID NO 14
<211> LENGTH: 561
<212> TYPE: PRT
<213> ORGANISM: Ctenocephalides felis

<400> SEQUENCE: 14

Met Phe Arg Ala Val Thr Asn Leu Ala Asn Ser Ser Asp Gly Thr Val
1               5                   10                  15

Leu Asn Glu Val Ile His Glu Asp Leu Leu Lys Cys Glu Pro Ser
            20                  25                  30

Thr Ser Val Asp Ala Leu Ser Asn Gly Ala Phe Gly Ser Lys Gln Gln
        35                  40                  45

His Lys Val Glu Glu Trp Lys Arg Ser Pro Ser Pro Ser Leu Thr Asn
    50                  55                  60

Ser His Val Pro Pro Leu Thr Pro Ser Pro Gly Pro Ser Ser Leu Pro
65                  70                  75                  80

Tyr Ser Thr Leu Ser Asn Gly Tyr Ser Ser Pro Met Ser Ser Gly Ser
                85                  90                  95

Cys Asp Pro Tyr Ser Pro Asn Gly Lys Met Gly Arg Glu Asp Leu Ser
            100                 105                 110

Pro Pro Ser Ser Leu Asn Gly Tyr Ser Ala Asp Gly Cys Glu Ala Lys
        115                 120                 125

Lys Ala Lys Lys Gly Pro Ala Pro Arg Gln Gln Glu Glu Leu Cys Leu
    130                 135                 140

Val Cys Gly Asp Arg Ala Ser Gly Tyr His Tyr Asn Ala Leu Thr Cys
145                 150                 155                 160

Glu Gly Cys Lys Gly Phe Phe Arg Arg Ser Val Thr Lys Asn Ala Val
                165                 170                 175

Tyr Val Cys Lys Phe Gly His Thr Cys Glu Met Asp Met Tyr Met Arg
            180                 185                 190

Arg Lys Cys Gln Glu Cys Arg Leu Lys Lys Cys Leu Ala Val Gly Met
```

-continued

```
              195                 200                 205
Arg Pro Glu Cys Val Val Pro Glu Asn Gln Cys Ala Met Lys Arg Lys
    210                 215                 220
Glu Lys Lys Ala Gln Lys Glu Lys Asp Ile Gly Pro Ile Ser Gly Thr
225                 230                 235                 240
Val Gly Lys Ser Ala Ala Pro Leu Ala Asn Ser Ala Leu Leu Gln Lys
                245                 250                 255
Pro Asp Ile Leu Pro Ala Val Met Lys Cys Asp Pro Leu Pro Pro Glu
                260                 265                 270
Ala Thr Lys Val Lys Phe Leu Ser Asp Lys Ile Leu Ala Glu Asn Arg
        275                 280                 285
Ile Arg Asn Val Pro Pro Leu Thr Ala Asn Gln Glu Tyr Val Ile Ala
    290                 295                 300
Arg Leu Val Trp Tyr Gln Asp Gly Tyr Glu Gln Pro Ser Glu Glu Asp
305                 310                 315                 320
Leu Arg Arg Ile Met Ile Ser Thr Pro Ala Glu Asp Ala Leu Glu
                325                 330                 335
Phe Arg His Ile Thr Glu Ile Thr Ile Leu Thr Val Gln Leu Ile Val
                340                 345                 350
Glu Phe Ala Lys Gly Leu Pro Ala Phe Thr Lys Ile Pro Gln Glu Asp
        355                 360                 365
Gln Ile Thr Leu Leu Lys Ala Cys Ser Ser Glu Val Met Met Leu Arg
    370                 375                 380
Met Ala Arg Arg Tyr Asp Ala Val Ser Asp Ser Ile Leu Phe Ala Asn
385                 390                 395                 400
Asn Arg Ser Tyr Thr Arg Asp Ser Tyr Lys Met Ala Gly Met Ala Asp
                405                 410                 415
Thr Ile Glu Asp Leu Leu His Phe Cys Arg Gln Met Tyr Thr Met Thr
                420                 425                 430
Val Asp Asn Val Glu Tyr Ala Leu Ile Thr Ala Ile Val Ile Phe Ser
        435                 440                 445
Asp Arg Pro Gly Leu Glu Gln Ala Asp Leu Val Glu Gln Ile Gln Ser
    450                 455                 460
Tyr Tyr Ile Lys Thr Leu Lys Cys Tyr Ile Leu Asn Arg His Ser Gly
465                 470                 475                 480
Asp Pro Lys Cys Gly Ile Leu Phe Ala Lys Leu Leu Ser Ile Leu Thr
                485                 490                 495
Glu Leu Arg Thr Leu Gly Asn Gln Asn Ser Glu Met Cys Phe Ala Leu
                500                 505                 510
Lys Leu Lys Asn Arg Lys Leu Pro Arg Phe Leu Glu Glu Ile Trp Asp
        515                 520                 525
Val Thr Asp Asn Val Pro Pro Thr Ile Asp Ser Met His Ser Val Ser
    530                 535                 540
Glu Asn Phe Tyr Asn Asn Glu Ser Asn Gly Thr Ser Asp Ser Thr Pro
545                 550                 555                 560
Met
```

<210> SEQ ID NO 15
<211> LENGTH: 4148
<212> TYPE: DNA
<213> ORGANISM: Ctenocephalides felis

<400> SEQUENCE: 15
tttttttttt tttttttttt aaatgtgtgt gaacttactt tgctcacaca actatgtaca    60

-continued

```
ttatacatat atatttattt caaatcatgt taaagatatt aaaatttgtt agtcattgat      120
actattttca atatcatggg ttcctcaatt tcaactaata aacagaaaaa ttaaattgaa      180
aaactaatta ttagaagtgt ttcacaacca gtttcatttt caaatattct gagcattaac      240
ataaacgaaa aaaaaacttt aacacagtgt taggtattaa ataactttat ggacatgata      300
ttgataacta taaaaaatca atcatttgaa aatatgtgct gcaatgctct tctatgtatg      360
cttgctatta acacttattg catcattatt ataaaactat caaataaatc taaaactgta      420
atttttcagt tatatttata ttgtctcaaa aaatttaatt ttatcatcct aggcagtact      480
acactttagt gccatttatt aataaatttt aaattatata tatatatata tatatatata      540
tatatatata tatatataca tatatgtaca tatagatata tgttgaaagt gttttaaatt      600
tgatgttgaa atgtatgatt aatttcttag agggcacaac atcaagtaaa aaatacaaat      660
aaagtaacga tttccaaaac atcttcatcc ttccatacat ttcaatgtaa aattccacgt      720
catcgtcagt ggttttgaaa ttcttagatt atcactcaca catatcaaca acaacttgca      780
aataattaac aattggaaac aagcaccaaa cgtcaattat tcacaagttg ctgttaagat      840
gtgcaagtga taatccagaa tcccaaaacc actgacgatg acgtagaatt ctacgtcaaa      900
acgtatggga aaataaagat gttttcaaaaa tccttacatt ttttagttga tgctgcgccc      960
ccccagaatt ggatcacata tatatatata tatacatata tatatatata tatatatata    1020
tataccattg acaaggatat tttgaacact taattatggt gcaacgttca aaattattat    1080
agcacacgca tacttatatt gatatgccat acatgaacta caaagtagat aattgattaa    1140
aataataaaa atcattaact tttgagagag aatttggcaa atattattaa agtagttgga    1200
acaccaaaca atggcatact ttgtatcatt ttccttacaa atatttaatg aactagcatt    1260
caaatatgat ctaacgttag atgaatcatc acatgtgaat tgagaaaccc tttatttaaa    1320
atcatttgat aagagggcca gtctgaaaat aactttaaaa cattctatcg tcaaacttat    1380
aaaaatacat atattctaac taataaagag ggtgataata tattacacat aatgtcttaa    1440
acagcataaa tttatatgaa gcattaatta cataaacaaa catatacaag ttacagcagc    1500
agcatttgac aagagcactg tatggtttcg gaatgaattt atataatttt gaataaaact    1560
tgcaaatttc taaggtaaaa aatgaatgag gctaaaaata cttgaatcta ttttggaaat    1620
atgttaattt atatcattat agctacttga gcactatgtg tagtatttat atatgtattc    1680
tcgtgtgagg gttgcagcaa ttatagcttc ctttgtcaga tgatttcaaa tggaggtcaa    1740
tataatgtat aggtattttg aggatataga attaaattat ttttcacagc ctatttatct    1800
aatccaaata caattctccc acaacacaaa attcaaattc taacgataaa ataatcaatg    1860
tttatatata attcattgtt gcattgagaa ggttttacct tgcaaagcaa aaatatattt    1920
atacaataag aagtttctgc ttaatatagg taaatcagta tggccggcct acaaatgatt    1980
ttattacaca tgatttcttt ttaatttcct atcgaggtgt aaccttattt taataaggcc    2040
attgagtgta cacagcatat atcaccatcc ttcacattat ctttaacttg gctcttaata    2100
tgtaacagag attttttccaa gtttaccatt ggtatcgtct caatagatta tatattcaaa    2160
aatattgcct taacggcctt tttcccatggt gcttatgtaa tattttaatg ataccttaat    2220
tttccatacc agtacacagt aaacaaatat gcaaagagc tgttgatttt ctgagcactt    2280
tacatcggtg tagaatcact ggtaccatta cttttcattat tatagaaatt ctccgataca    2340
ctatgcatgc tgtctatcgt aggaggcaca ttatctgtca catcccaaat ttcttctaaa    2400
```

-continued

```
aatctaggaa gttttctgtt cttcaatttc agtgcaaaac acatttctga gttttgattt    2460
cctaacgtgc gtaattcagt aagaatagaa agaagtttgg caaacaatat tccacactta    2520
gggtcaccac tatgtcgatt caaaatgtag cactttaatg ttttgatgta ataactttga    2580
atttgttcca caagatctgc ttgttccaat ccaggtcgat ctgaaaaaat cacaattgct    2640
gttattagtg catactccac attgtctaca gtcatagtat acatctgtcg acaaaaatgc    2700
aatagatctt ctattgtatc tgccatacca gccattttat aggagtcacg agtatatgaa    2760
cgattattcg cgaataagat tgaatccgac actgcatcgt accgccgagc cattcgcagc    2820
atcattactt cacttgaaca tgcctttaat aatgttattt gatcttcttg tggtattttg    2880
gtaaaagctg gtaaacccct tgcaaattcc actataagct gcacagtaag tatggtaatt    2940
tcagttatat gccgaaattc aagagcttca tcttcagctg gtgtacttat cattatcctt    3000
cgtaggtctt cctcagaagg ttgttcatat ccatcttggt accacactaa tcttgcgatc    3060
acatattctt gatttgcagt caaggtgga acatttcgaa ttctgttttc agcaagaatc     3120
ttgtctgaca aaaatttcac tttagttgct tctggaggta atgggtcgca tttcatgacc    3180
gcaggcaaaa tatcaggctt ctgaagtaat gcagaattcg ctaggggagc agcagatttt    3240
ccaacggtac ctgatattgg tccgatgtcc ttttccttct gtgccttctt ttcctttcgc    3300
ttcatggcgc attggttttc gggaaccacg cactcggggc gcattccgac agccaaacat    3360
ttcttgagcc tacattcctg acatttgcgt cgcatataca tgtccatttc gcacgtgtgc    3420
ccaaacttgc acacgtacac ggcattctta gtcacacttc gtcggaaaaa acctttgcat    3480
ccttcacaag taagagcgtt gtaatgatat ccggaggcac ggtcgccgca cacaagacat    3540
agttcctcct gctgccgcgg cgccggccct ttcttggcct tcttcgcttc gcagccatct    3600
gctgaatagc cgttcaaaga actaggcggt gacaggtctt ctcgtcccat tttaccatta    3660
gggctatagg gatcgcagct gcctgacgac attggcgaag aatagccatt agacaatgtc    3720
gaatatggta agctggatgg gcctggtgat ggtgtgagag gtggcacatg gctgttcgtc    3780
aaactgggac taggtgatcg cttccattct tcgactttgt gctgctgctt gctaccgaaa    3840
gctccattag ataatgcgtc cacgctagta gagggttcac atttaagcag aagatcttca    3900
tgtataactt cgttcaaaac agttccatca gaagaatttg caagatttgt aaccgctcga    3960
aacattacga atgaaaccgt attatattca atgaactatt tttttactta tttttgtca    4020
atacatgtgg agtttaaaat ttaaatatac cgtaatgcaa atctcgtgcc gaattcctgc    4080
agcccggggg atccactagt tctagagcgg ccgccaccgc ggtggagctc cagcttttgt    4140
tcccttta                                                            4148
```

<210> SEQ ID NO 16
<211> LENGTH: 1683
<212> TYPE: DNA
<213> ORGANISM: Ctenocephalides felis
<220> FEATURE:
<221> NAME/KEY: CDS
<222> LOCATION: (1)..(1683)
<223> OTHER INFORMATION:

<400> SEQUENCE: 16

```
atg ttt cga gcg gtt aca aat ctt gca aat tct tct gat gga act gtt     48
Met Phe Arg Ala Val Thr Asn Leu Ala Asn Ser Ser Asp Gly Thr Val
1               5                   10                  15 ttg aac gaa gtt ata cat gaa gat ctt ctg ctt aaa tgt gaa ccc tct     96
Leu Asn Glu Val Ile His Glu Asp Leu Leu Leu Lys Cys Glu Pro Ser
            20                  25                  30
```

```
act agc gtg gac gca tta tct aat gga gct ttc ggt agc aag cag cag      144
Thr Ser Val Asp Ala Leu Ser Asn Gly Ala Phe Gly Ser Lys Gln Gln
         35                  40                  45 cac aaa gtc gaa gaa tgg aag cga tca cct agt ccc agt ttg acg aac      192
His Lys Val Glu Glu Trp Lys Arg Ser Pro Ser Pro Ser Leu Thr Asn
 50                  55                  60 agc cat gtg cca cct ctc aca cca tca cca ggc cca tcc agc tta cca      240
Ser His Val Pro Pro Leu Thr Pro Ser Pro Gly Pro Ser Ser Leu Pro
 65                  70                  75                  80 tat tcg aca ttg tct aat ggc tat tct tcg cca atg tcg tca ggc agc      288
Tyr Ser Thr Leu Ser Asn Gly Tyr Ser Ser Pro Met Ser Ser Gly Ser
             85                  90                  95 tgc gat ccc tat agc cct aat ggt aaa atg gga cga gaa gac ctg tca      336
Cys Asp Pro Tyr Ser Pro Asn Gly Lys Met Gly Arg Glu Asp Leu Ser
            100                 105                 110 ccg cct agt tct ttg aac ggc tat tca gca gat ggc tgc gaa gcg aag      384
Pro Pro Ser Ser Leu Asn Gly Tyr Ser Ala Asp Gly Cys Glu Ala Lys
            115                 120                 125 aag gcc aag aaa ggg ccg gcg ccg cgg cag cag gag gaa cta tgt ctt      432
Lys Ala Lys Lys Gly Pro Ala Pro Arg Gln Gln Glu Glu Leu Cys Leu
130                 135                 140 gtg tgc ggc gac cgt gcc tcc gga tat cat tac aac gct ctt act tgt      480
Val Cys Gly Asp Arg Ala Ser Gly Tyr His Tyr Asn Ala Leu Thr Cys
145                 150                 155                 160 gaa gga tgc aaa ggt ttt ttc cga cga agt gtg act aag aat gcc gtg      528
Glu Gly Cys Lys Gly Phe Phe Arg Arg Ser Val Thr Lys Asn Ala Val
                165                 170                 175 tac gtg tgc aag ttt ggg cac acg tgc gaa atg gac atg tat atg cga      576
Tyr Val Cys Lys Phe Gly His Thr Cys Glu Met Asp Met Tyr Met Arg
            180                 185                 190 cgc aaa tgt cag gaa tgt agg ctc aag aaa tgt ttg gct gtc gga atg      624
Arg Lys Cys Gln Glu Cys Arg Leu Lys Lys Cys Leu Ala Val Gly Met
            195                 200                 205 cgc ccc gag tgc gtg gtt ccc gaa aac caa tgc gcc atg aag cga aag      672
Arg Pro Glu Cys Val Val Pro Glu Asn Gln Cys Ala Met Lys Arg Lys
210                 215                 220 gaa aag aag gca cag aag gaa aag gac atc gga cca ata tca ggt acc      720
Glu Lys Lys Ala Gln Lys Glu Lys Asp Ile Gly Pro Ile Ser Gly Thr
225                 230                 235                 240 gtt gga aaa tct gct gct ccc cta gcg aat tct gca tta ctt cag aag      768
Val Gly Lys Ser Ala Ala Pro Leu Ala Asn Ser Ala Leu Leu Gln Lys
                245                 250                 255 cct gat att ttg cct gcg gtc atg aaa tgc gac cca tta cct cca gaa      816
Pro Asp Ile Leu Pro Ala Val Met Lys Cys Asp Pro Leu Pro Pro Glu
            260                 265                 270 gca act aaa gtg aaa ttt ttg tca gac aag att ctt gct gaa aac aga      864
Ala Thr Lys Val Lys Phe Leu Ser Asp Lys Ile Leu Ala Glu Asn Arg
            275                 280                 285 att cga aat gtt cca cct ttg act gca aat caa gaa tat gtg atc gca      912
Ile Arg Asn Val Pro Pro Leu Thr Ala Asn Gln Glu Tyr Val Ile Ala
            290                 295                 300 aga tta gtg tgg tac caa gat gga tat gaa caa cct tct gag gaa gac      960
Arg Leu Val Trp Tyr Gln Asp Gly Tyr Glu Gln Pro Ser Glu Glu Asp
305                 310                 315                 320 cta cga agg ata atg ata agt aca cca gct gaa gat gaa gct ctt gaa     1008
Leu Arg Arg Ile Met Ile Ser Thr Pro Ala Glu Asp Glu Ala Leu Glu
                325                 330                 335 ttt cgg cat ata act gaa att acc ata ctt act gtg cag ctt ata gtg     1056
Phe Arg His Ile Thr Glu Ile Thr Ile Leu Thr Val Gln Leu Ile Val
```

-continued

```
                340                 345                 350
gaa ttt gca aag ggt tta cca gct ttt acc aaa ata cca caa gaa gat      1104
Glu Phe Ala Lys Gly Leu Pro Ala Phe Thr Lys Ile Pro Gln Glu Asp
            355                 360                 365 caa ata aca tta tta aag gca tgt tca agt gaa gta atg atg ctg cga      1152
Gln Ile Thr Leu Leu Lys Ala Cys Ser Ser Glu Val Met Met Leu Arg
        370                 375                 380 atg gct cgg cgg tac gat gca gtg tcg gat tca atc tta ttc gcg aat      1200
Met Ala Arg Arg Tyr Asp Ala Val Ser Asp Ser Ile Leu Phe Ala Asn
385                 390                 395                 400 aat cgt tca tat act cgt gac tcc tat aaa atg gct ggt atg gca gat      1248
Asn Arg Ser Tyr Thr Arg Asp Ser Tyr Lys Met Ala Gly Met Ala Asp
                405                 410                 415 aca ata gaa gat cta ttg cat ttt tgt cga cag atg tat act atg act      1296
Thr Ile Glu Asp Leu Leu His Phe Cys Arg Gln Met Tyr Thr Met Thr
            420                 425                 430 gta gac aat gtg gag tat gca cta ata aca gca att gtg att ttt tca      1344
Val Asp Asn Val Glu Tyr Ala Leu Ile Thr Ala Ile Val Ile Phe Ser
        435                 440                 445 gat cga cct gga ttg gaa caa gca gat ctt gtg gaa caa att caa agt      1392
Asp Arg Pro Gly Leu Glu Gln Ala Asp Leu Val Glu Gln Ile Gln Ser
450                 455                 460 tat tac atc aaa aca tta aag tgc tac att ttg aat cga cat agt ggt      1440
Tyr Tyr Ile Lys Thr Leu Lys Cys Tyr Ile Leu Asn Arg His Ser Gly
465                 470                 475                 480 gac cct aag tgt gga ata ttg ttt gcc aaa ctt ctt tct att ctt act      1488
Asp Pro Lys Cys Gly Ile Leu Phe Ala Lys Leu Leu Ser Ile Leu Thr
                485                 490                 495 gaa tta cgc acg tta gga aat caa aac tca gaa atg tgt ttt gca ctg      1536
Glu Leu Arg Thr Leu Gly Asn Gln Asn Ser Glu Met Cys Phe Ala Leu
            500                 505                 510 aaa ttg aag aac aga aaa ctt cct aga ttt tta gaa gaa att tgg gat      1584
Lys Leu Lys Asn Arg Lys Leu Pro Arg Phe Leu Glu Glu Ile Trp Asp
        515                 520                 525 gtg aca gat aat gtg cct cct acg ata gac agc atg cat agt gta tcg      1632
Val Thr Asp Asn Val Pro Pro Thr Ile Asp Ser Met His Ser Val Ser
530                 535                 540 gag aat ttc tat aat aat gaa agt aat ggt acc agt gat tct aca ccg      1680
Glu Asn Phe Tyr Asn Asn Glu Ser Asn Gly Thr Ser Asp Ser Thr Pro
545                 550                 555                 560 atg                                                                  1683
Met
```

<210> SEQ ID NO 17
<211> LENGTH: 561
<212> TYPE: PRT
<213> ORGANISM: Ctenocephalides felis

<400> SEQUENCE: 17

```
Met Phe Arg Ala Val Thr Asn Leu Ala Asn Ser Ser Asp Gly Thr Val
1               5                   10                  15

Leu Asn Glu Val Ile His Glu Asp Leu Leu Lys Cys Glu Pro Ser
            20                  25                  30

Thr Ser Val Asp Ala Leu Ser Asn Gly Ala Phe Gly Ser Lys Gln Gln
        35                  40                  45

His Lys Val Glu Glu Trp Lys Arg Ser Pro Ser Pro Ser Leu Thr Asn
    50                  55                  60

Ser His Val Pro Pro Leu Thr Pro Ser Pro Gly Pro Ser Ser Leu Pro
65                  70                  75                  80
```

-continued

```
Tyr Ser Thr Leu Ser Asn Gly Tyr Ser Pro Met Ser Ser Gly Ser
             85                  90                  95
Cys Asp Pro Tyr Ser Pro Asn Gly Lys Met Gly Arg Glu Asp Leu Ser
            100                 105                 110
Pro Pro Ser Ser Leu Asn Gly Tyr Ser Ala Asp Gly Cys Glu Ala Lys
            115                 120                 125
Lys Ala Lys Lys Gly Pro Ala Pro Arg Gln Gln Glu Glu Leu Cys Leu
130                 135                 140
Val Cys Gly Asp Arg Ala Ser Gly Tyr His Tyr Asn Ala Leu Thr Cys
145                 150                 155                 160
Glu Gly Cys Lys Gly Phe Phe Arg Arg Ser Val Thr Lys Asn Ala Val
            165                 170                 175
Tyr Val Cys Lys Phe Gly His Thr Cys Glu Met Asp Met Tyr Met Arg
            180                 185                 190
Arg Lys Cys Gln Glu Cys Arg Leu Lys Lys Cys Leu Ala Val Gly Met
            195                 200                 205
Arg Pro Glu Cys Val Val Pro Glu Asn Gln Cys Ala Met Lys Arg Lys
210                 215                 220
Glu Lys Lys Ala Gln Lys Glu Lys Asp Ile Gly Pro Ile Ser Gly Thr
225                 230                 235                 240
Val Gly Lys Ser Ala Ala Pro Leu Ala Asn Ser Ala Leu Leu Gln Lys
            245                 250                 255
Pro Asp Ile Leu Pro Ala Val Met Lys Cys Asp Pro Leu Pro Pro Glu
            260                 265                 270
Ala Thr Lys Val Lys Phe Leu Ser Asp Lys Ile Leu Ala Glu Asn Arg
            275                 280                 285
Ile Arg Asn Val Pro Pro Leu Thr Ala Asn Gln Glu Tyr Val Ile Ala
            290                 295                 300
Arg Leu Val Trp Tyr Gln Asp Gly Tyr Glu Gln Pro Ser Glu Glu Asp
305                 310                 315                 320
Leu Arg Arg Ile Met Ile Ser Thr Pro Ala Glu Asp Glu Ala Leu Glu
            325                 330                 335
Phe Arg His Ile Thr Glu Ile Thr Ile Leu Thr Val Gln Leu Ile Val
            340                 345                 350
Glu Phe Ala Lys Gly Leu Pro Ala Phe Thr Lys Ile Pro Gln Glu Asp
            355                 360                 365
Gln Ile Thr Leu Leu Lys Ala Cys Ser Ser Glu Val Met Met Leu Arg
            370                 375                 380
Met Ala Arg Arg Tyr Asp Ala Val Ser Asp Ser Ile Leu Phe Ala Asn
385                 390                 395                 400
Asn Arg Ser Tyr Thr Arg Asp Ser Tyr Lys Met Ala Gly Met Ala Asp
                405                 410                 415
Thr Ile Glu Asp Leu Leu His Phe Cys Arg Gln Met Tyr Thr Met Thr
            420                 425                 430
Val Asp Asn Val Glu Tyr Ala Leu Ile Thr Ala Ile Val Ile Phe Ser
            435                 440                 445
Asp Arg Pro Gly Leu Glu Gln Ala Asp Leu Val Glu Gln Ile Gln Ser
            450                 455                 460
Tyr Tyr Ile Lys Thr Leu Lys Cys Tyr Ile Leu Asn Arg His Ser Gly
465                 470                 475                 480
Asp Pro Lys Cys Gly Ile Leu Phe Ala Lys Leu Leu Ser Ile Leu Thr
            485                 490                 495
```

```
Glu Leu Arg Thr Leu Gly Asn Gln Asn Ser Glu Met Cys Phe Ala Leu
            500                 505                 510
Lys Leu Lys Asn Arg Lys Leu Pro Arg Phe Leu Glu Glu Ile Trp Asp
        515                 520                 525
Val Thr Asp Asn Val Pro Pro Thr Ile Asp Ser Met His Ser Val Ser
    530                 535                 540
Glu Asn Phe Tyr Asn Asn Glu Ser Asn Gly Thr Ser Asp Ser Thr Pro
545                 550                 555                 560
Met

<210> SEQ ID NO 18
<211> LENGTH: 1683
<212> TYPE: DNA
<213> ORGANISM: Ctenocephalides felis

<400> SEQUENCE: 18
```

| | | | | | |
|---|---|---|---|---|---|
| catcggtgta | gaatcactgg | taccattact | ttcattatta | tagaaattct | ccgatacact | 60 |
| atgcatgctg | tctatcgtag | gaggcacatt | atctgtcaca | tcccaaattt | cttctaaaaa | 120 |
| tctaggaagt | tttctgttct | tcaatttcag | tgcaaaacac | atttctgagt | tttgatttcc | 180 |
| taacgtgcgt | aattcagtaa | gaatagaaag | aagtttggca | acaatattc | cacacttagg | 240 |
| gtcaccacta | tgtcgattca | aaatgtagca | ctttaatgtt | ttgatgtaat | aactttgaat | 300 |
| ttgttccaca | agatctgctt | gttccaatcc | aggtcgatct | gaaaaaatca | caattgctgt | 360 |
| tattagtgca | tactccacat | tgtctacagt | catagtatac | atctgtcgac | aaaaatgcaa | 420 |
| tagatcttct | attgtatctg | ccataccagc | cattttatag | gagtcacgag | tatatgaacg | 480 |
| attattcgcg | aataagattg | aatccgacac | tgcatcgtac | cgccgagcca | ttcgcagcat | 540 |
| cattacttca | cttgaacatg | cctttaataa | tgttatttga | tcttcttgtg | gtattttggt | 600 |
| aaaagctggt | aaacccttg | caaattccac | tataagctgc | acagtaagta | tggtaatttc | 660 |
| agttatatgc | cgaaattcaa | gagcttcatc | ttcagctggt | gtacttatca | ttatccttcg | 720 |
| taggtcttcc | tcagaaggtt | gttcatatcc | atcttggtac | cacactaatc | ttgcgatcac | 780 |
| atattcttga | tttgcagtca | aaggtggaac | atttcgaatt | ctgttttcag | caagaatctt | 840 |
| gtctgacaaa | aatttcactt | tagttgcttc | tggaggtaat | gggtcgcatt | tcatgaccgc | 900 |
| aggcaaaata | tcaggcttct | gaagtaatgc | agaattcgct | aggggagcag | cagatttcc | 960 |
| aacggtacct | gatattggtc | cgatgtcctt | ttccttctgt | gccttctttt | cctttcgctt | 1020 |
| catggcgcat | tggttttcgg | gaaccacgca | ctcgggcgc | attccgacag | ccaaacattt | 1080 |
| cttgagccta | cattcctgac | atttgcgtcg | catatacatg | tccatttcgc | acgtgtgccc | 1140 |
| aaacttgcac | acgtacacgg | cattcttagt | cacacttcgt | cggaaaaaac | ctttgcatcc | 1200 |
| ttcacaagta | agagcgttgt | aatgatatcc | ggaggcacgg | tcgccgcaca | caagacatag | 1260 |
| ttcctcctgc | tgccgcggcg | ccggcccttt | cttggccttc | ttcgcttcgc | agccatctgc | 1320 |
| tgaatagccg | ttcaaagaac | taggcggtga | caggtcttct | cgtcccattt | taccattagg | 1380 |
| gctatatggga | tcgcagctgc | ctgacgacat | tggcgaagaa | tagccattag | acaatgtcga | 1440 |
| atatggtaag | ctggatgggc | ctggtgatgg | tgtgagaggt | ggcacatggc | tgttcgtcaa | 1500 |
| actgggacta | ggtgatcgct | tccattcttc | gactttgtgc | tgctgcttgc | taccgaaagc | 1560 |
| tccattagat | aatgcgtcca | cgctagtaga | gggttcacat | ttaagcagaa | gatcttcatg | 1620 |
| tataacttcg | ttcaaaacag | ttccatcaga | agaatttgca | agatttgtaa | ccgctcgaaa | 1680 |
| cat | | | | | | 1683 |

<210> SEQ ID NO 19
<211> LENGTH: 160
<212> TYPE: DNA
<213> ORGANISM: Ctenocephalides felis

<400> SEQUENCE: 19

| | | | |
|---|---|---|---|
| cagttgcgaa ggttgtaagg gattttcaa acggacggta cgaaaagatc tgacgtatgc | 60 |
| ctgtcgagag gatagaaatt gtttgatcga caaaaggcag agaaatcgat gtcagttctg | 120 |
| tcgatatcag aaatgtctcg cctgtggaat gaaacgagaa | 160 |

<210> SEQ ID NO 20
<211> LENGTH: 160
<212> TYPE: DNA
<213> ORGANISM: Ctenocephalides felis

<400> SEQUENCE: 20

| | |
|---|---|
| ttctcgtttc attccacagg cgagacattt ctgatatcga cagaactgac atcgatttct | 60 |
| ctgccttttg tcgatcaaac aatttctatc ctctcgacag gcatacgtca gatcttttcg | 120 |
| taccgtccgt ttgaaaaatc ccttacaacc ttcgcaactg | 160 |

<210> SEQ ID NO 21
<211> LENGTH: 2149
<212> TYPE: DNA
<213> ORGANISM: Ctenocephalides felis

<400> SEQUENCE: 21

| | |
|---|---|
| ccgcggcgat agcatcgaaa cgcgtcgcat ggaacgcatt tgtaattgtt ttctgcataa | 60 |
| aatgcctaaa gtcgcggaca gtcaagtgat tgaagtgatg gtatgcgcgc gactcggttt | 120 |
| gttttgacgt gttcgaagat gaacgatatt ttaaatattt tgtgtttagt tttagtctcg | 180 |
| agataatttt tgtgctgtgt gataagagtt gtgctttcat aaaaaggaat tgtttattag | 240 |
| attttgaatg acagtgcccc atgtgggaga tgacatactg aacgcattag tttatatgtt | 300 |
| gcttataatt gagtatagga ataaactgtt aatttcaatt ttttggtaac tccaaatgtt | 360 |
| acctcaaaaa cttaaagtaa gggtcaaata taaaaaaaag tgtcattaag aaattcaaca | 420 |
| tgactagtac acatatcagt gagtgagttt atattagaaa tgaaggagac gcataaattg | 480 |
| gtaacttaat taagcattac aatcaactgg gaataaataa atatatcttc taaaatgatg | 540 |
| aaaaaagaga agcctatgat gtctgtgacg gctttgattc aaggagccgc tcagaatcaa | 600 |
| atatggggac gaggattatc tggccttaca ggcttggccc tcgaccaagg gctgtcaatg | 660 |
| agctcgatgg gaccgctctc accgccggat atgaaaccgg atcctgcgct actgaacggc | 720 |
| ggcttttcgc ccggcagtgg cggcgcagtt gtcggcagtc ccgctagtcc gccttttggt | 780 |
| caaaatcaca caatagtatc aggaaacacg gccacgggcg cccaaacgaa atcaccatac | 840 |
| cctccaaatc atcctttgag cgggtcaaaa catctgtgct ccatatgcgg agatagggct | 900 |
| tccgggaagc attatggtgt ttacagttgc gaaggttgta agggattttt caaacgacg | 960 |
| gtacgaaaag atctgacgta tgcctgtcga gaggatagaa attgtttgat cgacaaaagg | 1020 |
| cagagaaatc gatgtcagtt ctgtcgatat cagaaatgtc tcgcctgtgg aatgaaacga | 1080 |
| gaagccgtgc aggaagaacg acaacgagga gcaaagaata tgaagaaag caacccgaca | 1140 |
| agttctgttc gtgatttaac ggtagaaaga atttagaag cagaacaaag gagtgaaact | 1200 |
| cgaaatgttg cgacggaccc ggaattgtcg atacaatatt tgcgagtagg accttcatcc | 1260 |

-continued

| | | | | |
|---|---|---|---|---|
| atggtgcctc | ctagatacaa | gggccctgta | tccagtctgt | gtcagcaagc | aaataaacag | 1320 |
| ttatatcagt | tagtacaata | cgcaaggtgc | atgccgcatt | ttagtgcttt | acaattagag | 1380 |
| gatcaagtaa | cgttactcag | agcagcctgg | aatgaattac | ttatagcatc | tatagcctgg | 1440 |
| agaagtattg | agtatctaga | atccgatgca | gaaacaagta | cgtccagtat | gtctagtgat | 1500 |
| acttcaacaa | ggagacgcgc | tccaccagga | ccgcctgaat | taatgtgttt | ctttcctggt | 1560 |
| atgacgttac | atcggaatag | tgcaatccag | gctggcgtcg | gacctatttt | cgatcgggta | 1620 |
| ctgtcagaat | taagtgtcaa | aatgagaaga | atggatttgg | acagagcaga | attaggctgt | 1680 |
| ttgaaggcta | taatactgtt | taatcctggt | aaatgatgta | aaaatataac | aaaagtttct | 1740 |
| gaaatttatt | gtaatgcttg | atttaaaaaa | aatgctaact | tgaatgttag | cgcagtcttg | 1800 |
| tctacggtag | tatgacttaa | tttaatatat | gtaatttaga | aacttgaaga | acacttgaaa | 1860 |
| ttttgacgat | ggcttggggc | acctaggact | aagtgaaatg | ttgcaaatat | tgttttacaa | 1920 |
| ttgttttcaa | attgttattg | ttttttaaatt | ttgctttcat | aatgttgatg | tattgaatta | 1980 |
| gtctgtgaat | cacgttaaaa | gcttccaact | cttttatata | ttgaataagt | aatctattca | 2040 |
| aagcaattat | atatcaaata | tattaatgca | tttttattat | ttaacatttg | tgttcataat | 2100 |
| tatttaatat | agttattaat | ttagattaaa | aaaaaaaaaa | aaaaaaaa | | 2149 |

<210> SEQ ID NO 22
<211> LENGTH: 2149
<212> TYPE: DNA
<213> ORGANISM: Ctenocephalides felis

<400> SEQUENCE: 22

| | | | | | | |
|---|---|---|---|---|---|---|
| tttttttttt | tttttttttt | ttaatctaaa | ttaataacta | tattaaataa | ttatgaacac | 60 |
| aaatgttaaa | taataaaaat | gcattaatat | atttgatata | taattgcttt | gaatagatta | 120 |
| cttattcaat | atataaaaga | gttggaagct | tttaacgtga | ttcacagact | aattcaatac | 180 |
| atcaacatta | tgaaagcaaa | atttaaaaac | aataacaatt | tgaaacaat | tgtaaaacaa | 240 |
| tatttgcaac | atttcactta | gtcctaggtg | ccccaagcca | tcgtcaaaat | ttcaagtgtt | 300 |
| cttcaagttt | ctaaattaca | tatattaaat | taagtcatac | taccgtagac | aagactgcgc | 360 |
| taacattcaa | gttagcattt | ttttttaaatc | aagcattaca | ataaatttca | gaaacttttg | 420 |
| ttatattttt | acatcattta | ccaggattaa | acagtattat | agccttcaaa | cagcctaatt | 480 |
| ctgctctgtc | caaatccatt | cttctcattt | tgacacttaa | ttctgacagt | acccgatcga | 540 |
| aaataggtcc | gacgccagcc | tggattgcac | tattccgatg | taacgtcata | ccaggaaaga | 600 |
| aacacattaa | ttcaggcggt | cctggtggag | cgcgtctcct | tgttgaagta | tcactagaca | 660 |
| tactggacgt | acttgtttct | gcatcggatt | ctagatactc | aatacttctc | caggctatag | 720 |
| atgctataag | taattcattc | caggctgctc | tgagtaacgt | tacttgatcc | tctaattgta | 780 |
| aagcactaaa | atgcggcatg | caccttgcgt | attgtactaa | ctgatataac | tgtttatttg | 840 |
| cttgctgaca | cagactggat | acagggccct | tgtatctagg | aggcaccatg | gatgaaggtc | 900 |
| ctactcgcaa | atattgtatc | gacaattccg | ggtccgtcgc | aacatttcga | gtttcactcc | 960 |
| tttgttctgc | ttctaaaatt | cttttctaccg | ttaaatcacg | aacagaactt | gtcgggttgc | 1020 |
| tttcttcatt | attctttgct | cctcgttgtc | gttcttcctg | cacggcttct | cgtttcattc | 1080 |
| cacaggcgag | acattctga | tatcgacaga | actgacatcg | atttctctgc | cttttgtcga | 1140 |
| tcaaacaatt | tctatcctct | cgacaggcat | acgtcagatc | ttttcgtacc | gtccgtttga | 1200 |
| aaaatcccctt | acaaccttcg | caactgtaaa | caccataatg | cttcccggaa | gccctatctc | 1260 |

-continued

```
cgcatatgga gcacagatgt tttgacccgc tcaaaggatg atttggaggg tatggtgatt      1320
tcgtttgggc gcccgtggcc gtgtttcctg atactattgt gtgattttga ccaaaaggcg      1380
gactagcggg actgccgaca actgcgccgc cactgccggg cgaaaagccg ccgttcagta      1440
gcgcaggatc cggtttcata tccggcggtg agagcggtcc catcgagctc attgacagcc      1500
cttggtcgag ggccaagcct gtaaggccag ataatcctcg tccccatatt tgattctgag      1560
cggctccttg aatcaaagcc gtcacagaca tcataggctt ctcttttttc atcattttag      1620
aagatatatt tatttattcc cagttgattg taatgcttaa ttaagttacc aatttatgcg      1680
tctccttcat ttctaatata aactcactca ctgatatgtg tactagtcat gttgaatttc      1740
ttaatgacac ttttttttat atttgaccct tactttaagt ttttgaggta acatttggag      1800
ttaccaaaaa attgaaatta acagtttatt cctatactca attataagca acatataaac      1860
taatgcgttc agtatgtcat ctcccacatg gggcactgtc attcaaaatc taataaacaa      1920
ttccttttta tgaaagcaca actcttatca cacagcacaa aaattatctc gagactaaaa      1980
ctaaacacaa aatatttaaa atatcgttca tcttcgaaca cgtcaaaaca aaccgagtcg      2040
cgcgcatacc atcacttcaa tcacttgact gtccgcgact ttaggcattt tatgcagaaa      2100
acaattacaa atgcgttcca tgcgacgcgt ttcgatgcta tcgccgcgg                 2149
```

<210> SEQ ID NO 23
<211> LENGTH: 1421
<212> TYPE: DNA
<213> ORGANISM: Ctenocephalides felis

<400> SEQUENCE: 23

```
gcggcacgag ggagataggg cttccgggaa gcattatggt gtttacagtt gcgaaggttg        60
taagggattt ttcaaacgga cggtacgaaa agatctgacg tatgcctgtc gaggagatag       120
aaattgtttg atcgacaaaa ggcagagaaa tcgatgtcag ttctgtcgat atcagaaatg       180
tctcgcctgt ggaatgaaac gagaagccgt gcaggaagaa cgacaacgag gagcaaagaa       240
taatgaagaa agcaacccga caagttctgt tcgtgattta acggtagaaa gaattttaga       300
agcagaacaa aggagtgaaa ctcgaaatgt tgcgacggac ccggaattgt cgatacaata       360
tttgcgagta ggaccttcat ccatggtgcc tcctagatac aagggccctg tatccagtct       420
gtgtcagcaa gcaaataaac agttatatca gttagtacaa tacgcaaggt gcatgccgca       480
ttttagtgct ttacaattag aggatcaagt aacgttactc agagcagcct ggaatgaatt       540
acttatagca tctatagcct ggagaagtat tgagtatcta gaatccgatg cagaaacaag       600
tacgtccagt atgtctagtg atacttcaac aaggagacgc gctccaccag gaccgcctga       660
attaatgtgt ttctttcctg gtatgacgtt acatcggaat agtgcaatcc aggctggcgt       720
cggacctatt ttcgatcggg tactgtcaga attaagtgtc aaaatgagaa gaatggattt       780
ggacagagca gaattaggct gttttgaaggc tataatactg tttaatcctg atattcgagg       840
actgaaatgt agacaggaag tggatgcttt acgagaaaag gtttacgcgt gcctggacga       900
gcattgcagg acgcagcatc cagcggaaga gggtcgtttc gcagccctgc tgcttcgcct       960
gccagctctg aggtcaatct ctttgaaatg tctcgatcac ctgttttctt tcagattgat      1020
tggcgatacg ccgcttgaga gttttcttgt ggatttactc gaggccggac ccatcggttg      1080
agccgattca tggataaaag ataagtttta tgtattaaga tgagaataag taaatattct      1140
gcaaagttat tttttctgca cgaatatttc tacaagcacg cacttgggat attgattgtc      1200
```

| tcttgtgatc ttttgaggtg gcggggagga tacgaaccag tgatatttta aaatattttt | 1260 |
|---|---|
| aattattaga gattaggata gcggtataag tactgtaatg catatataca tatatgcttt | 1320 |
| tgatttatat tagaagtttt tctgcatcat ccagtgaatt aaaataagat ataataagga | 1380 |
| aaagtccata tataaaaaaa aaaaaaaaaa aaaaaaaaaa a | 1421 |

<210> SEQ ID NO 24
<211> LENGTH: 1421
<212> TYPE: DNA
<213> ORGANISM: Ctenocephalides felis

<400> SEQUENCE: 24

| ttttttttt ttttttttt ttttttttat atatggactt ttccttatta tatcttattt | 60 |
|---|---|
| taattcactg gatgatgcag aaaaacttct aatataaatc aaaagcatat atgtatatat | 120 |
| gcattacagt acttataccg ctatcctaat ctctaataat taaaaatatt ttaaaatatc | 180 |
| actggttcgt atcctccccg ccacctcaaa agatcacaag agacaatcaa tatcccaagt | 240 |
| gcgtgcttgt agaaatattc gtgcagaaaa aataactttg cagaatattt acttattctc | 300 |
| atcttaatac ataaaactta tcttttatcc atgaatcggc tcaaccgatg ggtccggcct | 360 |
| cgagtaaatc cacaagaaaa ctctcaagcg gcgtatcgcc aatcaatctg aagaaaaaca | 420 |
| ggtgatcgag acatttcaaa gagattgacc tcagagctgg caggcgaagc agcagggctg | 480 |
| cgaaacgacc ctcttccgct ggatgctgcg tcctgcaatg ctcgtccagg cacgcgtaaa | 540 |
| ccttttctcg taaagcatcc acttcctgtc tacatttcag tcctcgaata tcaggattaa | 600 |
| acagtattat agccttcaaa cagcctaatt ctgctctgtc caaatccatt cttctcattt | 660 |
| tgacacttaa ttctgacagt acccgatcga aaataggtcc gacgccagcc tggattgcac | 720 |
| tattccgatg taacgtcata ccaggaaaga aacacattaa ttcaggcggt cctggtggag | 780 |
| cgcgtctcct tgttgaagta tcactagaca tactggacgt acttgttcct gcatcggatt | 840 |
| ctagatactc aatacttctc caggctatag atgctataag taattcattc caggctgctc | 900 |
| tgagtaacgt tacttgatcc tctaattgta aagcactaaa atgcggcatg caccttgcgt | 960 |
| attgtactaa ctgatataac tgtttatttg cttgctgaca cagactggat acagggccct | 1020 |
| tgtatctagg aggcaccatg gatgaaggtc ctactcgcaa atattgtatc gacaattccg | 1080 |
| ggtccgtcgc aacatttcga gtttcactcc tttgttctgc ttctaaaatt ctttctaccg | 1140 |
| ttaaatcacg aacagaactt gtcgggttgc tttcttcatt attctttgct cctcgttgtc | 1200 |
| gttcttcctg cacggcttct cgtttcattc cacaggcgag acatttctga tatcgacaga | 1260 |
| actgacatcg atttctctgc cttttgtcga tcaaacaatt tctatctcct cgacaggcat | 1320 |
| acgtcagatc ttttcgtacc gtccgtttga aaaatccctt acaaccttcg caactgtaaa | 1380 |
| caccataatg cttcccggaa gccctatctc cctcgtgccg c | 1421 |

<210> SEQ ID NO 25
<211> LENGTH: 819
<212> TYPE: DNA
<213> ORGANISM: Ctenocephalides felis

<400> SEQUENCE: 25

| aacaaaagct ggagctccac cgcggtggcg gccgctctag aactagtgga tcccccgggc | 60 |
|---|---|
| tgcaggaatt cggcacgaga ttttatgtag gttacaataa attttaaatt aaaattatgt | 120 |
| tgcacaatta cttttaacaa gttttttatt ttatcgttaa gtagtgcgtt atgttaattc | 180 |
| aaaataaatc gtttaatgaa cgaaattcat gagtttgttg aaggaaatag ttgatagttc | 240 |

-continued

```
atcgaccttagagtgacagtacgcggccatgtttatacaaatattaaataatgttgctt      300 tattaaagttcagttcaaaaagctaaaataagtgaaaaagtgatactgctagtttagtg      360 gaacaataatggaaagtgcagacagaggctggccttcgaccaagggctgtcaatgagct      420 cgatgggaccgctctcaccgccggatatgaaccggatcctgtgctactgaacggcggct      480 tttcgcccggcagtggcggcgcagttgtcgcagtcccgctagtccgccttcgggtcaaa    540 atcacacaatagtatcaggaaacacggccacgggcgcccaaacgaaatcaccataccctc      600 caaatcatcctttgagcgggtcaaaacatctgtgctccatatgcgagatagggcttccg      660 ggaagcattatggtgtttacagttgcgaaggttgtaagggattttttcaaacggacggtac   720 gaaaagatctgacgtatgcctgtcgagaagatagaaattgtttgatcgacaaaaggcaga     780 gaaatcgatgtcagttctgtcgatatcagaatgtctcg                          819
```

<210> SEQ ID NO 26
<211> LENGTH: 1749
<212> TYPE: DNA
<213> ORGANISM: Ctenocephalides felis
<220> FEATURE:
<221> NAME/KEY: CDS
<222> LOCATION: (306)..(1652)
<223> OTHER INFORMATION:

<400> SEQUENCE: 26

```
tagtggacccccgggctgcaggaattcggcacgagatttaaattaaaattatgttgca       60 caattactttaacaagttttttatttatcgttaagtagtgcgttatgttaattcaaaa      120 taaatcgtttaatgaacgaaattcatgagtttgttgaaggaaatagttgatagttcatcg    180 accttacagagtgacagtacgcggccatgtttatacaaattaaataatgttgctttat     240 taaagttcagttcaaaaaagctaaataagtgaaaagtgatactgctagtttagtggaa     300 caata atg gaa agt gca gac aga ggc ttg gcc ctc gac caa ggg ctg tca        350
      Met Glu Ser Ala Asp Arg Gly Leu Ala Leu Asp Gln Gly Leu Ser
        1               5                  10                  15 atg agc tcg atg gga ccg ctc tca ccg ccg gat atg aaa ccg gat cct         398
Met Ser Ser Met Gly Pro Leu Ser Pro Pro Asp Met Lys Pro Asp Pro
             20                  25                  30 gcg cta ctg aac ggc ggc ttt tcg ccc ggc agt ggc ggc gca gtt gtc         446
Ala Leu Leu Asn Gly Gly Phe Ser Pro Gly Ser Gly Gly Ala Val Val
         35                  40                  45 ggc agt ccc gct agt ccg cct ttt ggt caa aat cac aca ata gta tca         494
Gly Ser Pro Ala Ser Pro Pro Phe Gly Gln Asn His Thr Ile Val Ser
     50                  55                  60 gga aac acg gcc acg ggc gcc caa acg aaa tca cca tac cct cca aat         542
Gly Asn Thr Ala Thr Gly Ala Gln Thr Lys Ser Pro Tyr Pro Pro Asn
 65                  70                  75 cat cct ttg agc ggg tca aaa cat ctg tgc tcc ata tgc gga gat agg         590
His Pro Leu Ser Gly Ser Lys His Leu Cys Ser Ile Cys Gly Asp Arg
 80                  85                  90                  95 gct tcc ggg aag cat tat ggt gtt tac agt tgc gaa ggt tgt aag gga         638
Ala Ser Gly Lys His Tyr Gly Val Tyr Ser Cys Glu Gly Cys Lys Gly
                100                 105                 110 ttt ttc aaa cgg acg gta cga aaa gat ctg acg tat gcc tgt cga gag         686
Phe Phe Lys Arg Thr Val Arg Lys Asp Leu Thr Tyr Ala Cys Arg Glu
            115                 120                 125 gat aga aat tgt ttg atc gac aaa agg cag aga aat cga tgt cag ttc         734
Asp Arg Asn Cys Leu Ile Asp Lys Arg Gln Arg Asn Arg Cys Gln Phe
        130                 135                 140
```

-continued

| | | |
|---|---|---|
| tgt cga tat cag aaa tgt ctc gcc tgt gga atg aaa cga gaa gcc gtg<br>Cys Arg Tyr Gln Lys Cys Leu Ala Cys Gly Met Lys Arg Glu Ala Val<br>145 150 155 | | 782 |
| cag gaa gaa cga caa cga gga gca aag aat aat gaa gaa agc aac ccg<br>Gln Glu Glu Arg Gln Arg Gly Ala Lys Asn Asn Glu Glu Ser Asn Pro<br>160 165 170 175 | | 830 |
| aca agt tct gtt cgt gat tta acg gta gaa aga att tta gaa gca gaa<br>Thr Ser Ser Val Arg Asp Leu Thr Val Glu Arg Ile Leu Glu Ala Glu<br>180 185 190 | | 878 |
| caa agg agt gaa act cga aat gtt gcg acg gac ccg gaa ttg tcg ata<br>Gln Arg Ser Glu Thr Arg Asn Val Ala Thr Asp Pro Glu Leu Ser Ile<br>195 200 205 | | 926 |
| caa tat ttg cga gta gga cct tca tcc atg gtg cct cct aga tac aag<br>Gln Tyr Leu Arg Val Gly Pro Ser Ser Met Val Pro Pro Arg Tyr Lys<br>210 215 220 | | 974 |
| ggc cct gta tcc agt ctg tgt cag caa gca aat aaa cag tta tat cag<br>Gly Pro Val Ser Ser Leu Cys Gln Gln Ala Asn Lys Gln Leu Tyr Gln<br>225 230 235 | | 1022 |
| tta gta caa tac gca agg tgc atg ccg cat ttt agt gct tta caa tta<br>Leu Val Gln Tyr Ala Arg Cys Met Pro His Phe Ser Ala Leu Gln Leu<br>240 245 250 255 | | 1070 |
| gag gat caa gta acg tta ctc aga gca gcc tgg aat gaa tta ctt ata<br>Glu Asp Gln Val Thr Leu Leu Arg Ala Ala Trp Asn Glu Leu Leu Ile<br>260 265 270 | | 1118 |
| gca tct ata gcc tgg aga agt att gag tat cta gaa tcc gat gca gaa<br>Ala Ser Ile Ala Trp Arg Ser Ile Glu Tyr Leu Glu Ser Asp Ala Glu<br>275 280 285 | | 1166 |
| aca agt acg tcc agt atg tct agt gat act tca aca agg aga cgc gct<br>Thr Ser Thr Ser Ser Met Ser Ser Asp Thr Ser Thr Arg Arg Arg Ala<br>290 295 300 | | 1214 |
| cca cca gga ccg cct gaa tta atg tgt ttc ttt cct ggt atg acg tta<br>Pro Pro Gly Pro Pro Glu Leu Met Cys Phe Phe Pro Gly Met Thr Leu<br>305 310 315 | | 1262 |
| cat cgg aat agt gca atc cag gct ggc gtc gga cct att ttc gat cgg<br>His Arg Asn Ser Ala Ile Gln Ala Gly Val Gly Pro Ile Phe Asp Arg<br>320 325 330 335 | | 1310 |
| gta ctg tca gaa tta agt gtc aaa atg aga aga atg gat ttg gac aga<br>Val Leu Ser Glu Leu Ser Val Lys Met Arg Arg Met Asp Leu Asp Arg<br>340 345 350 | | 1358 |
| gca gaa tta ggc tgt ttg aag gct ata ata ctg ttt aat cct gat att<br>Ala Glu Leu Gly Cys Leu Lys Ala Ile Ile Leu Phe Asn Pro Asp Ile<br>355 360 365 | | 1406 |
| cga gga ctg aaa tgt aga cag gaa gtg gat gct tta cga gaa aag gtt<br>Arg Gly Leu Lys Cys Arg Gln Glu Val Asp Ala Leu Arg Glu Lys Val<br>370 375 380 | | 1454 |
| tac gcg tgc ctg gac gag cat tgc agg acg cag cat cca gcg gaa gag<br>Tyr Ala Cys Leu Asp Glu His Cys Arg Thr Gln His Pro Ala Glu Glu<br>385 390 395 | | 1502 |
| ggt cgt ttc gca gcc ctg ctg ctt cgc ctg cca gct ctg agg tca atc<br>Gly Arg Phe Ala Ala Leu Leu Leu Arg Leu Pro Ala Leu Arg Ser Ile<br>400 405 410 415 | | 1550 |
| tct ttg aaa tgt ctc gat cac ctg ttt ttc ttc aga ttg att ggc gat<br>Ser Leu Lys Cys Leu Asp His Leu Phe Phe Phe Arg Leu Ile Gly Asp<br>420 425 430 | | 1598 |
| acg ccg ctt gag agt ttt ctt gtg gat tta ctc gag gcc gga ccg atc<br>Thr Pro Leu Glu Ser Phe Leu Val Asp Leu Leu Glu Ala Gly Pro Ile<br>435 440 445 | | 1646 |
| ggt tga gccgattcat ggataaaaga taagtttttat gtattaagat gagaataagt<br>Gly | | 1702 | aaatattctg caaagttatt ttttctgcac gaatatttct acaagca        1749

<210> SEQ ID NO 27
<211> LENGTH: 448
<212> TYPE: PRT
<213> ORGANISM: Ctenocephalides felis

<400> SEQUENCE: 27

| Met | Glu | Ser | Ala | Asp | Arg | Gly | Leu | Ala | Leu | Asp | Gln | Gly | Leu | Ser | Met |
|---|---|---|---|---|---|---|---|---|---|---|---|---|---|---|---|
| 1 | | | | 5 | | | | | 10 | | | | | 15 | |

Ser Ser Met Gly Pro Leu Ser Pro Pro Asp Met Lys Pro Asp Pro Ala
              20                  25                  30

Leu Leu Asn Gly Gly Phe Ser Pro Gly Ser Gly Ala Val Val Gly
          35                  40                  45

Ser Pro Ala Ser Pro Pro Phe Gly Gln Asn His Thr Ile Val Ser Gly
        50                  55                  60

Asn Thr Ala Thr Gly Ala Gln Thr Lys Ser Pro Tyr Pro Pro Asn His
65                  70                  75                  80

Pro Leu Ser Gly Ser Lys His Leu Cys Ser Ile Cys Gly Asp Arg Ala
                85                  90                  95

Ser Gly Lys His Tyr Gly Val Tyr Ser Cys Glu Gly Cys Lys Gly Phe
            100                 105                 110

Phe Lys Arg Thr Val Arg Lys Asp Leu Thr Tyr Ala Cys Arg Glu Asp
        115                 120                 125

Arg Asn Cys Leu Ile Asp Lys Arg Gln Arg Asn Arg Cys Gln Phe Cys
    130                 135                 140

Arg Tyr Gln Lys Cys Leu Ala Cys Gly Met Lys Arg Glu Ala Val Gln
145                 150                 155                 160

Glu Glu Arg Gln Arg Gly Ala Lys Asn Asn Glu Ser Asn Pro Thr
                165                 170                 175

Ser Ser Val Arg Asp Leu Thr Val Glu Arg Ile Leu Glu Ala Glu Gln
            180                 185                 190

Arg Ser Glu Thr Arg Asn Val Ala Thr Asp Pro Glu Leu Ser Ile Gln
        195                 200                 205

Tyr Leu Arg Val Gly Pro Ser Ser Met Val Pro Pro Arg Tyr Lys Gly
210                 215                 220

Pro Val Ser Ser Leu Cys Gln Gln Ala Asn Lys Gln Leu Tyr Gln Leu
225                 230                 235                 240

Val Gln Tyr Ala Arg Cys Met Pro His Phe Ser Ala Leu Gln Leu Glu
                245                 250                 255

Asp Gln Val Thr Leu Leu Arg Ala Ala Trp Asn Glu Leu Leu Ile Ala
            260                 265                 270

Ser Ile Ala Trp Arg Ser Ile Glu Tyr Leu Glu Ser Asp Ala Glu Thr
        275                 280                 285

Ser Thr Ser Ser Met Ser Ser Asp Thr Ser Thr Arg Arg Arg Ala Pro
    290                 295                 300

Pro Gly Pro Pro Glu Leu Met Cys Phe Phe Pro Gly Met Thr Leu His
305                 310                 315                 320

Arg Asn Ser Ala Ile Gln Ala Gly Val Gly Pro Ile Phe Asp Arg Val
                325                 330                 335

Leu Ser Glu Leu Ser Val Lys Met Arg Arg Met Asp Leu Asp Arg Ala
            340                 345                 350

Glu Leu Gly Cys Leu Lys Ala Ile Ile Leu Phe Asn Pro Asp Ile Arg
        355                 360                 365

```
Gly Leu Lys Cys Arg Gln Glu Val Asp Ala Leu Arg Glu Lys Val Tyr
    370                 375                 380

Ala Cys Leu Asp Glu His Cys Arg Thr Gln His Pro Ala Glu Glu Gly
385                 390                 395                 400

Arg Phe Ala Ala Leu Leu Arg Leu Pro Ala Leu Arg Ser Ile Ser
                405                 410                 415

Leu Lys Cys Leu Asp His Leu Phe Phe Phe Arg Leu Ile Gly Asp Thr
            420                 425                 430

Pro Leu Glu Ser Phe Leu Val Asp Leu Leu Glu Ala Gly Pro Ile Gly
        435                 440                 445

<210> SEQ ID NO 28
<211> LENGTH: 1749
<212> TYPE: DNA
<213> ORGANISM: Ctenocephalides felis

<400> SEQUENCE: 28
tgcttgtaga aatattcgtg cagaaaaaat aactttgcag aatatttact tattctcatc      60
ttaatacata aaacttatct tttatccatg aatcggctca accgatcggt ccggcctcga     120
gtaaatccac aagaaaactc tcaagcggcg tatcgccaat caatctgaag aaaaacaggt     180
gatcgagaca tttcaaagag attgacctca gagctggcag gcgaagcagc agggctgcga     240
aacgaccctc ttccgctgga tgctgcgtcc tgcaatgctc gtccaggcac gcgtaaacct     300
tttctcgtaa agcatccact tcctgtctac atttcagtcc tcgaatatca ggattaaaca     360
gtattatagc cttcaaacag cctaattctg ctctgtccaa atccattctt ctcattttga     420
cacttaattc tgacagtacc cgatcgaaaa taggtccgac gccagcctgg attgcactat     480
tccgatgtaa cgtcatacca ggaaagaaac acattaattc aggcggtcct ggtggagcgc     540
gtctccttgt tgaagtatca ctagacatat ggacgtact tgtttctgca tcggattcta     600
gatactcaat acttctccag gctatagatg ctataagtaa ttcattccag gctgctctga     660
gtaacgttac ttgatcctct aattgtaaag cactaaaatg cggcatgcac cttgcgtatt     720
gtactaactg atataactgt ttatttgctt gctgacacag actggataca gggcccttgt     780
atctaggagg caccatggat gaaggtccta ctcgcaaata ttgtatcgac aattccgggt     840
ccgtcgcaac atttcgagtt tcactccttt gttctgcttc taaaattctt tctaccgtta     900
aatcacgaac agaacttgtc gggttgcttt cttcattatt ctttgctcct cgttgtcgtt     960
cttcctgcac ggcttctcgt ttcattccac aggcgagaca tttctgatat cgacagaact    1020
gacatcgatt tctctgcctt tgtcgatca aacaatttct atcctctcga caggcatacg    1080
tcagatcttt tcgtaccgtc cgtttgaaaa atcccttaca accttcgcaa ctgtaaacac    1140
cataatgctt cccggaagcc ctatctccgc atatggagca cagatgtttt gacccgctca    1200
aaggatgatt tggagggtat ggtgatttcg tttgggcgcc cgtggccgtg tttcctgata    1260
ctattgtgtg attttgacca aaaggcggac tagcgggact gccgacaact gcgccgccac    1320
tgccgggcga aaagccgccg ttcagtagcg caggatccgg tttcatatcc ggcggtgaga    1380
gcggtcccat cgagctcatt gacagccctt ggtcgagggc caagcctctg tctgcacttt    1440
ccattattgt tccactaaac tagcagtatc acttttcac ttattttagc tttttgaac    1500 tgaactttaa taaagcaaca ttatttaata tttgtataaa catggccgcg tactgtcact    1560
ctgtaaggtc gatgaactat caactatttc cttcaacaaa ctcatgaatt tcgttcatta    1620
aacgatttat tttgaattaa cataacgcac tacttaacga taaaataaaa aacttgttaa    1680
```

```
aagtaattgt gcaacataat tttaatttaa aatctcgtgc cgaattcctg cagcccgggg    1740
ggtccacta                                                            1749

<210> SEQ ID NO 29
<211> LENGTH: 1344
<212> TYPE: DNA
<213> ORGANISM: Ctenocephalides felis
<220> FEATURE:
<221> NAME/KEY: CDS
<222> LOCATION: (1)..(1344)
<223> OTHER INFORMATION:

<400> SEQUENCE: 29 atg gaa agt gca gac aga ggc ttg gcc ctc gac caa ggg ctg tca atg     48
Met Glu Ser Ala Asp Arg Gly Leu Ala Leu Asp Gln Gly Leu Ser Met
1               5                   10                  15 agc tcg atg gga ccg ctc tca ccg ccg gat atg aaa ccg gat cct gcg     96
Ser Ser Met Gly Pro Leu Ser Pro Pro Asp Met Lys Pro Asp Pro Ala
            20                  25                  30 cta ctg aac ggc ggc ttt tcg ccc ggc agt ggc ggc gca gtt gtc ggc    144
Leu Leu Asn Gly Gly Phe Ser Pro Gly Ser Gly Gly Ala Val Val Gly
        35                  40                  45 agt ccc gct agt ccg cct ttt ggt caa aat cac aca ata gta tca gga    192
Ser Pro Ala Ser Pro Pro Phe Gly Gln Asn His Thr Ile Val Ser Gly
    50                  55                  60 aac acg gcc acg ggc gcc caa acg aaa tca cca tac cct cca aat cat    240
Asn Thr Ala Thr Gly Ala Gln Thr Lys Ser Pro Tyr Pro Pro Asn His
65                  70                  75                  80 cct ttg agc ggg tca aaa cat ctg tgc tcc ata tgc gga gat agg gct    288
Pro Leu Ser Gly Ser Lys His Leu Cys Ser Ile Cys Gly Asp Arg Ala
                85                  90                  95 tcc ggg aag cat tat ggt gtt tac agt tgc gaa ggt tgt aag gga ttt    336
Ser Gly Lys His Tyr Gly Val Tyr Ser Cys Glu Gly Cys Lys Gly Phe
            100                 105                 110 ttc aaa cgg acg gta cga aaa gat ctg acg tat gcc tgt cga gag gat    384
Phe Lys Arg Thr Val Arg Lys Asp Leu Thr Tyr Ala Cys Arg Glu Asp
        115                 120                 125 aga aat tgt ttg atc gac aaa agg cag aga aat cga tgt cag ttc tgt    432
Arg Asn Cys Leu Ile Asp Lys Arg Gln Arg Asn Arg Cys Gln Phe Cys
    130                 135                 140 cga tat cag aaa tgt ctc gcc tgt gga atg aaa cga gaa gcc gtg cag    480
Arg Tyr Gln Lys Cys Leu Ala Cys Gly Met Lys Arg Glu Ala Val Gln
145                 150                 155                 160 gaa gaa cga caa cga gga gca aag aat aat gaa gaa agc aac ccg aca    528
Glu Glu Arg Gln Arg Gly Ala Lys Asn Asn Glu Glu Ser Asn Pro Thr
                165                 170                 175 agt tct gtt cgt gat tta acg gta gaa aga att tta gaa gca gaa caa    576
Ser Ser Val Arg Asp Leu Thr Val Glu Arg Ile Leu Glu Ala Glu Gln
            180                 185                 190 agg agt gaa act cga aat gtt gcg acg gac ccg gaa ttg tcg ata caa    624
Arg Ser Glu Thr Arg Asn Val Ala Thr Asp Pro Glu Leu Ser Ile Gln
        195                 200                 205 tat ttg cga gta gga cct tca tcc atg gtg cct cct aga tac aag ggc    672
Tyr Leu Arg Val Gly Pro Ser Ser Met Val Pro Pro Arg Tyr Lys Gly
    210                 215                 220 cct gta tcc agt ctg tgt cag caa gca aat aaa cag tta tat cag tta    720
Pro Val Ser Ser Leu Cys Gln Gln Ala Asn Lys Gln Leu Tyr Gln Leu
225                 230                 235                 240 gta caa tac gca agg tgc atg ccg cat ttt agt gct tta caa tta gag    768
Val Gln Tyr Ala Arg Cys Met Pro His Phe Ser Ala Leu Gln Leu Glu
                245                 250                 255
```

```
gat caa gta acg tta ctc aga gca gcc tgg aat gaa tta ctt ata gca      816
Asp Gln Val Thr Leu Leu Arg Ala Ala Trp Asn Glu Leu Leu Ile Ala
        260                 265                 270 tct ata gcc tgg aga agt att gag tat cta gaa tcc gat gca gaa aca      864
Ser Ile Ala Trp Arg Ser Ile Glu Tyr Leu Glu Ser Asp Ala Glu Thr
        275                 280                 285 agt acg tcc agt atg tct agt gat act tca aca agg aga cgc gct cca      912
Ser Thr Ser Ser Met Ser Ser Asp Thr Ser Thr Arg Arg Arg Ala Pro
        290                 295                 300 cca gga ccg cct gaa tta atg tgt ttc ttt cct ggt atg acg tta cat      960
Pro Gly Pro Pro Glu Leu Met Cys Phe Phe Pro Gly Met Thr Leu His
305                 310                 315                 320 cgg aat agt gca atc cag gct ggc gtc gga cct att ttc gat cgg gta     1008
Arg Asn Ser Ala Ile Gln Ala Gly Val Gly Pro Ile Phe Asp Arg Val
                325                 330                 335 ctg tca gaa tta agt gtc aaa atg aga aga atg gat ttg gac aga gca     1056
Leu Ser Glu Leu Ser Val Lys Met Arg Arg Met Asp Leu Asp Arg Ala
                340                 345                 350 gaa tta ggc tgt ttg aag gct ata ata ctg ttt aat cct gat att cga     1104
Glu Leu Gly Cys Leu Lys Ala Ile Ile Leu Phe Asn Pro Asp Ile Arg
        355                 360                 365 gga ctg aaa tgt aga cag gaa gtg gat gct tta cga gaa aag gtt tac     1152
Gly Leu Lys Cys Arg Gln Glu Val Asp Ala Leu Arg Glu Lys Val Tyr
370                 375                 380 gcg tgc ctg gac gag cat tgc agg acg cag cat cca gcg gaa gag ggt     1200
Ala Cys Leu Asp Glu His Cys Arg Thr Gln His Pro Ala Glu Glu Gly
385                 390                 395                 400 cgt ttc gca gcc ctg ctg ctt cgc ctg cca gct ctg agg tca atc tct     1248
Arg Phe Ala Ala Leu Leu Leu Arg Leu Pro Ala Leu Arg Ser Ile Ser
                405                 410                 415 ttg aaa tgt ctc gat cac ctg ttt ttc ttc aga ttg att ggc gat acg     1296
Leu Lys Cys Leu Asp His Leu Phe Phe Phe Arg Leu Ile Gly Asp Thr
                420                 425                 430 ccg ctt gag agt ttt ctt gtg gat tta ctc gag gcc gga ccg atc ggt     1344
Pro Leu Glu Ser Phe Leu Val Asp Leu Leu Glu Ala Gly Pro Ile Gly
        435                 440                 445
```

<210> SEQ ID NO 30
<211> LENGTH: 448
<212> TYPE: PRT
<213> ORGANISM: Ctenocephalides felis

<400> SEQUENCE: 30

```
Met Glu Ser Ala Asp Arg Gly Leu Ala Leu Asp Gln Gly Leu Ser Met
1               5                   10                  15

Ser Ser Met Gly Pro Leu Ser Pro Pro Asp Met Lys Pro Asp Pro Ala
            20                  25                  30

Leu Leu Asn Gly Gly Phe Ser Pro Gly Ser Gly Gly Ala Val Val Gly
        35                  40                  45

Ser Pro Ala Ser Pro Pro Phe Gly Gln Asn His Thr Ile Val Ser Gly
    50                  55                  60

Asn Thr Ala Thr Gly Ala Gln Thr Lys Ser Pro Tyr Pro Asn His
65                  70                  75                  80

Pro Leu Ser Gly Ser Lys His Leu Cys Ser Ile Cys Gly Asp Arg Ala
                85                  90                  95

Ser Gly Lys His Tyr Gly Val Tyr Ser Cys Glu Gly Cys Lys Gly Phe
            100                 105                 110

Phe Lys Arg Thr Val Arg Lys Asp Leu Thr Tyr Ala Cys Arg Glu Asp
```

```
            115                 120                 125
Arg Asn Cys Leu Ile Asp Lys Arg Gln Arg Asn Arg Cys Gln Phe Cys
    130                 135                 140

Arg Tyr Gln Lys Cys Leu Ala Cys Gly Met Lys Arg Glu Ala Val Gln
145                 150                 155                 160

Glu Glu Arg Gln Arg Gly Ala Lys Asn Asn Glu Glu Ser Asn Pro Thr
                165                 170                 175

Ser Ser Val Arg Asp Leu Thr Val Glu Arg Ile Leu Glu Ala Glu Gln
            180                 185                 190

Arg Ser Glu Thr Arg Asn Val Ala Thr Asp Pro Glu Leu Ser Ile Gln
        195                 200                 205

Tyr Leu Arg Val Gly Pro Ser Ser Met Val Pro Pro Arg Tyr Lys Gly
    210                 215                 220

Pro Val Ser Ser Leu Cys Gln Gln Ala Asn Lys Gln Leu Tyr Gln Leu
225                 230                 235                 240

Val Gln Tyr Ala Arg Cys Met Pro His Phe Ser Ala Leu Gln Leu Glu
                245                 250                 255

Asp Gln Val Thr Leu Leu Arg Ala Ala Trp Asn Glu Leu Leu Ile Ala
            260                 265                 270

Ser Ile Ala Trp Arg Ser Ile Glu Tyr Leu Glu Ser Asp Ala Glu Thr
        275                 280                 285

Ser Thr Ser Ser Met Ser Ser Asp Thr Ser Thr Arg Arg Arg Ala Pro
    290                 295                 300

Pro Gly Pro Pro Glu Leu Met Cys Phe Phe Pro Gly Met Thr Leu His
305                 310                 315                 320

Arg Asn Ser Ala Ile Gln Ala Gly Val Gly Pro Ile Phe Asp Arg Val
                325                 330                 335

Leu Ser Glu Leu Ser Val Lys Met Arg Arg Met Asp Leu Asp Arg Ala
            340                 345                 350

Glu Leu Gly Cys Leu Lys Ala Ile Ile Leu Phe Asn Pro Asp Ile Arg
        355                 360                 365

Gly Leu Lys Cys Arg Gln Glu Val Asp Ala Leu Arg Glu Lys Val Tyr
    370                 375                 380

Ala Cys Leu Asp Glu His Cys Arg Thr Gln His Pro Ala Glu Glu Gly
385                 390                 395                 400

Arg Phe Ala Ala Leu Leu Leu Arg Leu Pro Ala Leu Arg Ser Ile Ser
                405                 410                 415

Leu Lys Cys Leu Asp His Leu Phe Phe Phe Arg Leu Ile Gly Asp Thr
            420                 425                 430

Pro Leu Glu Ser Phe Leu Val Asp Leu Leu Glu Ala Gly Pro Ile Gly
        435                 440                 445
```

<210> SEQ ID NO 31
<211> LENGTH: 1344
<212> TYPE: DNA
<213> ORGANISM: Ctenocephalides felis

<400> SEQUENCE: 31

```
accgatcggt ccggcctcga gtaaatccac aagaaaactc tcaagcggcg tatcgccaat      60
caatctgaag aaaaacaggt gatcgagaca tttcaaagag attgacctca gagctggcag     120
gcgaagcagc agggctgcga acgaccctc ttccgctgga tgctgcgtcc tgcaatgctc      180
gtccaggcac gcgtaaacct tttctcgtaa agcatccact tcctgtctac atttcagtcc     240
tcgaatatca ggattaaaca gtattatagc cttcaaacag cctaattctg ctctgtccaa     300
```

-continued

```
atccattctt ctcattttga cacttaattc tgacagtacc cgatcgaaaa taggtccgac        360
gccagcctgg attgcactat tccgatgtaa cgtcatacca ggaaagaaac acattaattc        420
aggcggtcct ggtggagcgc gtctccttgt tgaagtatca ctagacatac tggacgtact        480
tgtttctgca tcggattcta gatactcaat acttctccag gctatagatg ctataagtaa        540
ttcattccag gctgctctga gtaacgttac ttgatcctct aattgtaaag cactaaaatg        600
cggcatgcac cttgcgtatt gtactaactg atataactgt ttatttgctt gctgacacag        660
actggataca gggcccttgt atctaggagg caccatggat gaaggtccta ctcgcaaata        720
ttgtatcgac aattccgggt ccgtcgcaac atttcgagtt tcactccttt gttctgcttc        780
taaaattctt tctaccgtta atcacgaac agaacttgtc gggttgcttt cttcattatt         840
ctttgctcct cgttgtcgtt cttcctgcac ggcttctcgt ttcattccac aggcgagaca        900
tttctgatat cgacagaact gacatcgatt tctctgcctt ttgtcgatca acaatttct         960 atcctctcga caggcatacg tcagatcttt tcgtaccgtc cgtttgaaaa atcccttaca       1020
accttcgcaa ctgtaaacac cataatgctt cccggaagcc ctatctccgc atatggagca       1080
cagatgtttt gacccgctca aggatgatt tggagggtat ggtgatttcg tttgggcgcc        1140
cgtggccgtg tttcctgata ctattgtgtg attttgacca aaaggcggac tagcgggact       1200
gccgacaact gcgccgccac tgccgggcga aaagccgccg ttcagtagcg caggatccgg       1260
tttcatatcc ggcggtgaga gcggtcccat cgagctcatt gacagccctt ggtcgagggc       1320
caagcctctg tctgcacttt ccat                                              1344
```

<210> SEQ ID NO 32
<211> LENGTH: 1975
<212> TYPE: DNA
<213> ORGANISM: Ctenocephalides felis
<220> FEATURE:
<221> NAME/KEY: CDS
<222> LOCATION: (454)..(1878)
<223> OTHER INFORMATION:

<400> SEQUENCE: 32

```
agtcaagtga ttgaagtgat ggtatgcgcg cgactcggtt tgttttgacg tgttcgaaga         60
tgaacgatat tttaaatatt ttgtgtttag ttttagtctc gagataattt ttgtgctgtg        120
tgataagagt tgtgctttca taaaaggaa ttgtttatta gattttgaat gacagtgccc         180
catgtgggag atgacatact gaacgtatta gtttatatgt tgcttataat tgagtatagg        240
aataaactgt taatttcaat tttttggtaa ctccaaatgt tacctcaaaa acttaaagta        300
agggtcaaat ataaaaaaag tgtcattaag aaattcaaca tgactagtac acatatcagt        360
gagtgagttt atattagaaa tgaaggagac gcataaatgg taacttaatt aagcattaca        420
atcaactggg aataaataaa tatatcttct aaa atg atg aaa aaa gag aag cct         474
                                     Met Met Lys Lys Glu Lys Pro
                                       1               5 atg atg tct gtg acg gct ttg att caa gga gcc gct cag aat caa ata         522
Met Met Ser Val Thr Ala Leu Ile Gln Gly Ala Ala Gln Asn Gln Ile
         10                  15                  20 tgg gga cga gga tta tct ggc ctt aca ggc ttg gcc ctc gac caa ggg         570
Trp Gly Arg Gly Leu Ser Gly Leu Thr Gly Leu Ala Leu Asp Gln Gly
     25                  30                  35 ctg tca atg agc tcg atg gga ccg ctc tca ctg ccg gat atg aaa ccg         618
Leu Ser Met Ser Ser Met Gly Pro Leu Ser Leu Pro Asp Met Lys Pro
40                  45                  50                  55
```

-continued

| | | |
|---|---|---|
| gat cct gcg cta ctg aac ggc ggc ttt tcg ccc ggc agt ggc ggc gca<br>Asp Pro Ala Leu Leu Asn Gly Gly Phe Ser Pro Gly Ser Gly Gly Ala<br>            60              65              70 | | 666 |
| gtt gtc ggc agt ccc gct agt ccg cct ttt ggt caa aat cac aca ata<br>Val Val Gly Ser Pro Ala Ser Pro Pro Phe Gly Gln Asn His Thr Ile<br>    75              80              85 | | 714 |
| gta tca gga aac acg gcc acg ggc gcc caa acg aaa tca cca tac cct<br>Val Ser Gly Asn Thr Ala Thr Gly Ala Gln Thr Lys Ser Pro Tyr Pro<br>        90              95              100 | | 762 |
| cca aat cat cct ttg agc ggg tca aaa cat ctg tgc tcc ata tgc gga<br>Pro Asn His Pro Leu Ser Gly Ser Lys His Leu Cys Ser Ile Cys Gly<br>    105             110             115 | | 810 |
| gat agg gct tcc ggg aag cat tat ggt gtt tac agt tgc gaa ggt tgt<br>Asp Arg Ala Ser Gly Lys His Tyr Gly Val Tyr Ser Cys Glu Gly Cys<br>120             125             130             135 | | 858 |
| aag gga ttt ttc aaa cgg acg gta cga aaa gat ctg acg tat gcc tgt<br>Lys Gly Phe Phe Lys Arg Thr Val Arg Lys Asp Leu Thr Tyr Ala Cys<br>                140             145             150 | | 906 |
| cga gag gat aga aat tgt ttg atc gac aaa agg cag aga aat cga tgt<br>Arg Glu Asp Arg Asn Cys Leu Ile Asp Lys Arg Gln Arg Asn Arg Cys<br>            155             160             165 | | 954 |
| cag ttc tgt cga tat cag aaa tgt ctc gcc tgt gga atg aaa cga gaa<br>Gln Phe Cys Arg Tyr Gln Lys Cys Leu Ala Cys Gly Met Lys Arg Glu<br>        170             175             180 | | 1002 |
| gcc gtg cag gaa gaa cga caa cga gga gca aag aat aat gaa gaa agc<br>Ala Val Gln Glu Glu Arg Gln Arg Gly Ala Lys Asn Asn Glu Glu Ser<br>    185             190             195 | | 1050 |
| aac ccg aca agt tct gtt cgt gat tta acg gta gaa aga att tta gaa<br>Asn Pro Thr Ser Ser Val Arg Asp Leu Thr Val Glu Arg Ile Leu Glu<br>200             205             210             215 | | 1098 |
| gca gaa caa agg agt gaa act cga aat gtt gcg acg gac ccg gaa ttg<br>Ala Glu Gln Arg Ser Glu Thr Arg Asn Val Ala Thr Asp Pro Glu Leu<br>                220             225             230 | | 1146 |
| tcg ata caa tat ttg cga gta gga cct tca tcc atg gtg cct cct aga<br>Ser Ile Gln Tyr Leu Arg Val Gly Pro Ser Ser Met Val Pro Pro Arg<br>            235             240             245 | | 1194 |
| tac aag ggc cct gta tcc agt ctg tgt cag caa gca aat aaa cag tta<br>Tyr Lys Gly Pro Val Ser Ser Leu Cys Gln Gln Ala Asn Lys Gln Leu<br>        250             255             260 | | 1242 |
| tat cag tta gta caa tac gca agg tgc atg ccg cat ttt agt gct tta<br>Tyr Gln Leu Val Gln Tyr Ala Arg Cys Met Pro His Phe Ser Ala Leu<br>    265             270             275 | | 1290 |
| caa tta gag gat caa gta acg tta ctc aga gca gcc tgg aat gaa tta<br>Gln Leu Glu Asp Gln Val Thr Leu Leu Arg Ala Ala Trp Asn Glu Leu<br>280             285             290             295 | | 1338 |
| ctt ata gca tct ata gcc tgg aga agt att gag tat cta gaa tcc gat<br>Leu Ile Ala Ser Ile Ala Trp Arg Ser Ile Glu Tyr Leu Glu Ser Asp<br>                300             305             310 | | 1386 |
| gca gaa aca agt acg tcc agt atg tct agt gat act tca aca agg aga<br>Ala Glu Thr Ser Thr Ser Ser Met Ser Ser Asp Thr Ser Thr Arg Arg<br>            315             320             325 | | 1434 |
| cgc gct cca cca gga ccg cct gaa tta atg tgt ttc ttt cct ggt atg<br>Arg Ala Pro Pro Gly Pro Pro Glu Leu Met Cys Phe Phe Pro Gly Met<br>        330             335             340 | | 1482 |
| acg tta cat cgg aat agt gca atc cag gct ggc gtc gga cct att ttc<br>Thr Leu His Arg Asn Ser Ala Ile Gln Ala Gly Val Gly Pro Ile Phe<br>    345             350             355 | | 1530 |
| gat cgg gta ctg tca gaa tta agt gtc aaa atg aga aga atg gat ttg<br>Asp Arg Val Leu Ser Glu Leu Ser Val Lys Met Arg Arg Met Asp Leu<br>360             365             370             375 | | 1578 |

-continued

```
gac aga gca gaa tta ggc tgt ttg aag gct ata ata ctg ttt aat cct    1626
Asp Arg Ala Glu Leu Gly Cys Leu Lys Ala Ile Ile Leu Phe Asn Pro
                380                 385                 390 gat att cga gga ctg aaa tgt aga cag gaa gtg gat gct tta cga gaa    1674
Asp Ile Arg Gly Leu Lys Cys Arg Gln Glu Val Asp Ala Leu Arg Glu
            395                 400                 405 aag gtt tac gcg tgc ctg gac gag cat tgc agg acg cag cat cca gcg    1722
Lys Val Tyr Ala Cys Leu Asp Glu His Cys Arg Thr Gln His Pro Ala
        410                 415                 420 gaa gag ggt cgt ttc gca gcc ctg ctg ctt cgc ctg cca gct ctg agg    1770
Glu Glu Gly Arg Phe Ala Ala Leu Leu Leu Arg Leu Pro Ala Leu Arg
    425                 430                 435 tca atc tct ttg aaa tgt ctc gat cac ctg ttt ttc ttc aga ttg att    1818
Ser Ile Ser Leu Lys Cys Leu Asp His Leu Phe Phe Phe Arg Leu Ile
440                 445                 450                 455 ggc gat acg ccg ctt gag agt ttt ctt gtg gat tta ctc gag gcc gga    1866
Gly Asp Thr Pro Leu Glu Ser Phe Leu Val Asp Leu Leu Glu Ala Gly
                460                 465                 470 ccg atc ggt tga gccgattcat ggataaaaga taagttttat gtattaagat        1918
Pro Ile Gly gagaataagt aaatattctg caaagttatt ttttctgcac gaatatttct acaagca     1975

<210> SEQ ID NO 33
<211> LENGTH: 474
<212> TYPE: PRT
<213> ORGANISM: Ctenocephalides felis

<400> SEQUENCE: 33

Met Met Lys Lys Glu Lys Pro Met Met Ser Val Thr Ala Leu Ile Gln
1               5                   10                  15

Gly Ala Ala Gln Asn Gln Ile Trp Gly Arg Gly Leu Ser Gly Leu Thr
            20                  25                  30

Gly Leu Ala Leu Asp Gln Gly Leu Ser Met Ser Ser Met Gly Pro Leu
        35                  40                  45

Ser Leu Pro Asp Met Lys Pro Asp Pro Ala Leu Leu Asn Gly Gly Phe
    50                  55                  60

Ser Pro Gly Ser Gly Gly Ala Val Val Gly Ser Pro Ala Ser Pro Pro
65                  70                  75                  80

Phe Gly Gln Asn His Thr Ile Val Ser Gly Asn Thr Ala Thr Gly Ala
                85                  90                  95

Gln Thr Lys Ser Pro Tyr Pro Pro Asn His Pro Leu Ser Gly Ser Lys
            100                 105                 110

His Leu Cys Ser Ile Cys Gly Asp Arg Ala Ser Gly Lys His Tyr Gly
        115                 120                 125

Val Tyr Ser Cys Glu Gly Cys Lys Gly Phe Phe Lys Arg Thr Val Arg
    130                 135                 140

Lys Asp Leu Thr Tyr Ala Cys Arg Glu Asp Arg Asn Cys Leu Ile Asp
145                 150                 155                 160

Lys Arg Gln Arg Asn Arg Cys Gln Phe Cys Arg Tyr Gln Lys Cys Leu
                165                 170                 175

Ala Cys Gly Met Lys Arg Glu Ala Val Gln Glu Glu Arg Gln Arg Gly
            180                 185                 190

Ala Lys Asn Asn Glu Glu Ser Asn Pro Thr Ser Ser Val Arg Asp Leu
        195                 200                 205

Thr Val Glu Arg Ile Leu Glu Ala Glu Gln Arg Ser Glu Thr Arg Asn
    210                 215                 220
```

```
Val Ala Thr Asp Pro Glu Leu Ser Ile Gln Tyr Leu Arg Val Gly Pro
225                 230                 235                 240

Ser Ser Met Val Pro Pro Arg Tyr Lys Gly Pro Val Ser Ser Leu Cys
            245                 250                 255

Gln Gln Ala Asn Lys Gln Leu Tyr Gln Leu Val Gln Tyr Ala Arg Cys
            260                 265                 270

Met Pro His Phe Ser Ala Leu Gln Leu Glu Asp Gln Val Thr Leu Leu
            275                 280                 285

Arg Ala Ala Trp Asn Glu Leu Leu Ile Ala Ser Ile Ala Trp Arg Ser
290                 295                 300

Ile Glu Tyr Leu Glu Ser Asp Ala Glu Thr Ser Thr Ser Ser Met Ser
305                 310                 315                 320

Ser Asp Thr Ser Thr Arg Arg Arg Ala Pro Pro Gly Pro Pro Glu Leu
                325                 330                 335

Met Cys Phe Phe Pro Gly Met Thr Leu His Arg Asn Ser Ala Ile Gln
            340                 345                 350

Ala Gly Val Gly Pro Ile Phe Asp Arg Val Leu Ser Glu Leu Ser Val
            355                 360                 365

Lys Met Arg Arg Met Asp Leu Asp Arg Ala Glu Leu Gly Cys Leu Lys
370                 375                 380

Ala Ile Ile Leu Phe Asn Pro Asp Ile Arg Gly Leu Lys Cys Arg Gln
385                 390                 395                 400

Glu Val Asp Ala Leu Arg Glu Lys Val Tyr Ala Cys Leu Asp Glu His
                405                 410                 415

Cys Arg Thr Gln His Pro Ala Glu Glu Gly Arg Phe Ala Ala Leu Leu
            420                 425                 430

Leu Arg Leu Pro Ala Leu Arg Ser Ile Ser Leu Lys Cys Leu Asp His
            435                 440                 445

Leu Phe Phe Phe Arg Leu Ile Gly Asp Thr Pro Leu Glu Ser Phe Leu
        450                 455                 460

Val Asp Leu Leu Glu Ala Gly Pro Ile Gly
465                 470
```

<210> SEQ ID NO 34
<211> LENGTH: 1975
<212> TYPE: DNA
<213> ORGANISM: Ctenocephalides felis

<400> SEQUENCE: 34

| | | |
|---|---|---|
| tgcttgtaga aatattcgtg cagaaaaaat aactttgcag aatatttact tattctcatc | 60 |
| ttaatacata aaacttatct tttatccatg aatcggctca accgatcggt ccggcctcga | 120 |
| gtaaatccac aagaaaactc tcaagcggcg tatcgccaat caatctgaag aaaaacaggt | 180 |
| gatcgagaca tttcaaagag attgacctca gagctggcag gcgaagcagc agggctgcga | 240 |
| aacgaccctc ttccgctgga tgctgcgtcc tgcaatgctc gtccaggcac gcgtaaacct | 300 |
| tttctcgtaa agcatccact tcctgtctac atttcagtcc tcgaatatca ggattaaaca | 360 |
| gtattatagc cttcaaacag cctaattctg ctctgtccaa atccattctt ctcattttga | 420 |
| cacttaattc tgacagtacc cgatcgaaaa taggtccgac gccagcctgg attgcactat | 480 |
| tccgatgtaa cgtcatacca ggaaagaaac acattaattc aggcggtcct ggtggagcgc | 540 |
| gtctccttgt tgaagtatca ctagacatac tggacgtact tgtttctgca tcggattcta | 600 |
| gatactcaat acttctccag gctatagatg ctataagtaa ttcattccag gctgctctga | 660 |

-continued

```
gtaacgttac ttgatcctct aattgtaaag cactaaaatg cggcatgcac cttgcgtatt      720
gtactaactg atataactgt ttatttgctt gctgacacag actggataca gggcccttgt      780
atctaggagg caccatggat gaaggtccta ctcgcaaata ttgtatcgac aattccgggt      840
ccgtcgcaac atttcgagtt tcactccttt gttctgcttc taaaattctt tctaccgtta      900
aatcacgaac agaacttgtc gggttgcttt cttcattatt ctttgctcct cgttgtcgtt      960
cttcctgcac ggcttctcgt ttcattccac aggcgagaca tttctgatat cgacagaact     1020
gacatcgatt tctctgcctt tgtcgatca acaatttct atcctctcga caggcatacg       1080
tcagatcttt tcgtaccgtc cgtttgaaaa tcccttaca accttcgcaa ctgtaaacac      1140
cataatgctt cccggaagcc ctatctccgc atatggagca cagatgtttt gacccgctca    1200
aaggatgatt tggagggtat ggtgatttcg tttgggcgcc cgtggccgtg tttcctgata   1260
ctattgtgtg attttgacca aaaggcggac tagcgggact gccgacaact gcgccgccac   1320
tgccgggcga aaagccgccg ttcagtagcg caggatccgg tttcatatcc ggcagtgaga   1380
gcggtcccat cgagctcatt gacagccctt ggtcgagggc caagcctgta aggccagata   1440
atcctcgtcc ccatatttga ttctgagcgg ctccttgaat caaagccgtc acagacatca   1500
taggcttctc ttttttcatc attttagaag atatatttat ttattcccag ttgattgtaa   1560
tgcttaatta agttaccatt tatgcgtctc cttcatttct aatataaact cactcactga   1620
tatgtgtact agtcatgttg aatttcttaa tgacactttt tttatatttg acccttactt   1680 taagttttttg aggtaacatt tggagttacc aaaaaattga aattaacagt ttattcctat  1740
actcaattat aagcaacata taaactaata cgttcagtat gtcatctccc acatggggca   1800
ctgtcattca aaatctaata aacaattcct ttttatgaaa gcacaactct tatcacacag   1860
cacaaaaatt atctcgagac taaaactaaa cacaaaatat ttaaaatatc gttcatcttc   1920
gaacacgtca aaacaaaccg agtcgcgcgc ataccatcac ttcaatcact tgact         1975
```

<210> SEQ ID NO 35
<211> LENGTH: 1422
<212> TYPE: DNA
<213> ORGANISM: Ctenocephalides felis
<220> FEATURE:
<221> NAME/KEY: CDS
<222> LOCATION: (1)..(1422)
<223> OTHER INFORMATION:

<400> SEQUENCE: 35

```
atg atg aaa aaa gag aag cct atg atg tct gtg acg gct ttg att caa      48
Met Met Lys Lys Glu Lys Pro Met Met Ser Val Thr Ala Leu Ile Gln
1               5                   10                  15 gga gcc gct cag aat caa ata tgg gga cga gga tta tct ggc ctt aca      96
Gly Ala Ala Gln Asn Gln Ile Trp Gly Arg Gly Leu Ser Gly Leu Thr
            20                  25                  30 ggc ttg gcc ctc gac caa ggg ctg tca atg agc tcg atg gga ccg ctc    144
Gly Leu Ala Leu Asp Gln Gly Leu Ser Met Ser Ser Met Gly Pro Leu
        35                  40                  45 tca ctg ccg gat atg aaa ccg gat cct gcg cta ctg aac ggc ggc ttt    192
Ser Leu Pro Asp Met Lys Pro Asp Pro Ala Leu Leu Asn Gly Gly Phe
    50                  55                  60 tcg ccc ggc agt ggc ggc gca gtt gtc ggc agt ccc gct agt ccg cct    240
Ser Pro Gly Ser Gly Gly Ala Val Val Gly Ser Pro Ala Ser Pro Pro
65                  70                  75                  80 ttt ggt caa aat cac aca ata gta tca gga aac acg gcc acg ggc gcc    288
Phe Gly Gln Asn His Thr Ile Val Ser Gly Asn Thr Ala Thr Gly Ala
                85                  90                  95
```

-continued

| | |
|---|---|
| caa acg aaa tca cca tac cct cca aat cat cct ttg agc ggg tca aaa<br>Gln Thr Lys Ser Pro Tyr Pro Pro Asn His Pro Leu Ser Gly Ser Lys<br>    100                 105                 110 | 336 |
| cat ctg tgc tcc ata tgc gga gat agg gct tcc ggg aag cat tat ggt<br>His Leu Cys Ser Ile Cys Gly Asp Arg Ala Ser Gly Lys His Tyr Gly<br>            115                 120                 125 | 384 |
| gtt tac agt tgc gaa ggt tgt aag gga ttt ttc aaa cgg acg gta cga<br>Val Tyr Ser Cys Glu Gly Cys Lys Gly Phe Phe Lys Arg Thr Val Arg<br>130                 135                 140 | 432 |
| aaa gat ctg acg tat gcc tgt cga gag gat aga aat tgt ttg atc gac<br>Lys Asp Leu Thr Tyr Ala Cys Arg Glu Asp Arg Asn Cys Leu Ile Asp<br>145                 150                 155                 160 | 480 |
| aaa agg cag aga aat cga tgt cag ttc tgt cga tat cag aaa tgt ctc<br>Lys Arg Gln Arg Asn Arg Cys Gln Phe Cys Arg Tyr Gln Lys Cys Leu<br>                165                 170                 175 | 528 |
| gcc tgt gga atg aaa cga gaa gcc gtg cag gaa gaa cga caa cga gga<br>Ala Cys Gly Met Lys Arg Glu Ala Val Gln Glu Glu Arg Gln Arg Gly<br>            180                 185                 190 | 576 |
| gca aag aat aat gaa gaa agc aac ccg aca agt tct gtt cgt gat tta<br>Ala Lys Asn Asn Glu Glu Ser Asn Pro Thr Ser Ser Val Arg Asp Leu<br>        195                 200                 205 | 624 |
| acg gta gaa aga att tta gaa gca gaa caa agg agt gaa act cga aat<br>Thr Val Glu Arg Ile Leu Glu Ala Glu Gln Arg Ser Glu Thr Arg Asn<br>210                 215                 220 | 672 |
| gtt gcg acg gac ccg gaa ttg tcg ata caa tat ttg cga gta gga cct<br>Val Ala Thr Asp Pro Glu Leu Ser Ile Gln Tyr Leu Arg Val Gly Pro<br>225                 230                 235                 240 | 720 |
| tca tcc atg gtg cct cct aga tac aag ggc cct gta tcc agt ctg tgt<br>Ser Ser Met Val Pro Pro Arg Tyr Lys Gly Pro Val Ser Ser Leu Cys<br>                245                 250                 255 | 768 |
| cag caa gca aat aaa cag tta tat cag tta gta caa tac gca agg tgc<br>Gln Gln Ala Asn Lys Gln Leu Tyr Gln Leu Val Gln Tyr Ala Arg Cys<br>            260                 265                 270 | 816 |
| atg ccg cat ttt agt gct tta caa tta gag gat caa gta acg tta ctc<br>Met Pro His Phe Ser Ala Leu Gln Leu Glu Asp Gln Val Thr Leu Leu<br>        275                 280                 285 | 864 |
| aga gca gcc tgg aat gaa tta ctt ata gca tct ata gcc tgg aga agt<br>Arg Ala Ala Trp Asn Glu Leu Leu Ile Ala Ser Ile Ala Trp Arg Ser<br>    290                 295                 300 | 912 |
| att gag tat cta gaa tcc gat gca gaa aca agt acg tcc agt atg tct<br>Ile Glu Tyr Leu Glu Ser Asp Ala Glu Thr Ser Thr Ser Ser Met Ser<br>305                 310                 315                 320 | 960 |
| agt gat act tca aca agg aga cgc gct cca cca gga ccg cct gaa tta<br>Ser Asp Thr Ser Thr Arg Arg Arg Ala Pro Pro Gly Pro Pro Glu Leu<br>                325                 330                 335 | 1008 |
| atg tgt ttc ttt cct ggt atg acg tta cat cgg aat agt gca atc cag<br>Met Cys Phe Phe Pro Gly Met Thr Leu His Arg Asn Ser Ala Ile Gln<br>            340                 345                 350 | 1056 |
| gct ggc gtc gga cct att ttc gat cgg gta ctg tca gaa tta agt gtc<br>Ala Gly Val Gly Pro Ile Phe Asp Arg Val Leu Ser Glu Leu Ser Val<br>        355                 360                 365 | 1104 |
| aaa atg aga aga atg gat ttg gac aga gca gaa tta ggc tgt ttg aag<br>Lys Met Arg Arg Met Asp Leu Asp Arg Ala Glu Leu Gly Cys Leu Lys<br>    370                 375                 380 | 1152 |
| gct ata ata ctg ttt aat cct gat att cga gga ctg aaa tgt aga cag<br>Ala Ile Ile Leu Phe Asn Pro Asp Ile Arg Gly Leu Lys Cys Arg Gln<br>385                 390                 395                 400 | 1200 |
| gaa gtg gat gct tta cga gaa aag gtt tac gcg tgc ctg gac gag cat<br>Glu Val Asp Ala Leu Arg Glu Lys Val Tyr Ala Cys Leu Asp Glu His | 1248 |

-continued

```
                405                 410                 415
tgc agg acg cag cat cca gcg gaa gag ggt cgt ttc gca gcc ctg ctg    1296
Cys Arg Thr Gln His Pro Ala Glu Glu Gly Arg Phe Ala Ala Leu Leu
            420                 425                 430 ctt cgc ctg cca gct ctg agg tca atc tct ttg aaa tgt ctc gat cac    1344
Leu Arg Leu Pro Ala Leu Arg Ser Ile Ser Leu Lys Cys Leu Asp His
        435                 440                 445 ctg ttt ttc ttc aga ttg att ggc gat acg ccg ctt gag agt ttt ctt    1392
Leu Phe Phe Phe Arg Leu Ile Gly Asp Thr Pro Leu Glu Ser Phe Leu
450                 455                 460 gtg gat tta ctc gag gcc gga ccg atc ggt                            1422
Val Asp Leu Leu Glu Ala Gly Pro Ile Gly
465                 470
```

<210> SEQ ID NO 36
<211> LENGTH: 474
<212> TYPE: PRT
<213> ORGANISM: Ctenocephalides felis

<400> SEQUENCE: 36

```
Met Met Lys Lys Glu Lys Pro Met Met Ser Val Thr Ala Leu Ile Gln
1               5                   10                  15

Gly Ala Ala Gln Asn Gln Ile Trp Gly Arg Gly Leu Ser Gly Leu Thr
            20                  25                  30

Gly Leu Ala Leu Asp Gln Gly Leu Ser Met Ser Ser Met Gly Pro Leu
        35                  40                  45

Ser Leu Pro Asp Met Lys Pro Asp Pro Ala Leu Leu Asn Gly Gly Phe
    50                  55                  60

Ser Pro Gly Ser Gly Gly Ala Val Val Gly Ser Pro Ala Ser Pro Pro
65                  70                  75                  80

Phe Gly Gln Asn His Thr Ile Val Ser Gly Asn Thr Ala Thr Gly Ala
                85                  90                  95

Gln Thr Lys Ser Pro Tyr Pro Pro Asn His Pro Leu Ser Gly Ser Lys
            100                 105                 110

His Leu Cys Ser Ile Cys Gly Asp Arg Ala Ser Gly Lys His Tyr Gly
        115                 120                 125

Val Tyr Ser Cys Glu Gly Cys Lys Gly Phe Phe Lys Arg Thr Val Arg
    130                 135                 140

Lys Asp Leu Thr Tyr Ala Cys Arg Glu Asp Arg Asn Cys Leu Ile Asp
145                 150                 155                 160

Lys Arg Gln Arg Asn Arg Cys Gln Phe Cys Arg Tyr Gln Lys Cys Leu
                165                 170                 175

Ala Cys Gly Met Lys Arg Glu Ala Val Gln Glu Glu Arg Gln Arg Gly
            180                 185                 190

Ala Lys Asn Asn Glu Glu Ser Asn Pro Thr Ser Ser Val Arg Asp Leu
        195                 200                 205

Thr Val Glu Arg Ile Leu Glu Ala Glu Gln Arg Ser Glu Thr Arg Asn
    210                 215                 220

Val Ala Thr Asp Pro Glu Leu Ser Ile Gln Tyr Leu Arg Val Gly Pro
225                 230                 235                 240

Ser Ser Met Val Pro Pro Arg Tyr Lys Gly Pro Val Ser Ser Leu Cys
                245                 250                 255

Gln Gln Ala Asn Lys Gln Leu Tyr Gln Leu Val Gln Tyr Ala Arg Cys
            260                 265                 270

Met Pro His Phe Ser Ala Leu Gln Leu Glu Asp Gln Val Thr Leu Leu
        275                 280                 285
```

-continued

```
Arg Ala Ala Trp Asn Glu Leu Leu Ile Ala Ser Ile Ala Trp Arg Ser
    290                 295                 300

Ile Glu Tyr Leu Glu Ser Asp Ala Glu Thr Ser Thr Ser Ser Met Ser
305                 310                 315                 320

Ser Asp Thr Ser Thr Arg Arg Arg Ala Pro Pro Gly Pro Pro Glu Leu
                325                 330                 335

Met Cys Phe Phe Pro Gly Met Thr Leu His Arg Asn Ser Ala Ile Gln
                340                 345                 350

Ala Gly Val Gly Pro Ile Phe Asp Arg Val Leu Ser Glu Leu Ser Val
            355                 360                 365

Lys Met Arg Arg Met Asp Leu Asp Arg Ala Glu Leu Gly Cys Leu Lys
370                 375                 380

Ala Ile Ile Leu Phe Asn Pro Asp Ile Arg Gly Leu Lys Cys Arg Gln
385                 390                 395                 400

Glu Val Asp Ala Leu Arg Glu Lys Val Tyr Ala Cys Leu Asp Glu His
                405                 410                 415

Cys Arg Thr Gln His Pro Ala Glu Glu Gly Arg Phe Ala Ala Leu Leu
                420                 425                 430

Leu Arg Leu Pro Ala Leu Arg Ser Ile Ser Leu Lys Cys Leu Asp His
        435                 440                 445

Leu Phe Phe Phe Arg Leu Ile Gly Asp Thr Pro Leu Glu Ser Phe Leu
    450                 455                 460

Val Asp Leu Leu Glu Ala Gly Pro Ile Gly
465                 470
```

<210> SEQ ID NO 37
<211> LENGTH: 1422
<212> TYPE: DNA
<213> ORGANISM: Ctenocephalides felis

<400> SEQUENCE: 37

```
accgatcggt ccggcctcga gtaaatccac aagaaaactc tcaagcggcg tatcgccaat      60
caatctgaag aaaaacaggt gatcgagaca tttcaaagag attgacctca gagctggcag     120
gcgaagcagc agggctgcga acgaccctc ttccgctgga tgctgcgtcc tgcaatgctc     180
gtccaggcac gcgtaaacct tttctcgtaa agcatccact tcctgtctac atttcagtcc     240
tcgaatatca ggattaaaca gtattatagc cttcaaacag cctaattctg ctctgtccaa     300
atccattctt ctcattttga cacttaattc tgacagtacc cgatcgaaaa taggtccgac     360
gccagcctgg attgcactat tccgatgtaa cgtcatacca ggaaagaaac acattaattc     420
aggcggtcct ggtggagcgc gtctccttgt tgaagtatca ctagacatac tggacgtact     480
tgtttctgca tcggattcta gatactcaat acttctccag gctatagatg ctataagtaa     540
ttcattccag gctgctctga gtaacgttac ttgatcctct aattgtaaag cactaaaatg     600
cggcatgcac cttgcgtatt gtactaactg atataactgt ttatttgctt gctgacacag     660
actggataca gggcccttgt atctaggagg caccatggat gaaggtccta ctcgcaaata     720
ttgtatcgac aattccgggt ccgtcgcaac atttcgagtt tcactccttt gttctgcttc     780
taaaattctt tctaccgtta aatcacgaac agaacttgtc gggttgcttt cttcattatt     840
ctttgctcct cgttgtcgtt cttcctgcac ggcttctcgt ttcattccac aggcgagaca     900
tttctgatat cgacagaact gacatcgatt tctctgcctt ttgtcgatca aacaatttct     960
atcctctcga caggcatacg tcagatcttt tcgtaccgtc cgtttgaaaa atcccttaca    1020
```

```
accttcgcaa ctgtaaacac cataatgctt cccggaagcc ctatctccgc atatggagca    1080
cagatgtttt gacccgctca aaggatgatt tggagggtat ggtgatttcg tttgggcgcc    1140
cgtggccgtg tttcctgata ctattgtgtg attttgacca aaaggcggac tagcgggact    1200
gccgacaact gcgccgccac tgccgggcga aaagccgccg ttcagtagcg caggatccgg    1260
tttcatatcc ggcagtgaga gcggtcccat cgagctcatt gacagcccct ggtcgagggc    1320
caagcctgta aggccagata atcctcgtcc ccatatttga ttctgagcgg ctccttgaat    1380
caaagccgtc acagacatca taggcttctc tttttttcatc at                      1422
```

<210> SEQ ID NO 38
<211> LENGTH: 612
<212> TYPE: DNA
<213> ORGANISM: Ctenocephalides felis

<400> SEQUENCE: 38

```
tctgaggaag acctacgaag gataatgata agtacaccag ctgaagatga agctcttgaa     60
tttcggcata taactgaaat taccatactt actgtgcagc ttatagtgga atttgcaaag    120
ggtttaccag cttttaccaa aataccacaa gaagatcaaa taacattatt aaaggcatgt    180
tcaagtgaag taatgatgct gcgaatggct cggcggtacg atgcagtgtc ggattcaatc    240
ttattcgcga ataatcgttc atatactcgt gactcctata aaatggctgg tatggcagat    300
acaatagaag atctattgca ttttttgtcga cagatgtata ctatgactgt agacaatgtg    360
gagtatgcac taataacagc aattgtgatt ttttcagatc gacctggatt ggaacaagca    420
gatcttgtgg aacaaattca aagttattac atcaaaacat taaagtgcta cattttgaat    480
cgacatagtg gtgaccctaa gtgtggaata ttgtttgcca aacttctttc tattcttact    540
gaattacgca cgttaggaaa tcaaaactca gaaatgtgtt ttgcactgaa attgaagaac    600
agaaaacttc ct                                                       612
```

<210> SEQ ID NO 39
<211> LENGTH: 612
<212> TYPE: DNA
<213> ORGANISM: Ctenocephalides felis

<400> SEQUENCE: 39

```
aggaagtttt ctgttcttca atttcagtgc aaaacacatt tctgagtttt gatttcctaa     60
cgtgcgtaat tcagtaagaa tagaaagaag tttggcaaac aatattccac acttagggtc    120
accactatgt cgattcaaaa tgtagcactt taatgttttg atgtaataac tttgaatttg    180
ttccacaaga tctgcttgtt ccaatccagg tcgatctgaa aaaatcacaa ttgctgttat    240
tagtgcatac tccacattgt ctacagtcat agtatacatc tgtcgacaaa aatgcaaatag    300 atcttctatt gtatctgcca taccagccat tttataggag tcacgagtat atgaacgatt    360
attcgcgaat aagattgaat ccgacactgc atcgtaccgc cgagccattc gcagcatcat    420
tacttcactt gaacatgcct ttaataatgt tatttgatct tcttgtggta ttttggtaaa    480
agctggtaaa ccctttgcaa attccactat aagctgcaca gtaagtatgg taatttcagt    540
tatatgccga aattcaagag cttcatcttc agctggtgta cttatcatta tccttcgtag    600
gtcttcctca ga                                                       612
```

<210> SEQ ID NO 40
<211> LENGTH: 776
<212> TYPE: DNA
<213> ORGANISM: Ctenocephalides felis -continued

<400> SEQUENCE: 40

| gaaagaattt tagaagcaga acaaaggagt gaaactcgaa atgttgcgac ggacccggaa | 60 |
| ttgtcgatac aatatttgcg agtaggacct tcatccatgg tgcctcctag atacaagggc | 120 |
| cctgtatcca gtctgtgtca gcaagcaaat aaacagttat atcagttagt acaatacgca | 180 |
| aggtgcatgc cgcattttag tgctttacaa ttagaggatc aagtaacgtt actcagagca | 240 |
| gcctggaatg aattacttat agcatctata gcctggagaa gtattgagta tctagaatcc | 300 |
| gatgcagaaa caagtacgtc cagtatgtct agtgatactt caacaaggag acgcgctcca | 360 |
| ccaggaccgc ctgaattaat gtgtttcttt cctggtatga cgttacatcg aatagtgca | 420 |
| atccaggctg gcgtcggacc tattttcgat cgggtactgt cagaattaag tgtcaaaatg | 480 |
| agaagaatgg atttggacag agcagaatta ggctgtttga aggctataat actgtttaat | 540 |
| cctgatattc gaggactgaa atgtagacag gaagtggatg ctttacgaga aaaggtttac | 600 |
| gcgtgcctgg acgagcattg caggacgcag catccagcgg aagagggtcg tttcgcagcc | 660 |
| ctgctgcttc gcctgccagc tctgaggtca atctctttga aatgtctcga tcacctgttt | 720 |
| ttcttcagat tgattggcga tacgccgctt gagagttttc ttgtggattt actcga | 776 |

<210> SEQ ID NO 41
<211> LENGTH: 776
<212> TYPE: DNA
<213> ORGANISM: Ctenocephalides felis

<400> SEQUENCE: 41

| tcgagtaaat ccacaagaaa actctcaagc ggcgtatcgc caatcaatct gaagaaaaac | 60 |
| aggtgatcga gacatttcaa agagattgac ctcagagctg gcaggcgaag cagcagggct | 120 |
| gcgaaacgac cctcttccgc tggatgctgc gtcctgcaat gctcgtccag gcacgcgtaa | 180 |
| accttttctc gtaaagcatc cacttcctgt ctacatttca gtcctcgaat atcaggatta | 240 |
| aacagtatta tagccttcaa acagcctaat tctgctctgt ccaaatccat tcttctcatt | 300 |
| ttgacactta attctgacag tacccgatcg aaaataggtc cgacgccagc ctggattgca | 360 |
| ctattccgat gtaacgtcat accaggaaag aaacacatta attcaggcgg tcctggtgga | 420 |
| gcgcgtctcc ttgttgaagt atcactagac atactgacg tacttgtttc tgcatcggat | 480 |
| tctagatact caatacttct ccaggctata gatgctataa gtaattcatt ccaggctgct | 540 |
| ctgagtaacg ttacttgatc ctctaattgt aaagcactaa aatgcggcat gcaccttgcg | 600 |
| tattgtacta actgatataa ctgtttattt gcttgctgac acagactgga tacagggccc | 660 |
| ttgtatctag gaggcaccat ggatgaaggt cctactcgca aatattgtat cgacaattcc | 720 |
| gggtccgtcg caacatttcg agtttcactc ctttgttctg cttctaaaat tcttc | 776 |

<210> SEQ ID NO 42
<211> LENGTH: 943
<212> TYPE: DNA
<213> ORGANISM: Ctenocephalides felis

<400> SEQUENCE: 42

| gaggtatata ttaatgtatc gattaaataa ggaggaataa accatggggg gttctcatca | 60 |
| tcatcatcat catggtatgg ctagcatgac tggtggacag caaatgggtc gggatctgta | 120 |
| cgacgatgac gataaggatc cctctgttcg agatttaacg gtagaaagaa ttttagaagc | 180 |
| ggaacaaagg agtgaaactc gaaatgttgc gacggacccg gaattgtcga tacaatattt | 240 |

| | |
|---|---|
| gcgagtagga ccttcatcca tggtgcctcc tagatacaag ggccctgtat ccagtctgtg | 300 |
| tcagcaagca aataaacagt tatatcagtt agtacaatac gcaaggtgca tgccgcattt | 360 |
| tagtgcttta caattagagg atcaagtaac gttactcaga gcagcctgga atgaattact | 420 |
| tatagcatct atagcctgga gaagtattga gtatctagaa tccgatgcag aaacaagtac | 480 |
| gtccagtatg tctagtgata cttcaacaag gagacgcgct ccaccaggac cgcctgaatt | 540 |
| aatgtgtttc cttcctggta tgacgttaca tcggaatagt gcaatccagg ctggcgtcgg | 600 |
| acctaatttc gatcgggtac tgtcagaatt aagtgtcaaa atgagaagaa tggatttgga | 660 |
| cagagcagaa ttaggctgtt tgaaggctat aatactgttt aatcctgata ttcgaggact | 720 |
| gaaatgtaga caggaagtgg atgctttacg agaaaaggtt tacgcgtgcc tggacgagca | 780 |
| ttgcaggacg cagcatccag cggaagaggg tcgtttcgca gccctgctgc ttcgcctgcc | 840 |
| agctctgagg tcaatctctt tgaaatgtct cgatcacctg tttttcttca gattgattgg | 900 |
| cgatacgccg cttgagagtt ttcttgtgga tttactcgag gcc | 943 |

<210> SEQ ID NO 43
<211> LENGTH: 943
<212> TYPE: DNA
<213> ORGANISM: Ctenocephalides felis

<400> SEQUENCE: 43

| | |
|---|---|
| ggcctcgagt aaatccacaa gaaaactctc aagcggcgta tcgccaatca atctgaagaa | 60 |
| aaacaggtga tcgagacatt tcaaagagat tgacctcaga gctggcaggc gaagcagcag | 120 |
| ggctgcgaaa cgaccctctt ccgctggatg ctgcgtcctg caatgctcgt ccaggcacgc | 180 |
| gtaaacctt tctcgtaaag catccacttc ctgtctacat ttcagtcctc gaatatcagg | 240 |
| attaaacagt attatagcct tcaaacagcc taattctgct ctgtccaaat ccattcttct | 300 |
| cattttgaca cttaattctg acagtacccg atcgaaatta ggtccgacgc cagcctggat | 360 |
| tgcactattc cgatgtaacg tcataccagg aaggaaacac attaattcag gcggtcctgg | 420 |
| tggagcgcgt ctccttgttg aagtatcact agacatactg gacgtacttg tttctgcatc | 480 |
| ggattctaga tactcaatac ttctccaggc tatagatgct ataagtaatt cattccaggc | 540 |
| tgctctgagt aacgttactt gatcctctaa ttgtaaagca ctaaaatgcg gcatgcacct | 600 |
| tgcgtattgt actaactgat ataactgttt atttgcttgc tgacacagac tggatacagg | 660 |
| gcccttgtat ctaggaggca ccatggatga aggtcctact cgcaaatatt gtatcgacaa | 720 |
| ttccgggtcc gtcgcaacat ttcgagtttc actcctttgt tccgcttcta aaattctttc | 780 |
| taccgttaaa tctcgaacag agggatcctt atcgtcatcg tcgtacagat cccgacccat | 840 |
| ttgctgtcca ccagtcatgc tagccatacc atgatgatga tgatgatgag aaccccccat | 900 |
| ggtttattcc tccttattta atcgatacat taatatatac ctc | 943 |

<210> SEQ ID NO 44
<211> LENGTH: 21
<212> TYPE: DNA
<213> ORGANISM: Artificial sequence
<220> FEATURE:
<223> OTHER INFORMATION: Synthetic Primer

<400> SEQUENCE: 44

| | |
|---|---|
| tgygaaatgg ayatgtayat g | 21 |

<210> SEQ ID NO 45
<211> LENGTH: 20

```
<212> TYPE: DNA
<213> ORGANISM: Artificial sequence
<220> FEATURE:
<223> OTHER INFORMATION: Synthetic Primer
<220> FEATURE:
<221> NAME/KEY: misc_feature
<222> LOCATION: (15)..(15)
<223> OTHER INFORMATION: n = unknown

<400> SEQUENCE: 45
ccyttwgcra attcnacdat                                              20

<210> SEQ ID NO 46
<211> LENGTH: 18
<212> TYPE: DNA
<213> ORGANISM: Artificial sequence
<220> FEATURE:
<223> OTHER INFORMATION: Synthetic Primer

<400> SEQUENCE: 46
ggttcccgaa aaccaatg                                                18

<210> SEQ ID NO 47
<211> LENGTH: 19
<212> TYPE: DNA
<213> ORGANISM: Artificial sequence
<220> FEATURE:
<223> OTHER INFORMATION: Synthetic Primer

<400> SEQUENCE: 47
gccgaaattc aagagcttc                                               19

<210> SEQ ID NO 48
<211> LENGTH: 18
<212> TYPE: DNA
<213> ORGANISM: Artificial sequence
<220> FEATURE:
<223> OTHER INFORMATION: Synthetic Primer

<400> SEQUENCE: 48
gtcaggaatg taggctca                                                18

<210> SEQ ID NO 49
<211> LENGTH: 20
<212> TYPE: DNA
<213> ORGANISM: Artificial sequence
<220> FEATURE:
<223> OTHER INFORMATION: Synthetic Primer

<400> SEQUENCE: 49
aattaaccct cactaaaggg                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic Primer

<400> SEQUENCE: 50
ggwaaacayt atggwgtwta                                              20

<210> SEQ ID NO 51
<211> LENGTH: 18
<212> TYPE: DNA
<213> ORGANISM: Artificial sequence
<220> FEATURE:
```

```
<223> OTHER INFORMATION: Synthetic Primer
<220> FEATURE:
<221> NAME/KEY: misc_feature
<222> LOCATION: (10)..(10)
<223> OTHER INFORMATION: n = unknown

<400> SEQUENCE: 51
ttcttcytgn acwhcttc                                                 18

<210> SEQ ID NO 52
<211> LENGTH: 20
<212> TYPE: DNA
<213> ORGANISM: Artificial sequence
<220> FEATURE:
<223> OTHER INFORMATION: Synthetic Primer

<400> SEQUENCE: 52
ttctcgtttc attccacagg                                               20

<210> SEQ ID NO 53
<211> LENGTH: 29
<212> TYPE: DNA
<213> ORGANISM: Artificial sequence
<220> FEATURE:
<223> OTHER INFORMATION: Synthetic Primer

<400> SEQUENCE: 53
aaagggaaca aaagctggag ctccaccgc                                     29

<210> SEQ ID NO 54
<211> LENGTH: 28
<212> TYPE: DNA
<213> ORGANISM: Artificial sequence
<220> FEATURE:
<223> OTHER INFORMATION: Synthetic Primer

<400> SEQUENCE: 54
ttaaaatatc actggttcgt atcctccc                                      28

<210> SEQ ID NO 55
<211> LENGTH: 26
<212> TYPE: DNA
<213> ORGANISM: Artificial sequence
<220> FEATURE:
<223> OTHER INFORMATION: Synthetic Primer

<400> SEQUENCE: 55
ggcggccgct ctagaactag tggatc                                        26

<210> SEQ ID NO 56
<211> LENGTH: 23
<212> TYPE: DNA
<213> ORGANISM: Artificial sequence
<220> FEATURE:
<223> OTHER INFORMATION: Synthetic Primer

<400> SEQUENCE: 56
agacaatcaa tatcccaagt gcg                                           23

<210> SEQ ID NO 57
<211> LENGTH: 27
<212> TYPE: DNA
<213> ORGANISM: Artificial sequence
<220> FEATURE:
<223> OTHER INFORMATION: Synthetic Primer

<400> SEQUENCE: 57
```

```
ctgcataaaa tgcctaaagt cgcggac                                              27
```

<210> SEQ ID NO 58
<211> LENGTH: 30
<212> TYPE: DNA
<213> ORGANISM: Artificial sequence
<220> FEATURE:
<223> OTHER INFORMATION: Synthetic Primer

<400> SEQUENCE: 58

```
gcgggatccc aagatggata tgaacaacct                                           30
```

<210> SEQ ID NO 59
<211> LENGTH: 36
<212> TYPE: DNA
<213> ORGANISM: Artificial sequence
<220> FEATURE:
<223> OTHER INFORMATION: Synthetic Primer

<400> SEQUENCE: 59

```
gcggaattct caatcccaaa tttcttctaa aaatct                                    36
```

<210> SEQ ID NO 60
<211> LENGTH: 31
<212> TYPE: DNA
<213> ORGANISM: Artificial sequence
<220> FEATURE:
<223> OTHER INFORMATION: Synthetic Primer

<400> SEQUENCE: 60

```
gcgggatccc tctgttcgag atttaacggt a                                         31
```

<210> SEQ ID NO 61
<211> LENGTH: 27
<212> TYPE: DNA
<213> ORGANISM: Artificial sequence
<220> FEATURE:
<223> OTHER INFORMATION: Synthetic Primer

<400> SEQUENCE: 61

```
gcgaagcttt caaccgatgg gtccgcc                                              27
```

<210> SEQ ID NO 62
<211> LENGTH: 36
<212> TYPE: DNA
<213> ORGANISM: Artificial sequence
<220> FEATURE:
<223> OTHER INFORMATION: Synthetic Primer

<400> SEQUENCE: 62

```
gcgcccgggg gattaacttt attattaaaa attaaa                                    36
```

<210> SEQ ID NO 63
<211> LENGTH: 33
<212> TYPE: DNA
<213> ORGANISM: Artificial sequence
<220> FEATURE:
<223> OTHER INFORMATION: Synthetic Primer

<400> SEQUENCE: 63

```
gcgcgcggcc gcaagctttc aaccgatggg tcc                                       33
```

<210> SEQ ID NO 64
<211> LENGTH: 66
<212> TYPE: PRT

<213> ORGANISM: Ctenocephalides felis

<400> SEQUENCE: 64

```
Cys Leu Val Cys Gly Asp Arg Ala Ser Gly Tyr His Tyr Asn Ala Leu
1               5                   10                  15
Thr Cys Glu Gly Cys Lys Gly Phe Phe Arg Arg Ser Val Thr Lys Asn
            20                  25                  30
Ala Val Tyr Val Cys Lys Phe Gly His Thr Cys Glu Met Asp Met Tyr
        35                  40                  45
Met Arg Arg Lys Cys Gln Glu Cys Arg Leu Lys Cys Leu Ala Val
    50                  55                  60
Gly Met
65
```

<210> SEQ ID NO 65
<211> LENGTH: 219
<212> TYPE: PRT
<213> ORGANISM: Ctenocephalides felis

<400> SEQUENCE: 65

```
Gln Asp Gly Tyr Glu Gln Pro Ser Glu Glu Asp Leu Arg Arg Ile Met
1               5                   10                  15
Ile Ser Thr Pro Ala Glu Asp Glu Ala Leu Glu Phe Arg His Ile Thr
            20                  25                  30
Glu Ile Thr Ile Leu Thr Val Gln Leu Ile Val Glu Phe Ala Lys Gly
        35                  40                  45
Leu Pro Ala Phe Thr Lys Ile Pro Gln Glu Asp Gln Ile Thr Leu Leu
    50                  55                  60
Lys Ala Cys Ser Ser Glu Val Met Met Leu Arg Met Ala Arg Arg Tyr
65                  70                  75                  80
Asp Ala Val Ser Asp Ser Ile Leu Phe Ala Asn Asn Arg Ser Tyr Thr
                85                  90                  95
Arg Asp Ser Tyr Lys Met Ala Gly Met Ala Asp Thr Ile Glu Asp Leu
            100                 105                 110
Leu His Phe Cys Arg Gln Met Tyr Thr Met Thr Val Asp Asn Val Glu
        115                 120                 125
Tyr Ala Leu Ile Thr Ala Ile Val Ile Phe Ser Asp Arg Pro Gly Leu
    130                 135                 140
Glu Gln Ala Asp Leu Val Glu Gln Ile Gln Ser Tyr Tyr Ile Lys Thr
145                 150                 155                 160
Leu Lys Cys Tyr Ile Leu Asn Arg His Ser Gly Asp Pro Lys Cys Gly
                165                 170                 175
Ile Leu Phe Ala Lys Leu Leu Ser Ile Leu Thr Glu Leu Arg Thr Leu
            180                 185                 190
Gly Asn Gln Asn Ser Glu Met Cys Phe Ala Leu Lys Leu Lys Asn Arg
        195                 200                 205
Lys Leu Pro Arg Phe Leu Glu Glu Ile Trp Asp
    210                 215
```

<210> SEQ ID NO 66
<211> LENGTH: 66
<212> TYPE: PRT
<213> ORGANISM: Ctenocephalides felis

<400> SEQUENCE: 66

```
Cys Leu Val Cys Gly Asp Arg Ala Ser Gly Tyr His Tyr Asn Ala Leu
1               5                   10                  15
```

-continued

```
Thr Cys Glu Gly Cys Lys Gly Phe Phe Arg Arg Ser Val Thr Lys Asn
             20                  25                  30

Ala Val Tyr Val Cys Lys Phe Gly His Thr Cys Glu Met Asp Met Tyr
         35                  40                  45

Met Arg Arg Lys Cys Gln Glu Cys Arg Leu Lys Lys Cys Leu Ala Val
 50                  55                  60

Gly Met
 65

<210> SEQ ID NO 67
<211> LENGTH: 219
<212> TYPE: PRT
<213> ORGANISM: Ctenocephalides felis

<400> SEQUENCE: 67

Gln Asp Gly Tyr Glu Gln Pro Ser Glu Glu Leu Arg Arg Ile Met
 1               5                  10                  15

Ile Ser Thr Pro Ala Glu Asp Glu Ala Leu Glu Phe Arg His Ile Thr
             20                  25                  30

Glu Ile Thr Ile Leu Thr Val Gln Leu Ile Val Glu Phe Ala Lys Gly
         35                  40                  45

Leu Pro Ala Phe Thr Lys Ile Pro Gln Glu Asp Gln Ile Thr Leu Leu
 50                  55                  60

Lys Ala Cys Ser Ser Glu Val Met Met Leu Arg Met Ala Arg Arg Tyr
 65                  70                  75                  80

Asp Ala Val Ser Asp Ser Ile Leu Phe Ala Asn Asn Arg Ser Tyr Thr
                 85                  90                  95

Arg Asp Ser Tyr Lys Met Ala Gly Met Ala Asp Thr Ile Glu Asp Leu
            100                 105                 110

Leu His Phe Cys Arg Gln Met Tyr Thr Met Thr Val Asp Asn Val Glu
        115                 120                 125

Tyr Ala Leu Ile Thr Ala Ile Val Ile Phe Ser Asp Arg Pro Gly Leu
    130                 135                 140

Glu Gln Ala Asp Leu Val Glu Gln Ile Gln Ser Tyr Tyr Ile Lys Thr
145                 150                 155                 160

Leu Lys Cys Tyr Ile Leu Asn Arg His Ser Gly Asp Pro Lys Cys Gly
                165                 170                 175

Ile Leu Phe Ala Lys Leu Leu Ser Ile Leu Thr Glu Leu Arg Thr Leu
            180                 185                 190

Gly Asn Gln Asn Ser Glu Met Cys Phe Ala Leu Lys Leu Lys Asn Arg
        195                 200                 205

Lys Leu Pro Arg Phe Leu Glu Glu Ile Trp Asp
    210                 215

<210> SEQ ID NO 68
<211> LENGTH: 66
<212> TYPE: PRT
<213> ORGANISM: Ctenocephalides felis

<400> SEQUENCE: 68

Cys Ser Ile Cys Gly Asp Arg Ala Ser Gly Lys His Tyr Gly Val Tyr
 1               5                  10                  15

Ser Cys Glu Gly Cys Lys Gly Phe Phe Lys Arg Thr Val Arg Lys Asp
             20                  25                  30

Leu Thr Tyr Ala Cys Arg Glu Asp Arg Asn Cys Leu Ile Asp Lys Arg
         35                  40                  45
```

```
Gln Arg Asn Arg Cys Gln Phe Cys Arg Tyr Gln Lys Cys Leu Ala Cys
    50                  55                  60

Gly Met
65

<210> SEQ ID NO 69
<211> LENGTH: 271
<212> TYPE: PRT
<213> ORGANISM: Ctenocephalides felis

<400> SEQUENCE: 69

Ser Val Arg Asp Leu Thr Val Glu Arg Ile Leu Glu Ala Glu Gln Arg
1               5                   10                  15

Ser Glu Thr Arg Asn Val Ala Thr Asp Pro Glu Leu Ser Ile Gln Tyr
            20                  25                  30

Leu Arg Val Gly Pro Ser Ser Met Val Pro Pro Arg Tyr Lys Gly Pro
        35                  40                  45

Val Ser Ser Leu Cys Gln Gln Ala Asn Lys Gln Leu Tyr Gln Leu Val
    50                  55                  60

Gln Tyr Ala Arg Cys Met Pro His Phe Ser Ala Leu Gln Leu Glu Asp
65                  70                  75                  80

Gln Val Thr Leu Leu Arg Ala Ala Trp Asn Glu Leu Leu Ile Ala Ser
                85                  90                  95

Ile Ala Trp Arg Ser Ile Glu Tyr Leu Glu Ser Asp Ala Glu Thr Ser
            100                 105                 110

Thr Ser Ser Met Ser Ser Asp Thr Ser Thr Arg Arg Arg Ala Pro Pro
        115                 120                 125

Gly Pro Pro Glu Leu Met Cys Phe Phe Pro Gly Met Thr Leu His Arg
    130                 135                 140

Asn Ser Ala Ile Gln Ala Gly Val Gly Pro Ile Phe Asp Arg Val Leu
145                 150                 155                 160

Ser Glu Leu Ser Val Lys Met Arg Arg Met Asp Leu Asp Arg Ala Glu
                165                 170                 175

Leu Gly Cys Leu Lys Ala Ile Ile Leu Phe Asn Pro Asp Ile Arg Gly
            180                 185                 190

Leu Lys Cys Arg Gln Glu Val Asp Ala Leu Arg Glu Lys Val Tyr Ala
        195                 200                 205

Cys Leu Asp Glu His Cys Arg Thr Gln His Pro Ala Glu Glu Gly Arg
    210                 215                 220

Phe Ala Ala Leu Leu Leu Arg Leu Pro Ala Leu Arg Ser Ile Ser Leu
225                 230                 235                 240

Lys Cys Leu Asp His Leu Phe Phe Arg Leu Ile Gly Asp Thr Pro
                245                 250                 255

Leu Glu Ser Phe Leu Val Asp Leu Leu Glu Ala Gly Pro Ile Gly
            260                 265                 270

<210> SEQ ID NO 70
<211> LENGTH: 66
<212> TYPE: PRT
<213> ORGANISM: Ctenocephalides felis

<400> SEQUENCE: 70

Cys Ser Ile Cys Gly Asp Arg Ala Ser Gly Lys His Tyr Gly Val Tyr
1               5                   10                  15

Ser Cys Glu Gly Cys Lys Gly Phe Phe Lys Arg Thr Val Arg Lys Asp
            20                  25                  30
```

-continued

```
Leu Thr Tyr Ala Cys Arg Glu Asp Arg Asn Cys Leu Ile Asp Lys Arg
             35                  40                  45

Gln Arg Asn Arg Cys Gln Phe Cys Arg Tyr Gln Lys Cys Leu Ala Cys
         50                  55                  60

Gly Met
 65

<210> SEQ ID NO 71
<211> LENGTH: 271
<212> TYPE: PRT
<213> ORGANISM: Ctenocephalides felis

<400> SEQUENCE: 71

Ser Val Arg Asp Leu Thr Val Glu Arg Ile Leu Glu Ala Glu Gln Arg
  1               5                  10                  15

Ser Glu Thr Arg Asn Val Ala Thr Asp Pro Glu Leu Ser Ile Gln Tyr
             20                  25                  30

Leu Arg Val Gly Pro Ser Ser Met Val Pro Pro Arg Tyr Lys Gly Pro
         35                  40                  45

Val Ser Ser Leu Cys Gln Gln Ala Asn Lys Gln Leu Tyr Gln Leu Val
     50                  55                  60

Gln Tyr Ala Arg Cys Met Pro His Phe Ser Ala Leu Gln Leu Glu Asp
 65                  70                  75                  80

Gln Val Thr Leu Leu Arg Ala Ala Trp Asn Glu Leu Leu Ile Ala Ser
                 85                  90                  95

Ile Ala Trp Arg Ser Ile Glu Tyr Leu Glu Ser Asp Ala Glu Thr Ser
                100                 105                 110

Thr Ser Ser Met Ser Ser Asp Thr Ser Thr Arg Arg Ala Pro Pro
             115                 120                 125

Gly Pro Pro Glu Leu Met Cys Phe Phe Pro Gly Met Thr Leu His Arg
        130                 135                 140

Asn Ser Ala Ile Gln Ala Gly Val Gly Pro Ile Phe Asp Arg Val Leu
145                 150                 155                 160

Ser Glu Leu Ser Val Lys Met Arg Arg Met Asp Leu Asp Arg Ala Glu
                165                 170                 175

Leu Gly Cys Leu Lys Ala Ile Ile Leu Phe Asn Pro Asp Ile Arg Gly
            180                 185                 190

Leu Lys Cys Arg Gln Glu Val Asp Ala Leu Arg Glu Lys Val Tyr Ala
        195                 200                 205

Cys Leu Asp Glu His Cys Arg Thr Gln His Pro Ala Glu Glu Gly Arg
    210                 215                 220

Phe Ala Ala Leu Leu Leu Arg Leu Pro Ala Leu Arg Ser Ile Ser Leu
225                 230                 235                 240

Lys Cys Leu Asp His Leu Phe Phe Arg Leu Ile Gly Asp Thr Pro
                245                 250                 255

Leu Glu Ser Phe Leu Val Asp Leu Leu Glu Ala Gly Pro Ile Gly
            260                 265                 270
```